(12) United States Patent
Rose et al.

(10) Patent No.: US 9,234,233 B2
(45) Date of Patent: Jan. 12, 2016

(54) METHODS FOR ENHANCING NUCLEIC ACID HYBRIDIZATION

(71) Applicant: Integrated DNA Technologies, Inc., Skokie, IL (US)

(72) Inventors: Scott Rose, Coralville, IA (US); Mark A. Behlke, Coralville, IA (US); Richard Owczarzy, Coralville, IA (US); Joseph A. Walder, Chicago, IL (US); Derek M. Thomas, Cedar Rapids, IA (US); Michael R. Marvin, Coralville, IA (US)

(73) Assignee: Integrated DNA Technologies, Inc., Skokie, IL (US)

( * ) Notice: Subject to any disclaimer, the term of this patent is extended or adjusted under 35 U.S.C. 154(b) by 0 days.

(21) Appl. No.: 14/578,399

(22) Filed: Dec. 20, 2014

(65) Prior Publication Data

US 2015/0141635 A1 May 21, 2015

Related U.S. Application Data

(62) Division of application No. 13/073,866, filed on Mar. 28, 2011, now Pat. No. 8,916,345.

(60) Provisional application No. 61/318,043, filed on Mar. 26, 2010.

(51) Int. Cl.
*C07H 21/02* (2006.01)
*C07H 19/04* (2006.01)
(Continued)

(52) U.S. Cl.
CPC .............. *C12Q 1/6832* (2013.01); *C07H 21/04* (2013.01); *C12Q 1/6818* (2013.01); *G01N 33/5308* (2013.01); *G01N 33/542* (2013.01); *C12Q 1/6851* (2013.01)

(58) Field of Classification Search
CPC .............................. C12Q 1/6832; C07H 21/04
USPC ................................... 536/23.1, 26.6; 435/6.1
See application file for complete search history.

(56) References Cited

U.S. PATENT DOCUMENTS 2,264,303 A 12/1941 Dickey
3,218,309 A 11/1965 Elslager et al.
(Continued)

FOREIGN PATENT DOCUMENTS

DE 2546535 4/1977
EP 0070685 1/1983
(Continued)

OTHER PUBLICATIONS

Shi et al., "Design of Phosphoramidite Monomer for Optimal Incorporation of Functional Intercalator to Main Chain of Oligonucleotide," Bioconjugate Chemistry, vol. 16, No. 2, Mar. 1, 2005, pp. 306-311.
(Continued)

*Primary Examiner* — Jezia Riley
(74) *Attorney, Agent, or Firm* — Michael Best & Friedrich LLP

(57) ABSTRACT

A composition comprising an oligonucleotide having the structure 5'-$Y_1$-$L_1$-X-$L_2$-$Y_2$-3'. $Y_1$ comprises a sequence of one or more DNA or RNA nucleotides, including a first nucleotide $N_1$ having a 3' phosphate covalently linked to $L_1$. $Y_2$ comprises a sequence of one or more DNA or RNA nucleotides, including a second nucleotide $N_2$ having a 5' phosphate covalently linked to $L_2$. $L_1$ and $L_2$ each independently are a direct bond or a $C_1$-$C_7$ alkyl, alkynyl, alkenyl, heteroalkyl, substituted alkyl, aryl, heteroaryl, substituted aryl, cycloalkyl, alkylaryl, or alkoxyl group. X is

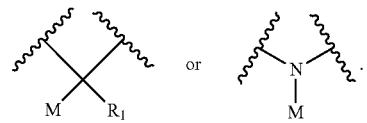

$R_1$ is a hydrogen or a $C_1$-$C_8$ alkyl. M is a label or ligand comprising a fused polycyclic aromatic moiety.

9 Claims, 23 Drawing Sheets

(51) Int. Cl.
*C12Q 1/68* (2006.01)
*C07H 21/04* (2006.01)
*G01N 33/53* (2006.01)
*G01N 33/542* (2006.01)

(56) References Cited

U.S. PATENT DOCUMENTS

| | | | |
|---|---|---|---|
| 3,407,189 A | 10/1968 | Merian |
| 3,970,617 A | 7/1976 | Bruno |
| 4,358,535 A | 11/1982 | Falkow et al. |
| 4,439,356 A | 3/1984 | Khanna et al. |
| 4,683,194 A | 7/1987 | Saiki et al. |
| 4,683,202 A | 7/1987 | Mullis |
| 4,711,955 A | 12/1987 | Ward et al. |
| 4,820,630 A | 4/1989 | Taub |
| 4,835,263 A | 5/1989 | Nguyen et al. |
| 4,868,103 A | 9/1989 | Stavrianopoulos et al. |
| 4,868,105 A | 9/1989 | Urdea et al. |
| 4,889,818 A | 12/1989 | Gelfand et al. |
| 4,914,210 A | 4/1990 | Levenson et al. |
| 4,954,630 A | 9/1990 | Klein et al. |
| 4,996,143 A | 2/1991 | Heller et al. |
| 5,011,769 A | 4/1991 | Duck et al. |
| 5,108,892 A | 4/1992 | Burke et al. |
| 5,124,246 A | 6/1992 | Urdea et al. |
| 5,188,934 A | 2/1993 | Menchen et al. |
| 5,210,015 A | 5/1993 | Gelfand et al. |
| 5,214,136 A | 5/1993 | Lin et al. |
| 5,272,259 A | 12/1993 | Claussen et al. |
| 5,304,645 A | 4/1994 | Klein et al. |
| 5,312,728 A | 5/1994 | Lizardi et al. |
| 5,326,679 A | 7/1994 | Yanagisawa et al. |
| 5,328,824 A | 7/1994 | Ward et al. |
| 5,451,463 A | 9/1995 | Nelson et al. |
| 5,455,157 A | 10/1995 | Hinzpeter et al. |
| 5,484,908 A | 1/1996 | Froehler |
| 5,487,972 A | 1/1996 | Gelfand et al. |
| 5,492,806 A | 2/1996 | Drmanac et al. |
| 5,494,810 A | 2/1996 | Barany et al. |
| 5,502,177 A | 3/1996 | Matteucci et al. |
| 5,512,667 A | 4/1996 | Reed et al. |
| 5,514,785 A | 5/1996 | Van Ness et al. |
| 5,525,464 A | 6/1996 | Drmanac et al. |
| 5,538,848 A | 7/1996 | Livak et al. |
| 5,556,752 A | 9/1996 | Lockhart et al. |
| 5,696,251 A | 12/1997 | Arnold, Jr. et al. |
| 5,801,155 A | 9/1998 | Kutyavin et al. |
| 5,804,375 A | 9/1998 | Gelfand et al. |
| 5,824,796 A | 10/1998 | Petrie et al. |
| 5,830,653 A | 11/1998 | Froehler et al. |
| 5,846,726 A | 12/1998 | Nadeau et al. |
| 5,849,482 A | 12/1998 | Meyer, Jr. et al. |
| 5,876,930 A | 3/1999 | Livak et al. |
| 5,925,517 A | 7/1999 | Tyagi et al. |
| 5,942,610 A | 8/1999 | Nelson et al. |
| 5,952,202 A | 9/1999 | Aoyagi et al. |
| 6,007,992 A | 12/1999 | Lin et al. |
| 6,028,183 A | 2/2000 | Lin et al. |
| 6,084,102 A | 7/2000 | Kutyavin et al. |
| 6,114,518 A | 9/2000 | Pitner et al. |
| 6,117,973 A | 9/2000 | Batz et al. |
| 6,117,986 A | 9/2000 | Nardone et al. |
| 6,214,979 B1 | 4/2001 | Gelfand et al. |
| 6,312,894 B1 | 11/2001 | Hedgpeth et al. |
| 6,316,610 B2 | 11/2001 | Lee et al. |
| 6,323,337 B1 | 11/2001 | Singer et al. |
| 6,399,392 B1 | 6/2002 | Haugland et al. |
| 6,416,953 B1 | 7/2002 | Heller |
| 6,441,159 B1 | 8/2002 | Lukhtanov et al. |
| 6,448,407 B1 | 9/2002 | Lee et al. |
| 6,451,535 B1 | 9/2002 | Jenne et al. |
| 6,465,175 B2 | 10/2002 | Horn et al. |
| 6,465,644 B1 | 10/2002 | Yan et al. |
| 6,485,901 B1 | 11/2002 | Gildea et al. |
| 6,531,581 B1 | 3/2003 | Nardone et al. |
| 6,531,589 B1 | 3/2003 | Iyer et al. |
| 6,531,591 B1 | 3/2003 | Fensholdt |
| 6,653,473 B2 | 11/2003 | Reed et al. |
| 6,699,975 B2 | 3/2004 | Reed et al. |
| 6,727,356 B1 | 4/2004 | Reed et al. |
| 6,790,945 B2 | 9/2004 | Reed et al. |
| 6,800,728 B2 | 10/2004 | Schwartz |
| 6,825,331 B2 | 11/2004 | Manoharan et al. |
| 6,875,858 B1 | 4/2005 | DeFrancq et al. |
| 7,060,809 B2 | 6/2006 | Wengel et al. |
| 7,122,383 B2 | 10/2006 | Jones et al. |
| 7,173,125 B2 | 2/2007 | Schwartz et al. |
| 7,439,341 B2 | 10/2008 | Laikhter et al. |
| 7,476,735 B2 | 1/2009 | Laikhter et al. |
| 7,605,243 B2 | 10/2009 | Laikhter et al. |
| 7,645,872 B2 | 1/2010 | Laikhter et al. |
| 7,803,536 B2 | 9/2010 | Behlke et al. |
| 7,803,936 B2 | 9/2010 | Laikhter et al. |
| 8,916,345 B2 | 12/2014 | Rose |
| 2002/0034754 A1 | 3/2002 | Reed et al. |
| 2002/0137070 A1 | 9/2002 | Elghanian et al. |
| 2003/0082547 A1 | 5/2003 | Ewing et al. |
| 2003/0096254 A1 | 5/2003 | Reed et al. |
| 2003/0144499 A1 | 7/2003 | McGall et al. |
| 2004/0180343 A1 | 9/2004 | Weber |
| 2005/0142598 A1 | 6/2005 | Heindl et al. |
| 2007/0218490 A1 | 9/2007 | Laikhter et al. |
| 2008/0085837 A1 | 4/2008 | Coull et al. |
| 2009/0053821 A1 | 2/2009 | Laikhter et al. |
| 2009/0259030 A1 | 10/2009 | Cook et al. |
| 2010/0298554 A1 | 11/2010 | Laikhter et al. |
| 2011/0060150 A1 | 3/2011 | Laikhter et al. |

FOREIGN PATENT DOCUMENTS

| | | |
|---|---|---|
| EP | 0070686 | 1/1983 |
| EP | 0070687 | 1/1983 |
| EP | 0152886 | 8/1985 |
| EP | 0185494 | 6/1986 |
| EP | 0246864 | 11/1987 |
| EP | 0272007 | 11/1987 |
| EP | 0320308 | 6/1989 |
| EP | 0357011 | 3/1990 |
| EP | 0439182 | 7/1991 |
| GB | 1394368 | 5/1975 |
| GB | 1533121 | 11/1978 |
| JP | 52-88681 | 7/1977 |
| JP | 52-91031 | 8/1977 |
| WO | 89/09284 | 10/1989 |
| WO | 89/10979 | 11/1989 |
| WO | 90/14353 | 11/1990 |
| WO | 91/05060 | 4/1991 |
| WO | 92/10588 | 6/1992 |
| WO | 96/17957 | 6/1996 |
| WO | 96/28460 | 9/1996 |
| WO | 96/34983 | 11/1996 |
| WO | 96/40662 | 12/1996 |
| WO | 97/29154 | 8/1997 |
| WO | 97/39008 | 10/1997 |
| WO | 99/14226 | 3/1999 |
| WO | 99/37717 | 7/1999 |
| WO | 99/40226 | 8/1999 |
| WO | 99/51621 | 10/1999 |
| WO | 99/51775 | 10/1999 |
| WO | 99/64431 | 12/1999 |
| WO | 00/06771 | 2/2000 |
| WO | 00/70685 | 11/2000 |
| WO | 01/04129 | 1/2001 |
| WO | 01/42505 | 6/2001 |
| WO | 01/86001 | 11/2001 |
| WO | 03/019145 | 3/2003 |
| WO | 2004/026804 | 4/2004 |
| WO | 2004/113562 | 12/2004 |
| WO | 2005/049849 | 6/2005 |
| WO | 2006/081035 | 8/2006 |
| WO | 2006/127507 | 4/2007 |

(56) References Cited

FOREIGN PATENT DOCUMENTS

WO 2010/147673 12/2010
WO 2011/120049 9/2011

OTHER PUBLICATIONS

Australian Patent Examination Report No. 2 for Application No. 2011230496 dated Jun. 22, 2015 (3 pages).
7th International Symposium, held 2001, pp. 1-14, 7th International Symposium & Exhibition Solid Phase Synthesis & Combinatorial Chemical Libraries, Sep. 18-22, 2001—University of Southampton, England, UK.
Agrawal, S. et al., "Efficient methods for attaching non-radioactive labels to the 5' ends of synthetic oligodeoxyribonucleotides," Nuc. Acids Res. (1986) 14:6227-6245.
Austermann, S. et al., "Inhibition of human immunodeficiency virus type 1 reverse transcriptase by 3'-blocked oligonucleotide primers," Biochem. Pharm. (1992) 43(12):2581-2589.
Bailly, C. et al., "DNA recognition by intercalator-minor-groove binder hybrid molecules," Bioconjugate Chem. (1991) 2(6):379-393.
Bollum, F.J., "Oligodeoxyribonucleotide-primed reactions catalyzed by calf thymus polymerase," J. Bio. Chem. (1962) 237(6):1945-1949.
Boturyn, D. et al., "Synthesis of Fluorescent probes for the Detection of Abasic Sites in DNA," Tetrahedron (1997) 53(15):5485-5492.
Bustin, S.A., "Quantification of mRNA using real-time reverse transcription PCR (RT-PCR): trends and problems," Mol. Endocrin. (2002) 29:23-29.
Cardullo, R.A et al., "Detection of nucleic acid hybridization by nonradiative fluorescence resonance energy transfer," Proc. Natl. Acad. Sci. USA (1988) 85:8790-8794.
Caruthers, M.H. et al., "Chemical synthesis of deoxyoligonucleotides and deoxyoligonucleotide analogs," Methods Enzymol. (1992) 211:3-20.
Conference Proceedings, retrieved 2010, two pages, Innovation and Perspectives in Solid Phase Synthesis & Combinatorial Libraries: Peptides, Proteins and Nucleic Acids—Small Molecule Organic Chemistry Diversity, Collected Papers, International Symposium, 7th, Southampton, United Kingdom, Sep. 18-22, 2001, Roger Epton, Editor.
Dey, S. and Sheppard, T.L., "Ketone-DNA: a versatile postsynthetic DNA decoration platform," Org. Lett. (2001) 3(25):3983-3986.
Dirks, R.W. et al., "Advances in fluorescent tracking of nucleic acids in living cells," Biotechniques (2006) 40:489-496.
Dogan, Z. et al., "5'-tethered stilbene derivatives as fidelity- and affinity-enhancing modulators of DNA duplex stability," J. Am. Chem. Soc. (2004) 126:4762-4763.
Doktycz, M.J. et al., "Studies of DNA dumbbells. I. Melting curves of 17 DNA dumbbells with different duplex stem sequences linked by T4 endloops: evaluation of the nearest-neighbor stacking interactions in DNA," Biopolymers (1992) 32:849-864.
Easy Q&Q PCR, http://www.eurogentec.be/code/en/product_easy_qq.htm, visited May 9, 2002, 4 pages.
Encyclopedia Britannica (2008) "Nucleic Acid," Encyclopedia Britannica Online (Jul. 11, 2008) http://www.search.eb.com/eb/article-256731.
Gelfand, D.H., "Taq DNA Polymerase," PCR Technology Principles and Applications for DNA Amplification, Stockton Press, NY, Ehrlich ed. (1989) Ch. 2, 17-22.
Genbank Accession No. AF298116, Rose et al., "*Mus musculus* bHLH protein Ptf1-p48 gene," (2001) 6 pages.
Gibson, V. et al., "Molecular modelling of anthraquinone-oligodeoxynucleotide conjugates," Pharm. Sci. (1996) 2:545-548.
Gorelick, M.V. et al., "Effect of benzannelation on the coloration of p-aminoazo compounds," Zhurnal Organicheskoi Khimii (1980) 16(9):1927-1933—Abstract only—Accession No. 1981:193676.
Heesemann, J., "Studies on monolayers. 1. Surface tension and absorption spectroscopic measurements of monolayers of surface-active azo and stilbene dyes," J. Am. Chem. Soc. (1980) 102(7):2167-2176.
Heller, M.J. et al., "Chemiluminescent and fluorescent probes for DNA hybridization systems," Rapid Detection and Identification of Infectious Agents (1985) Academic Press, Inc., Orlando, Kingsbury et al. eds. 245-256.
Ho, M.S. et al., "Azo polymers for reversible optical storage. 7. The effect of the size of the photochromic groups," Macromolecules (1995) 28(18):6124-6127 (Abstract only—Accession No. 1995:746851).
Hugentobler, M. et al., "Compounds with a metal-arene σ-bond. Part 2. Cyclometalation of arylazo compounds. Part 2. Regioselectivity of the cyclopalladation of some substituted 1-arylazonaphthalenes," Helvetica Chimica Acta (1982) 65(4):1202-1211 (Abstract only—Accession No. 1982:616430).
Ito, T. et al., "Reductive Electron Injection into Duplex DNA by Aromatic Amines," J. Am. Chem. Soc. (2004) 126:15552-15559.
Iyer, R.P. et al., "3H-1,2-benzodithiole-3-one 1,1-dioxide as an improved sulfurizing reagent in the solid-phase synthesis of oligodeoxyribonucleoside phosphorothioates," J. Am. Chem. Soc. (1990) 112:1253-1254.
Jenkins, J.H., Senior Librarian at the United States Patent and Trademark Office, email dated Mar. 18, 2010 and previously related email corespondence, pp. 1-2.
Jiao, G.-S. et al., "Oligonucleotides with strongly fluorescent groups Π-conjugated to a nucleobase: syntheses, melting temperatures, and conformation," Bioorg. Med. Chem. Lett. (2003) 13(16):2785-2788.
Ju, J. et al., "Fluorescence energy transfer dye-labeled primers for DNA sequencing and analysis," Proc. Natl. Acad. Sci. USA (1995) 92:4347-4351.
Kerzhner, B.K. et al., "Photoisomerization of aromatic azo compounds adsorbed on a hydroxylated surface," Zhurnal Obshchei Khimii (1983) 53(10):2303-2306 (Abstract only—Accession No. 1984:50840).
Kuball, H.-G. et al., "Helical twisting power of chiral mono- and bis-aminoanthraquinones," J. Mater. Chem. (1995) 5 (12):2167-2174.
Lawyer, F.C. et al., "Isolation, characterization, and expression in *Escherichia coli* of the DNA polymerase gene from thermus aquaticus," J. Biol. Chem. (1989) 264(11):6427-6437.
Lehman, I.R. et al., "Persistence of deoxyribonucleic acid polymerase I and its 5' →3' exonuclease activity in PolA mutants of *Escherichia coli* K12," J. Biol. Chem. (1973) 248(22):7717-7723.
Lewis, F.D. et al., "Hybrid oligonucleotides containing stilbene units. Excimer fluorescence and photodimerization," J. Am. Chem. Soc. (1995) 117:8785-8792.
Mackay, I.M., "Real-time PCR in the microbiology laboratory," Clin. Microbiol. Infect. (2004) 10:190-212.
Marshall, "Rules for the visible absorption spectra of halogenated fluorescein dyes," Histochemical J. (1975) 7:299-303.
Matthews, J.A. et al., "Analytical strategies for the use of DNA probes," Analy. Biochem. (1988) 169:1-25.
May, J.P. et al., "A new dark quencher for use in genetic analysis," Chem. Commun. (2003) 970-971.
May, J.P. et al., "A novel dark quencher for oligonucleotide probes: synthesis and applications," poster presentation from TIDES 2002 IBC Oligonucleotide and Peptide Technology Conference, May 6-8, 2002, Las Vegas, Nevada (2 pages).
May, J.P. et al., "Synthesis of a novel dark quencher for use with long wavelength dyes in oligonucleotide probes," Innovation and Perspectives in Solid Phase Synthesis & Combinatorial Libraries: Peptides, Proteins and Nucleic Acids Small Molecule Organic Chemical Diversity, Collected Papers, 7th International Symposium, Southampton, United Kingdom, Sep. 18-22, 2002, 231-233.
Mineno, J. et al., "Fluorescent labeling of a DNA sequencing primer," DNA Sequence—J. DNA Seequence and Mapping (1993) 4:135-141.
Misiura, K. et al., "Biotinyl and phosphotyrosinyl phosphoramidite derivatives useful in the incorporation of multiple reporter groups on synthetic oligonucleotides," Nucleic Acids Research (1990) 18(15):4345-4354.
Miyashita, T. et al., "Novel dinucleoside phosphotriester unit conjugated with an intercalative moiety in a stereospecific manner enhances thermal stability of an alternate-stranded triple helix," Tetrahedron Letters (2003) 44:7399-7402.

(56) References Cited

OTHER PUBLICATIONS

Mori, K. et al., "Oligodeoxynucleotide analogs with 5'-linked anthraquinone," FEBS Letters (1989) 249(2):213-218.
Morier-Teissier, E. et al., "Free radical production and DNA cleavage by copper chelating peptide-anthraquinones," Anti-Cancer Drug Design (1990) 5:291-305.
Morrison, L.E. et al., "Solution-phase detection of polynucleotides using interacting fluorescent labels and competitive hybridization," Anal. Biochem. (1989) 183:231-244.
Mullis, K. et al., "Specific Enzymatic Amplification of DNA In Vitro: The Polymerase Chain Reaction," Cold Spring Harbor Symp. Quant. Biol. (1986) 51:263-273.
Narayanan, S. et al., "Clamping down on weak terminal base pairs: oligonucleotides with molecular caps as fidelity-enhancing elements at the 5'- and 3'-terminal residues," Nucl. Acids. Res. (2004) 32:2901-2911.
Noble, S.A. et al, "Methylphosphonates as probes of protein-nucleic acid interactions," Nuc. Acids Res. (1984) 12(7):3387-3404.
Owczarzy, R. et al., "Predicting stability of DNA duplexes in solutions containing magnesium and monovalent cations," Biochem. (2008) 47:5336-5353.
Owczarzy, R. et al., "Predicting sequence-dependent melting stability of short duplex DNA oligomers," Biopolymers (1997) 44:217-239.
Owczarzy, R., "Melting temperatures of nucleic acids: discrepancies in analysis," Biophys. Chem. (2005) 117:207-215.
Patra, A. et al., "High fidelity base pairing at the 3'-terminus," J. Am. Chem. Soc. (2009) 131(35):12671-12681.
Petersheim, M. et al., "Base-stacking and base-pairing contributions to helix stability: thermodynamics of double-helix formation with CCGG, CCGGp, CCGGAp, ACCGGp, CCGGUp, and ACCGGUp," Biochem. (1983) 22:256-263.
PR Newswire, Announcing IBC's TIDES 2002: Oligonucleotide and Peptide Technology Conferences May 6-8, 2002, Las Vegas, NV, Copyright 2002, PR Newswire Association LLC, pp. 1-2, website (retrieved Mar. 18, 2010): http://www.thefreelibrary.com/_/print/PrintArticle.aspx?id=82059345.
Proudnikov, D. et al., "Chemical methods of DNA and RNA fluorescent labeling," Nucleic Acids Res. (1996) 24(22):4535-4542.
Puskas, L.G. et al., "Diamino-Antraquinone: A New Intercalating Agent. Synthesis and Linking to Oligodeoxynucleotide," Nucleosides & Nucleotides (1995) 14(3-5):967-968.
Rose, S.D. et al., "The Role of PTF1-P48 in pancreatic acinar gene expression," J. Biol. Chem. (2001) 276 (47):44018-44026.
Rychlik, W. et al., "Optimization of the annealing temperature for DNA amplification in vitro," Nucl. Acids. Res. (1990) 18:6409-6412.
Santalucia, J, Jr., "A unified view of polymer, dumbbell, and oligonucleotide DNA nearest-neighbor thermodynamics," Proc. Natl. Acad. Sci. USA (1998) 95:1460-1465.
Schuster, G.B., "Long-range charge transfer in DNA: transient structural distortions control the distance dependence," Acc. Chem. Res. (2000) 33:253-260.
Setlow, P. et al., "Deoxyribonucleic acid polymerase: two distinct enzymes in one polypeptide," J. Biol. Chem. (1972) 247(1):224-231.
Sijm, D.T.H.M. et al., "Aqueous solubility, octanol solubility, and octanol/water partition coefficient of nine hydrophobic dyes," Envir. Toxic. Chem. (1999) 18(6):1109-1117.
Telser, J. et al., "Synthesis and characterization of DNA oligomers and duplexes containing covalently attached molecular labels: comparison of biotin, fluorescein, and pyrene labels by thermodynamic and optical spectroscopic measurements," J. Am. Chem. Soc. (1989) 111:6966-6967.
Tu, C-P.D. et al., "3'-end labeling of DNA with [α-32P]cordycepin-5'-triphosphate," Gene (1980) 10:177-183.
Warshaw, M.M. et al., "Optical properties of sixteen dinucleoside phosphates," J. Mol. Biol. (1966) 20:29-38.
Wetmur, J.G., "DNA probes: applications of the principles of nucleic acid hybridization," Critical Review in Biochem. and Mol. Biol. (1991) 26(3/4):227-259.
Schnippering et al., "Synthesis and electrochemical properties of TTF modified oligodeoxynucleotides," Chemical Communications, No. 37, Jan. 1, 2009, p. 5552.
Ansanuma et al., "Enantioselective Incorporation of Azobenzenes into Oligodeoxyribonucleotide for Effective Photoregulation of Duplex Formation**", Angew. Chem. Int. Ed., vol. 40, No. 14, Jan. 1, 2001, pp. 2671-2673.
"Prokhorenko et al., ""Incorporation of a pyrene nucleoside analogue intosynthetic oligodeoxynucleotides using a nucleoside-like synthon"",Bioorganic & Medicinal Chemistry Letters, Pergamon, vol. 5, No. 18, Sep. 21, 1995, pp. 2081-2084."
Ossipov et al., "Dipyrido[3,2-a:2', 3'-c]phenazi ne-Tethered Oligo-DNA: Synthesis and Thermal Stability of Their DNA'DNA and DNA'RNA Duplexes and DNA'DNA'DNA Triplexes", Helvetica Chimica Acta, vol. 82, Jan. 1, 1999, pp. 2186-2200.
Liang et al., "An interstrand-wedged duplex composed of alternating DNA base pairs and covalently attached intercalators," Journal of Material Chemistry, vol. 20, No. 3, Jan. 1, 2009, p. 575.
Wang et al Chinese j. of Chem., vol. 27, No. 8, pp. 1582-1588 (2009).
Zielske, A.G., "(Tosyloxy)anthraquinones: Versatile Synthons for the Preparation of Various Aminoanthraquinones," J. Org. Chem. (1987) 52:1305-1309.
International Search Report and Written Opinion for Application No. PCT/US2011/30215 dated May 23, 2011 (9 pages).
International Preliminary Report on Patentability for Application No. PCT/US2011/30215 dated Oct. 2, 2012 (8 pages).
European Patent Office Search Report for Application No. 11760380 dated Aug. 20, 2013 (10 pages).
United States Patent Office Action for U.S. Appl. No. 13/073,866 dated Jun. 17, 2013 (6 pages).
European Patent Office Action for Application No. 11760380.3 dated Apr. 14, 2014 (5 pages).
Australian Patent Examination Report No. 1 for Application No. 2011230496 dated Jun. 16, 2014 (5 pages).
Australian Patent Examination Report No. 1 for Application No. 2013202227 dated May 28, 2014 (3 pages).
United States Patent Office Notice of Allowance for U.S. Appl. No. 13/073,866 dated Aug. 15, 2014 (5 pages).
European Patent Office Action for Application No. 11760380.3 dated Feb. 18, 2015 (4 pages).
Japanese Patent Office Action for Application No. 2013-502702 dated Mar. 2, 2015 (6 pages, English translation included).
US 6,255,052, 05/2001, Batz et al. (withdrawn)

IB 1.1:

FQ:

Epoch Eclipse:

Black Hole 2:

SEQUENCE LISTING

```
<160> NUMBER OF SEQ ID NOS: 147

<210> SEQ ID NO 1
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 1
atcgttgcta                                                            10

<210> SEQ ID NO 2
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 2
tagcaacgat                                                            10

<210> SEQ ID NO 3
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iFQ is inserted between nucleotide positions 3
      and 4.

<400> SEQUENCE: 3
atcgttgcta                                                            10

<210> SEQ ID NO 4
```

```
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iFQ is inserted between nucleotide positions 4
      and 5.

<400> SEQUENCE: 4
atcgttgcta                                                              10

<210> SEQ ID NO 5
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iFQ is inserted between nucleotide positions 5
      and 6.

<400> SEQUENCE: 5
atcgttgcta                                                              10

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cttggatcgt tgctagtagg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cctactagca acgatccaag                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: iFQ is inserted between nucleotide positions 10
      and 11.

<400> SEQUENCE: 8
cttggatcgt tgctagtagg                                                   20

<210> SEQ ID NO 9
<211> LENGTH: 25
<212> TYPE: DNA
<213> ORGANISM: Artificial Sequence
<220> FEATURE:
```

<223> OTHER INFORMATION: Synthetic oligonucleotide

<400> SEQUENCE: 9
cacttggatc gttgctagta gggtc                              25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
gaccctacta gcaacgatcc aagtg                              25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (10)..(11)
<223> OTHER INFORMATION: iFQ is inserted between nucelotide positions 10
      and 11.

<400> SEQUENCE: 11
cacttggatc gttgctagta gggtc                              25

<210> SEQ ID NO 12
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iSpC3 is inserted between nucleotide positions
      3 and 4.

<400> SEQUENCE: 12
atcgttgcta                                               10

<210> SEQ ID NO 13
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iSpC3 is inserted between nucleotide positions
      4 and 5.

<400> SEQUENCE: 13
atcgttgcta                                               10

<210> SEQ ID NO 14
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)

```
<223> OTHER INFORMATION: iSpC3 is inserted between nucleotide positions
      5 and 6.

<400> SEQUENCE: 14
atcgttgcta                                                                10

<210> SEQ ID NO 15
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iSpC3 is inserted between nucleotide positions
      5 and 6.

<400> SEQUENCE: 15
tagcaacgat                                                                10

<210> SEQ ID NO 16
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 16
tagcaaacga t                                                              11

<210> SEQ ID NO 17
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 17
tagcacacga t                                                              11

<210> SEQ ID NO 18
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 18
tagcagacga t                                                              11

<210> SEQ ID NO 19
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 19
tagcatacga t                                                              11

<210> SEQ ID NO 20
<211> LENGTH: 10
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: (3)..(4)
<223> OTHER INFORMATION: N-MDA is inserted between nucleotide positions
      3 and 4.

<400> SEQUENCE: 20
atcgttgcta                                                              10

<210> SEQ ID NO 21
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: C2 is inserted between nucleotide positions 3
      and 4.

<400> SEQUENCE: 21
atcgttgcta                                                              10

<210> SEQ ID NO 22
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: 2,2 DMP is inserted between nucleotide
      positions 3 and 4.

<400> SEQUENCE: 22
atcgttgcta                                                              10

<210> SEQ ID NO 23
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: C4 is inserted between nucleotide positions 3
      and 4.

<400> SEQUENCE: 23
atcgttgcta                                                              10

<210> SEQ ID NO 24
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: C5 is inserted between nucleotide positions 3
      and 4.

<400> SEQUENCE: 24
atcgttgcta                                                              10
```

```
<210> SEQ ID NO 25
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: C6 is inserted between nucleotide positions 3
      and 4.

<400> SEQUENCE: 25
atcgttgcta                                                              10

<210> SEQ ID NO 26
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: C7 is inserted between nucleotide positions 3
      and 4.

<400> SEQUENCE: 26
atcgttgcta                                                              10

<210> SEQ ID NO 27
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iSpS9 is inserted between nucleotide positions
      3 and 4.

<400> SEQUENCE: 27
atcgttgcta                                                              10

<210> SEQ ID NO 28
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: idSp is inserted between nucelotide positions 3
      and 4.

<400> SEQUENCE: 28
atcgttgcta                                                              10

<210> SEQ ID NO 29
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iBHQ2 is inserted between nucleotide positions
      3 and 4.
```

```
<400> SEQUENCE: 29
atcgttgcta                                                              10

<210> SEQ ID NO 30
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iRQ-n1 is inserted between nucleotide positions
      3 and 4.

<400> SEQUENCE: 30
atcgttgcta                                                              10

<210> SEQ ID NO 31
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iRQ-n2 is inserted between nucleotide positions
      3 and 4.

<400> SEQUENCE: 31
atcgttgcta                                                              10

<210> SEQ ID NO 32
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: iEc is inserted between nucleotide positions 3
      and 4.

<400> SEQUENCE: 32
atcgttgcta                                                              10

<210> SEQ ID NO 33
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(4)
<223> OTHER INFORMATION: IB 1.1 is inserted between nucleotide positions
      3 and 4.

<400> SEQUENCE: 33
atcgttgcta                                                              10

<210> SEQ ID NO 34
<211> LENGTH: 10
<212> TYPE: DNA
<213> ORGANISM: Artificial Sequence
<220> FEATURE:
```

```
<223> OTHER INFORMATION: Synthetic oligonucleotide
<220> FEATURE:
<221> NAME/KEY: misc_feature
<222> LOCATION: (3)..(4)
<223> OTHER INFORMATION: NPDA is inserted between nucleotide positions 3
      and 4.

<400> SEQUENCE: 34
atcgttgcta                                                                10

<210> SEQ ID NO 35
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: N-MDA is inserted between nucleotide positions
      4 and 5.

<400> SEQUENCE: 35
atcgttgcta                                                                10

<210> SEQ ID NO 36
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: C2 is inserted between nucleotide positions 4
      and 5.

<400> SEQUENCE: 36
atcgttgcta                                                                10

<210> SEQ ID NO 37
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: 2,2 DMP is inserted between nucleotide
      positions 4 and 5.

<400> SEQUENCE: 37
atcgttgcta                                                                10

<210> SEQ ID NO 38
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: C4 is inserted between nucleotide positions 4
      and 5.

<400> SEQUENCE: 38
atcgttgcta                                                                10
```

```
<210> SEQ ID NO 39
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: C5 is inserted between nucleotide positions 4
      and 5.

<400> SEQUENCE: 39
atcgttgcta                                                             10

<210> SEQ ID NO 40
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: C6 is inserted between nucleotide positions 4
      and 5.

<400> SEQUENCE: 40
atcgttgcta                                                             10

<210> SEQ ID NO 41
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: C7 is inserted between nucleotide positions 4
      and 5.

<400> SEQUENCE: 41
atcgttgcta                                                             10

<210> SEQ ID NO 42
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iSpS9 is inserted between nucleotide positions
      4 and 5.

<400> SEQUENCE: 42
atcgttgcta                                                             10

<210> SEQ ID NO 43
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: idSp is inserted between nucleotide positions
```

4 and 5.

<400> SEQUENCE: 43
atcgttgcta                                                                10

<210> SEQ ID NO 44
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iBHQ2 is inserted between nucleotide positions
      4 and 5.

<400> SEQUENCE: 44
atcgttgcta                                                                10

<210> SEQ ID NO 45
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iRQ-n1 is inserted between nucleotide positions
      4 and 5.

<400> SEQUENCE: 45
atcgttgcta                                                                10

<210> SEQ ID NO 46
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iRQ-n2 is inserted between nucleotide positions
      4 and 5.

<400> SEQUENCE: 46
atcgttgcta                                                                10

<210> SEQ ID NO 47
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: iEc is inserted between nucleotide positions 4
      and 5.

<400> SEQUENCE: 47
atcgttgcta                                                                10

<210> SEQ ID NO 48
<211> LENGTH: 10
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: IB 1.1 is inserted between nucleotide positions
      4 and 5.

<400> SEQUENCE: 48
atcgttgcta                                                              10

<210> SEQ ID NO 49
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(5)
<223> OTHER INFORMATION: NPDA is inserted between nucleotide positions 4
      and 5.

<400> SEQUENCE: 49
atcgttgcta                                                              10

<210> SEQ ID NO 50
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: C2 is inserted between nucleotide positions 5
      and 6.

<400> SEQUENCE: 50
atcgttgcta                                                              10

<210> SEQ ID NO 51
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: 2,2 DMP is inserted between nucleotide
      positions 5 and 6.

<400> SEQUENCE: 51
atcgttgcta                                                              10

<210> SEQ ID NO 52
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: C4 is inserted between nucleotide positions 5
      and 6.

<400> SEQUENCE: 52
atcgttgcta                                                              10
```

```
<210> SEQ ID NO 53
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: C5 is inserted between nucleotide positions 5
      and 6.

<400> SEQUENCE: 53
atcgttgcta                                                          10

<210> SEQ ID NO 54
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: C6 is inserted between nucleotide positions 5
      and 6.

<400> SEQUENCE: 54
atcgttgcta                                                          10

<210> SEQ ID NO 55
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: C7 is inserted between nucleotide positions 5
      and 6.

<400> SEQUENCE: 55
atcgttgcta                                                          10

<210> SEQ ID NO 56
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iSpS9 is inserted between nucleotide positions
      5 and 6.

<400> SEQUENCE: 56
atcgttgcta                                                          10

<210> SEQ ID NO 57
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
```

```
<223> OTHER INFORMATION: idSp is inserted between nucleotide positions 5
      and 6.

<400> SEQUENCE: 57
atcgttgcta                                                              10

<210> SEQ ID NO 58
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iBHQ2 is inserted between nucleotide positions
      5 and 6.

<400> SEQUENCE: 58
atcgttgcta                                                              10

<210> SEQ ID NO 59
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iRQ-n1 is inserted between nucleotide positions
      5 and 6.

<400> SEQUENCE: 59
atcgttgcta                                                              10

<210> SEQ ID NO 60
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iRQ-n2 is inserted between nucleotide positions
      5 and 6.

<400> SEQUENCE: 60
atcgttgcta                                                              10

<210> SEQ ID NO 61
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: iEc is inserted between nucleotide positions 5
      and 6.

<400> SEQUENCE: 61
atcgttgcta                                                              10

<210> SEQ ID NO 62
<211> LENGTH: 10
<212> TYPE: DNA
```

<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: IB 1.1 is inserted between nucleotide positions
      5 and 6.

<400> SEQUENCE: 62
atcgttgcta                                                                10

<210> SEQ ID NO 63
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(6)
<223> OTHER INFORMATION: NPDA is inserted between nucleotide positions 5
      and 6.

<400> SEQUENCE: 63
atcgttgcta                                                                10

<210> SEQ ID NO 64
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: N-MDA is inserted between nucleotide positions
      1 and 2.

<400> SEQUENCE: 64
atcgttgcta                                                                10

<210> SEQ ID NO 65
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: C2 is inserted between nucleotide positions 1
      and 2.

<400> SEQUENCE: 65
atcgttgcta                                                                10

<210> SEQ ID NO 66
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: 2,2 DMP is inserted between nucleotide
      positions 1 and 2.

<400> SEQUENCE: 66

```
atcgttgcta                                                              10

<210> SEQ ID NO 67
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iSpC3 is inserted between nucleotide positions
      1 and 2.

<400> SEQUENCE: 67
atcgttgcta                                                              10

<210> SEQ ID NO 68
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: C4 is inserted between nucleotide positions 1
      and 2.

<400> SEQUENCE: 68
atcgttgcta                                                              10

<210> SEQ ID NO 69
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: C5 is inserted between nucleotide positions 1
      and 2.

<400> SEQUENCE: 69
atcgttgcta                                                              10

<210> SEQ ID NO 70
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: C6 is inserted between nucleotide positions 1
      and 2.

<400> SEQUENCE: 70
atcgttgcta                                                              10

<210> SEQ ID NO 71
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
```

```
<222> LOCATION: (1)..(2)
<223> OTHER INFORMATION: C7 is inserted between nucleotide positions 1
      and 2.

<400> SEQUENCE: 71
atcgttgcta                                                           10

<210> SEQ ID NO 72
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iSpS9 is inserted between nucleotide positions
      1 and 2.

<400> SEQUENCE: 72
atcgttgcta                                                           10

<210> SEQ ID NO 73
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: idSp is inserted between nucleotide positions 1
      and 2.

<400> SEQUENCE: 73
atcgttgcta                                                           10

<210> SEQ ID NO 74
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iFQ is inserted between nucleotide positions 1
      and 2.

<400> SEQUENCE: 74
atcgttgcta                                                           10

<210> SEQ ID NO 75
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iBHQ2 is inserted between nucleotide positions
      1 and 2.

<400> SEQUENCE: 75
atcgttgcta                                                           10

<210> SEQ ID NO 76
<211> LENGTH: 10
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iRQ-n1 is inserted between nucleotide positions
      1 and 2.

<400> SEQUENCE: 76
atcgttgcta                                                              10

<210> SEQ ID NO 77
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iRQ-n2 is inserted between nucleotide positions
      1 and 2.

<400> SEQUENCE: 77
atcgttgcta                                                              10

<210> SEQ ID NO 78
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: iEc is inserted between nucleotide positions 1
      and 2.

<400> SEQUENCE: 78
atcgttgcta                                                              10

<210> SEQ ID NO 79
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: IB 1.1 is inserted between nucleotide positions
      1 and 2.

<400> SEQUENCE: 79
atcgttgcta                                                              10

<210> SEQ ID NO 80
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: NPDA is inserted between nucleotide positions 1
      and 2.

<400> SEQUENCE: 80
```

```
atcgttgcta                                                            10

<210> SEQ ID NO 81
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: C2 is inserted between nucleotide positions 9
      and 10.

<400> SEQUENCE: 81
atcgttgcta                                                            10

<210> SEQ ID NO 82
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: 2,2 DMP is inserted between nucleotide
      positions 9 and 10.

<400> SEQUENCE: 82
atcgttgcta                                                            10

<210> SEQ ID NO 83
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iSpC3 is inserted between nucleotide positions
      9 and 10.

<400> SEQUENCE: 83
atcgttgcta                                                            10

<210> SEQ ID NO 84
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: C4 is inserted between nucleotide positions 9
      and 10.

<400> SEQUENCE: 84
atcgttgcta                                                            10

<210> SEQ ID NO 85
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (9)..(10)
<223> OTHER INFORMATION: C5 is inserted between nucleotide positions 9
      and 10.

<400> SEQUENCE: 85
atcgttgcta                                                                  10

<210> SEQ ID NO 86
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: C6 is inserted between nucleotide positions 9
      and 10.

<400> SEQUENCE: 86
atcgttgcta                                                                  10

<210> SEQ ID NO 87
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: C7 is inserted between nucleotide positions 9
      and 10.

<400> SEQUENCE: 87
atcgttgcta                                                                  10

<210> SEQ ID NO 88
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iSpS9 is inserted between nucleotide positions
      9 and 10.

<400> SEQUENCE: 88
atcgttgcta                                                                  10

<210> SEQ ID NO 89
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: idSp is inserted between nucleotide positions 9
      and 10.

<400> SEQUENCE: 89
atcgttgcta                                                                  10

<210> SEQ ID NO 90
```

-continued

<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iFQ is inserted between nucleotide positions 9
      and 10.

<400> SEQUENCE: 90
atcgttgcta                                                          10

<210> SEQ ID NO 91
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iBHQ2 is inserted between nucleotide positions
      9 and 10.

<400> SEQUENCE: 91
atcgttgcta                                                          10

<210> SEQ ID NO 92
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iRQ-n1 is inserted between nucleotide positions
      9 and 10.

<400> SEQUENCE: 92
atcgttgcta                                                          10

<210> SEQ ID NO 93
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iRQ-n2 is inserted between nucleotide positions
      9 and 10.

<400> SEQUENCE: 93
atcgttgcta                                                          10

<210> SEQ ID NO 94
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: iEc is inserted between nucleotide positions 9
      and 10.

```
<400> SEQUENCE: 94
atcgttgcta                                                                          10

<210> SEQ ID NO 95
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: IB 1.1 is inserted between nucleotide positions
      9 and 10.

<400> SEQUENCE: 95
atcgttgcta                                                                          10

<210> SEQ ID NO 96
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: NPDA is inserted between nucleotide positions 9
      and 10.

<400> SEQUENCE: 96
atcgttgcta                                                                          10

<210> SEQ ID NO 97
<211> LENGTH: 21
<212> TYPE: DNA
<213> ORGANISM: Homo sapiens

<400> SEQUENCE: 97
gactttgctt tccttggtca g                                                             21

<210> SEQ ID NO 98
<211> LENGTH: 22
<212> TYPE: DNA
<213> ORGANISM: Homo sapiens

<400> SEQUENCE: 98
ggcttatatc caacacttcg tg                                                            22

<210> SEQ ID NO 99
<211> LENGTH: 26
<212> TYPE: DNA
<213> ORGANISM: Homo sapiens

<400> SEQUENCE: 99
atggtcaagg tcgcaagctt gctggt                                                        26

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
```

```
<220> FEATURE:
<221> NAME/KEY: misc_feature
<222> LOCATION: (11)..(12)
<223> OTHER INFORMATION: iFQ is inserted between nucleotide positions 11
      and 12.
<220> FEATURE:
<221> NAME/KEY: misc_feature
<222> LOCATION: (25)..(25)
<223> OTHER INFORMATION: n is dT modified with SpC3.

<400> SEQUENCE: 100
ntggtcaagg tgcaagcttg ctggn                                            25

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (25)..(25)
<223> OTHER INFORMATION: n is dT modified with SpC3.

<400> SEQUENCE: 101
ntggtcaagt cgcaagcttg ctggn                                            25

<210> SEQ ID NO 102
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (7)..(8)
<223> OTHER INFORMATION: iFQ is inserted between nucleotide positions 7
      and 8.
<220> FEATURE:
<221> NAME/KEY: misc_feature
<222> LOCATION: (25)..(25)
<223> OTHER INFORMATION: n is dT modified with SpC3.

<400> SEQUENCE: 102
ntggtcaggt cgcaagcttg ctggn                                            25

<210> SEQ ID NO 103
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (5)..(6)
<223> OTHER INFORMATION: iFQ is inserted between nucleotide positions 5
```

-continued and 6.
<220> FEATURE:
<221> NAME/KEY: misc_feature
<222> LOCATION: (25)..(25)
<223> OTHER INFORMATION: n is dT modified with SpC3.

<400> SEQUENCE: 103
ntggtaaggt cgcaagcttg ctggn                                              25

<210> SEQ ID NO 104
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (11)..(12)
<223> OTHER INFORMATION: iFQ is inserted between nucleotide positions 11
      and 12.
<220> FEATURE:
<221> NAME/KEY: misc_feature
<222> LOCATION: (26)..(26)
<223> OTHER INFORMATION: n is dT modified with SpC3.

<400> SEQUENCE: 104
ntggtcaagg tcgcaagctt gctggn                                             26

<210> SEQ ID NO 105
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with SpC3.

<400> SEQUENCE: 105
ntggtcaagg tcgcaagctt gctggn                                             26

<210> SEQ ID NO 106
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (7)..(8)
<223> OTHER INFORMATION: iFQ is inserted between nucleotide positions 7
      and 8.
<220> FEATURE:
<221> NAME/KEY: misc_feature
<222> LOCATION: (26)..(26)

<223> OTHER INFORMATION: n is dT modified with SpC3.

<400> SEQUENCE: 106
ntggtcaagg tcgcaagctt gctggn                                    26

<210> SEQ ID NO 107
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (5)..(6)
<223> OTHER INFORMATION: iFQ is inserted between nucleotide positions 5
      and 6.
<220> FEATURE:
<221> NAME/KEY: misc_feature
<222> LOCATION: (26)..(26)
<223> OTHER INFORMATION: n is dT modified with SpC3.

<400> SEQUENCE: 107
ntggtcaagg tcgcaagctt gctggn                                    26

<210> SEQ ID NO 108
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (26)..(26)
<223> OTHER INFORMATION: n is dT modified with FQ.

<400> SEQUENCE: 108
ntggtcaagg tcgcaagctt gctggn                                    26

<210> SEQ ID NO 109
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with FQ.

<400> SEQUENCE: 109
ntggtcaagg tcgcaagctt gctggn                                    26

<210> SEQ ID NO 110
<211> LENGTH: 26

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (9)..(10)
<223> OTHER INFORMATION: iBHQ1 is inserted between nucleotide positions
      9 and 10.
<220> FEATURE:
<221> NAME/KEY: misc_feature
<222> LOCATION: (26)..(26)
<223> OTHER INFORMATION: n is dT modified with BHQ1.

<400> SEQUENCE: 110
ntggtcaagg tcgcaagctt gctggn                                           26

<210> SEQ ID NO 111
<211> LENGTH: 23
<212> TYPE: DNA
<213> ORGANISM: H1N1 influenza A virus

<400> SEQUENCE: 111
gtgctataaa caccagccty cca                                              23

<210> SEQ ID NO 112
<211> LENGTH: 24
<212> TYPE: DNA
<213> ORGANISM: H1N1 influenza A virus

<400> SEQUENCE: 112
cgggatattc cttaatcctg trgc                                             24

<210> SEQ ID NO 113
<211> LENGTH: 30
<212> TYPE: DNA
<213> ORGANISM: H1N1 influenza A virus

<400> SEQUENCE: 113
cagaatatac atccagtcac aattggaaaa                                       30

<210> SEQ ID NO 114
<211> LENGTH: 30
<212> TYPE: DNA
<213> ORGANISM: H1N1 influenza A virus
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (30)..(30)
<223> OTHER INFORMATION: n is dA modified with FQ.

<400> SEQUENCE: 114
nagaatatac atccagtcac aattggaaan                                       30

<210> SEQ ID NO 115
<211> LENGTH: 30
<212> TYPE: DNA
<213> ORGANISM: H1N1 influenza A virus
<220> FEATURE:
<221> NAME/KEY: misc_feature
<222> LOCATION: (1)..(1)
<223> OTHER INFORMATION: n is dC modified with FAM.
```

```
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (30)..(30)
<223> OTHER INFORMATION: n is dA modified with SpC3.

<400> SEQUENCE: 115
nagaatatac atccagtcac aattggaaan                                           30

<210> SEQ ID NO 116
<211> LENGTH: 30
<212> TYPE: DNA
<213> ORGANISM: H1N1 influenza A virus
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (30)..(30)
<223> OTHER INFORMATION: n is dA modified with FQ.

<400> SEQUENCE: 116
nagaatatac atccagtcac aattggaaan                                           30

<210> SEQ ID NO 117
<211> LENGTH: 30
<212> TYPE: DNA
<213> ORGANISM: H1N1 influenza A virus
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (9)..(10)
<223> OTHER INFORMATION: iBHQ1 is inserted between nucleotide positions
      9 and 10.
<220> FEATURE:
<221> NAME/KEY: misc_feature
<222> LOCATION: (30)..(30)
<223> OTHER INFORMATION: n is dA modified with BHQ1.

<400> SEQUENCE: 117
nagaatatac atccagtcac aattggaaan                                           30

<210> SEQ ID NO 118
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with FAM.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with RQ.
```

```
<400> SEQUENCE: 118
ntggtcaagg tcgcaagctt gctggn                                              26

<210> SEQ ID NO 119
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with MAX.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with FQ.

<400> SEQUENCE: 119
ntggtcaagg tcgcaagctt gctggn                                              26

<210> SEQ ID NO 120
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with MAX.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dt modified with RQ.

<400> SEQUENCE: 120
ntggtcaagg tcgcaagctt gctggn                                              26

<210> SEQ ID NO 121
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with Cy3.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with FQ.

<400> SEQUENCE: 121
ntggtcaagg tcgcaagctt gctggn                                              26

<210> SEQ ID NO 122
<211> LENGTH: 26
<212> TYPE: DNA
<213> ORGANISM: Homo sapiens
<220> FEATURE:
```

```
<221> NAME/KEY: misc_feature
<222> LOCATION: (1)..(1)
<223> OTHER INFORMATION: n is dA modified with Cy3.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with RQ.

<400> SEQUENCE: 122
ntggtcaagg tcgcaagctt gctggn                                        26

<210> SEQ ID NO 123
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with TEX.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with FQ.

<400> SEQUENCE: 123
ntggtcaagg tcgcaagctt gctggn                                        26

<210> SEQ ID NO 124
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with TEX.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with RQ.

<400> SEQUENCE: 124
ntggtcaagg tcgcaagctt gctggn                                        26

<210> SEQ ID NO 125
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with Cy5.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
```

<222> LOCATION: (26)..(26)
<223> OTHER INFORMATION: n is dT modified with FQ.

<400> SEQUENCE: 125
ntggtcaagg tcgcaagctt gctggn        26

<210> SEQ ID NO 126
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with Cy5.
<220> FEATURE:
<221> NAME/KEY: misc_feature
<222> LOCATION: (9)..(10)
<223> OTHER INFORMATION: iFQ is inserted between nucleotide positions 9
      and 10.
<220> FEATURE:
<221> NAME/KEY: misc_feature
<222> LOCATION: (26)..(26)
<223> OTHER INFORMATION: n is dT modified with RQ.

<400> SEQUENCE: 126
ntggtcaagg tcgcaagctt gctggn        26

<210> SEQ ID NO 127
<211> LENGTH: 26
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is dA modified with Cy5.
<220> FEATURE:
<221> NAME/KEY: misc_feature
<222> LOCATION: (11)..(12)
<223> OTHER INFORMATION: iFQ is inserted between nucleotide positions 11
      and 12.
<220> FEATURE:
<221> NAME/KEY: misc_feature
<222> LOCATION: (26)..(26)
<223> OTHER INFORMATION: n is dT modified with RQ.

<400> SEQUENCE: 127
ntggtcaagg tcgcaagctt gctggn        26

<210> SEQ ID NO 128
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 128
cgcgatcaga caaggagtgg gcttcatgga tcgcg        35

<210> SEQ ID NO 129
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 129
ttacatgaag cccactcctt gtctatc        27

<210> SEQ ID NO 130

```
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (35)..(35)
<223> OTHER INFORMATION: n is dG modified with Dabcyl.

<400> SEQUENCE: 130
ngcgatcaga caaggagtgg gcttcatgga tcgcn                              35

<210> SEQ ID NO 131
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (35)..(35)
<223> OTHER INFORMATION: n is dG modified with BHQ-1.

<400> SEQUENCE: 131
ngcgatcaga caaggagtgg gcttcatgga tcgcn                              35

<210> SEQ ID NO 132
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (1)..(1)
<223> OTHER INFORMATION: n is dG modified with FQ.
<220> FEATURE:
<221> NAME/KEY: misc_feature
<222> LOCATION: (35)..(35)
<223> OTHER INFORMATION: n is a, c, g, or t

<400> SEQUENCE: 132
ngcgatcaga caaggagtgg gcttcatgga tcgcn                              35

<210> SEQ ID NO 133
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (35)..(35)
<223> OTHER INFORMATION: n is dG modified with FQ.
<220> FEATURE:
<221> NAME/KEY: misc_feature
```

```
<222> LOCATION: (35)..(35)
<223> OTHER INFORMATION: n is dG modified with FQ/FQ.

<400> SEQUENCE: 133
ngcgatcaga caaggagtgg gcttcatgga tcgcn                              35

<210> SEQ ID NO 134
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (34)..(35)
<223> OTHER INFORMATION: iFQ is inserted between nucleotide positions 34
      and 35.
<220> FEATURE:
<221> NAME/KEY: misc_feature
<222> LOCATION: (35)..(35)
<223> OTHER INFORMATION: n is dG modified with FQ.

<400> SEQUENCE: 134
ngcgatcaga caaggagtgg gcttcatgga tcgcn                              35

<210> SEQ ID NO 135
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (33)..(34)
<223> OTHER INFORMATION: iFQ is inserted between nucleotide positions 33
      and 34.
<220> FEATURE:
<221> NAME/KEY: misc_feature
<222> LOCATION: (35)..(35)
<223> OTHER INFORMATION: n is dG modified with FQ.

<400> SEQUENCE: 135
ngcgatcaga caaggagtgg gcttcatgga tcgcn                              35

<210> SEQ ID NO 136
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (32)..(33)
<223> OTHER INFORMATION: iFQ is inserted between nucelotide positions 32
      and 33.
<220> FEATURE:
<221> NAME/KEY: misc_feature
<222> LOCATION: (35)..(35)
<223> OTHER INFORMATION: n is dG modified with FQ.

<400> SEQUENCE: 136
```
ngcgatcaga caaggagtgg gcttcatgga tcgcn					35

<210> SEQ ID NO 137
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (31)..(32)
<223> OTHER INFORMATION: iFQ is inserted between nucelotide positions 31
      and 32.
<220> FEATURE:
<221> NAME/KEY: misc_feature
<222> LOCATION: (35)..(35)
<223> OTHER INFORMATION: n is dG modified with FQ.

<400> SEQUENCE: 137
ngcgatcaga caaggagtgg gcttcatgga tcgcn					35

<210> SEQ ID NO 138
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (30)..(31)
<223> OTHER INFORMATION: iFQ is inserted between nucleotide positions 30
      and 31.
<220> FEATURE:
<221> NAME/KEY: misc_feature
<222> LOCATION: (35)..(35)
<223> OTHER INFORMATION: n is dG modified with FQ.

<400> SEQUENCE: 138
ngcgatcaga caaggagtgg gcttcatgga tcgcn					35

<210> SEQ ID NO 139
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (29)..(30)
<223> OTHER INFORMATION: iFQ is inserted between nucleotide positions 29
      and 30.
<220> FEATURE:
<221> NAME/KEY: misc_feature
<222> LOCATION: (35)..(35)
<223> OTHER INFORMATION: n is dG modified with FQ.

<400> SEQUENCE: 139
ngcgatcaga caaggagtgg gcttcatgga tcgcn					35

```
<210> SEQ ID NO 140
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (35)..(35)
<223> OTHER INFORMATION: n is dG modified with RQ.

<400> SEQUENCE: 140
ngcgatcaga caaggagtgg gcttcatgga tcgcn                              35

<210> SEQ ID NO 141
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (35)..(35)
<223> OTHER INFORMATION: n is dG modified with FQ/RQ.

<400> SEQUENCE: 141
ngcgatcaga caaggagtgg gcttcatgga tcgcn                              35

<210> SEQ ID NO 142
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (34)..(35)
<223> OTHER INFORMATION: iFQ is inserted between nucleotide positions 34
      and 35.
<220> FEATURE:
<221> NAME/KEY: misc_feature
<222> LOCATION: (35)..(35)
<223> OTHER INFORMATION: n is dG modified with RQ.

<400> SEQUENCE: 142
ngcgatcaga caaggagtgg gcttcatgga tcgcn                              35

<210> SEQ ID NO 143
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (33)..(34)
<223> OTHER INFORMATION: iFQ is inserted between nucleotide positions 33
``` and 34.
<220> FEATURE:
<221> NAME/KEY: misc_feature
<222> LOCATION: (35)..(35)
<223> OTHER INFORMATION: n is dG modified with RQ.

<400> SEQUENCE: 143
ngcgatcaga caaggagtgg gcttcatgga tcgcn                                    35

<210> SEQ ID NO 144
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (32)..(33)
<223> OTHER INFORMATION: iFQ is inserted between nucleotide positions 32
        and 33.
<220> FEATURE:
<221> NAME/KEY: misc_feature
<222> LOCATION: (35)..(35)
<223> OTHER INFORMATION: n is dG modified with RQ.

<400> SEQUENCE: 144
ngcgatcaga caaggagtgg gcttcatgga tcgcn                                    35

<210> SEQ ID NO 145
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (31)..(32)
<223> OTHER INFORMATION: iFQ is inserted between nucleotide positions 31
        and 32.
<220> FEATURE:
<221> NAME/KEY: misc_feature
<222> LOCATION: (35)..(35)
<223> OTHER INFORMATION: n is dG modified with RQ.

<400> SEQUENCE: 145
ngcgatcaga caaggagtgg gcttcatgga tcgcn                                    35

<210> SEQ ID NO 146
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (30)..(31)
<223> OTHER INFORMATION: iFQ is inserted between nucleotide positions 30
        and 31.
<220> FEATURE:
<221> NAME/KEY: misc_feature
<222> LOCATION: (35)..(35)

```
<223> OTHER INFORMATION: n is dG modified with RQ.

<400> SEQUENCE: 146
ngcgatcaga caaggagtgg gcttcatgga tcgcn                              35

<210> SEQ ID NO 147
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: n is dC modified with FAM.
<220> FEATURE:
<221> NAME/KEY: misc_feature
<222> LOCATION: (29)..(30)
<223> OTHER INFORMATION: iFQ is inserted between nucleotide positions 29
      and 30.
<220> FEATURE:
<221> NAME/KEY: misc_feature
<222> LOCATION: (35)..(35)
<223> OTHER INFORMATION: n is dG modified with RQ.

<400> SEQUENCE: 147
ngcgatcaga caaggagtgg gcttcatgga tcgcn                              35
```

METHODS FOR ENHANCING NUCLEIC ACID HYBRIDIZATION

CROSS-REFERENCE TO RELATED APPLICATIONS

This patent application is a divisional of U.S. patent application Ser. No. 13/073,866 filed Mar. 28, 2011, which claims priority to U.S. Provisional Patent Application No. 61/318,043 filed Mar. 26, 2010. These applications are incorporated herein by reference in their entirety.

SEQUENCE LISTING

The sequence listing is filed with the application in electronic format only and is incorporated by reference herein. The sequence listing text file "ASFILED_Sequence_US00" was created on Mar. 25, 2011, and is 49,585 bytes in size.

FIELD OF THE DISCLOSURE

This disclosure pertains to novel oligonucleotide compounds with improved hybridization properties. Methods and reagents are provided which allow internal labeling of oligonucleotides by insertion of labels between adjacent residues without destabilizing the duplex. Because the nucleotide bases are not modified, such labeling groups can be introduced into any sequence. In some embodiments, such modifications increase duplex stability. In some embodiments, the labeling group is a fluorescence quencher. The disclosure further relates to the design of fluorescently labeled oligonucleotide probes with multiple quenching dyes capable of very efficient fluorescence quenching over a broad spectral range.

BACKGROUND

Fluorescent energy transfer probes are an important tool in genetic analysis. These probes, also known as dual-labeled probes (DLPs) or self-quenching probes, are generally comprised of a fluorescent donor (a fluorophore) and a quencher linked to an oligonucleotide. This basic design, wherein a signal change is detected once the probe hybridizes to its intended target, is used in a variety of biological applications.

One method for detecting hybridization using fluorophores and quenchers is to link fluorescent donors and quenchers to a single oligonucleotide such that there is a detectable difference in fluorescence when the oligonucleotide is unhybridized as compared to when it is hybridized to its complementary sequence. In so-called molecular beacons, a partially self-complementary oligonucleotide is designed to form a hairpin and is labeled with a fluorescent donor at one end of the molecule and a quencher at the other end (U.S. Pat. No. 5,925,517). Intramolecular annealing to form the hairpin brings the donor and quencher into close proximity for fluorescent quenching to occur. Intermolecular annealing of such an oligonucleotide to a target sequence disrupts the hairpin, which increases the distance between the donor and quencher and results in a detectable increase in the fluorescent signal of the donor.

Oligonucleotides are not required to form a hairpin structure for this method to work efficiently. The fluorophore and quencher can be placed on an oligonucleotide such that when it is unhybridized and in a random coil conformation, the quencher is able to quench fluorescence from the fluorophore (U.S. Pat. No. 5,538,848). Once the oligonucleotide hybridizes to a complementary nucleotide sequence it becomes more extended and the distance between the fluorophore and quencher is increased, resulting in reduced quenching and increased fluorescence.

Oligonucleotides labeled in a similar manner can also be used to monitor the kinetics of PCR amplification. In one version of this method, commonly known as a 5'-nuclease cleavage or hydrolysis assay, an oligonucleotide probe is designed to hybridize to the target sequence on the 3' side ("downstream") of one of the amplification primers. During PCR, the 5'-3' exonuclease activity of the DNA polymerase digests the 5' end of the probe thereby separating the fluorophore from the quencher. The fluorescence intensity of the sample increases as an increasing number of probe molecules are digested during the course of amplification (U.S. Pat. No. 5,210,015).

DLPs find use in other molecular/cellular biology and diagnostic assays, such as in end-point PCR, in situ hybridizations, in vivo DNA and RNA species detection, single nucleotide polymorphism (SNPs) analysis, enzyme assays, and in vivo and in vitro whole cell assays (see Dirks and Tanke, *Biotechniques* 2006, 40:489-486; Bustin, *Journal of Molecular Endocrinology* 2002, 29:23-39; Mackay, *Clin Microbiol Infect*, 2004, 10:190-212).

In one mechanism of fluorescence quenching termed ground state quenching, the fluorophore and the quencher associate to form a ground state complex which is not fluorescent. For ground state quenching to occur there need not be spectral overlap between the fluorophore and the quencher.

The most common mechanism of fluorescent quenching is fluorescence resonance energy transfer (FRET). In FRET, energy transfer occurs through space by dipolar coupling between the fluorophore and quencher and requires that there be overlap between the emission spectrum of the fluorescent donor and the absorbance spectrum of the quencher. This requirement complicates the design of probes that utilize FRET because quenchers are limited in their effective wavelength range. For example, the quencher known as BHQ-1, which absorbs light in the wavelength range of about 500-550 nm, quenches fluorescent light emitted by fluorescein, which fluoresces maximally at about 520 nm, but is of limited utility for Texas Red (emission maximum=615) or Cy5 (emission maximum=670). In contrast, the quencher BHQ-3, which absorbs light in the wavelength range of about 650-700 nm is almost completely ineffective at quenching fluorescein but is effective at quenching Cy5. In general, the number of quenchers that are known to be capable of quenching the fluorescence of any given fluorophore is limited.

Although fluorescent dyes themselves can be employed to quench fluorescence from other dyes, preferred quenchers will not fluoresce (or minimally fluoresce) so that background fluorescence is minimized. These quenchers are commonly referred to as dark quenchers. Dark quenchers allow for an increased signal to noise ratio in assays that employ DLPs, resulting in increased sensitivity. In addition, the lack of secondary fluorescence facilitates the use of additional fluorophores in multiplexed assay formats which utilize multiple distinct probes each containing a different fluorophore. If a quencher emitted light in a certain region, then additional probes could not bear fluorophores that emit light in that same region.

A number of factors are considered in designing a self-quenching probe. These include the ease of synthesis, the compatibility of the fluorophore and quencher, duplex stability, and the specificity of the probe in hybridizing to the intended target.

Duplex stability between complementary nucleic acid molecules is frequently expressed as the "melting temperature", $T_m$, of the duplex. Roughly speaking, the $T_m$ indicates the temperature at which a duplex nucleic acid dissociates into two single strands. Nucleic acid hybridization is generally performed at a temperature slightly below the $T_m$, so that hybridization between a probe or primer and its target nucleic acid is optimized, while minimizing non-specific hybridization of the probe or primer to other, non-target nucleic acids. Duplex stability and $T_m$ are also important in applications, such as PCR, where thermocycling may be involved. During such thermocycling melting steps, it is important that the sample temperature be raised sufficiently above the $T_m$ so that duplexes of the target nucleic acid and its complement are dissociated. In subsequent steps of reannealing, however, the temperature must be brought sufficiently below the $T_m$ that duplexes of the target nucleic acid and primer are able to form, while still remaining high enough to avoid non-specific hybridization events. For a general discussion, see Rychlik et al., *Nucleic Acids Research* 1990, 18:6409-6412.

Shorter oligonucleotides can help increase the specificity of a primer or probe, allowing for the discrimination of even a single mismatch between the probe and a potential complementary target. The shorter the oligonucleotide, the greater the effect of a single-base mismatch on duplex stability. However, the disadvantage of using such short oligonucleotides is that they hybridize weakly, even to a perfectly complementary sequence, and thus must be used at lower temperatures, which are unfavorable for reactions that use thermal stable enzymes, such as PCR. Certain modified nucleosides such as locked nucleic acids (LNAs) (U.S. Pat. No. 7,060,809) and C5-propynyl pyrimidines (U.S. Pat. No. 5,484,908) can be incorporated into oligonucleotides to increase duplex stability. Many nucleoside analogs, however, especially those having bulkier substituents attached to the base, are destabilizing. For example, fluorescein-dT can destabilize a duplex by up to 4° C. (Bioorganic & Medicinal Chemistry Letters, 13:2785-2788 2003).

Modified nucleosides employed to increase Tm are typically placed internally within an oligonucleotide sequence replacing a natural base. In contrast, non-nucleoside substituents when introduced internally within an oligonucleotide, either as a replacement for a base or as an insertion between bases, generally interfere with hybridization. For example, insertion of an abasic fluorescein group into an oligonucleotide has been observed to destabilize a duplex by 2-4° C. (DNA Seq. 4:135-141, 1993).

There are several classes of compounds that are known to increase binding affinity between complementary nucleic acid strands. One class is major groove binders, which includes proteins or ligands that bind to the major groove (the wider groove around a DNA helix). A second class, minor groove binders (MGBs), include non-covalently bound and covalently bound compounds. Because the minor groove of a helix is narrower in A-T rich regions, some noncovalently bound MBGs recognize the shape of the helix and preferably bind to specific sequence regions. For example, netropsin and distamycin preferably bind to A-T regions (see Bailly and Henichart, ACS, vol. 2, 379-393 (1991). Covalently bound MGBs (U.S. Pat. No. 6,084,102) are typically linked to the 5' or 3' end of oligonucleotides (U.S. Pat. App. 2009/0259030) and are known to increase binding affinity and allow for shorter length probes.

A third class, intercalators, are generally flat polycyclic compounds, examples being acridine or lipticine derivatives (see U.S. Pat. No. 4,835,263). Intercalating compounds stabilize a duplex by fitting in between the bases of the nucleic acid monomers. They can be covalently or noncovalently bound. Some minor groove compounds, such as 4',6-diamidino-2-phenylindole (DAPI), also intercalate.

Another group of compounds, capping reagents, are terminally attached compounds that favor Watson-Crick duplexes by stacking on the terminal base pair (Dogan, Z. et al., J. Am. Chem. Soc. 2004, 126, 4762-4763). Such groups include stilbene derivatives (Wu, T, et al., J. Am. Chem. Soc. 1995, 117, 8785-8792) and pyrenylmethylpyrrolindol (Narayanan, S. et al., Nucleic Acids Res. 2004, 32, 2901-2911).

The efficiency of quenching through FRET is extremely sensitive to the distance between the fluorophore and quencher ($R_{FQ}$), varying with the reciprocal of $R_{FQ}$ to the sixth power. Maximally efficient quenching minimizes background fluorescence and improves the sensitivity of the 5'-nuclease assay and other hybridization assays in which DLPs are used. Generally, for ease of synthesis and to avoid disruption of hybridization of the probe to the target sequence, the dye and quencher are attached to the ends of the oligonucleotide. For the 5'-nuclease assay, the most common configuration is to attach the dye at the 5'-end of the oligonucleotide and the quencher at the 3'-end. DLPs used in the 5'-nuclease assay are typically 25 to 30 bases in length. Even with the use of $T_m$ enhancing modifications, such as LNA bases or a minor groove binder, probe length is still usually 14 to 18 bases. Any method that permits placement of the fluorophore and quencher in closer proximity within a probe without destabilizing the duplex formed between the probe and its target nucleic acid will improve quencher efficiency and enhance the performance of the probe.

BRIEF SUMMARY

This disclosure provides various compositions comprising oligonucleotides having modifying compounds placed internally within the oligonucleotide sequence between nucleotides. Even though these modifying compounds are inserted between adjacent nucleotides (as opposed to being substituted for one of the nucleotides), some of the modified oligonucleotides surprisingly form equally stable, or even more stable, duplexes with their complimentary oligonucleotide sequences as compared to the stability of the duplex formed between the unmodified oligonucleotide and the complimentary oligonucleotide. The modifying groups may include a variety of labels, including but not limited to fluorescence quenchers that enable the design of DLPs with very high quenching efficiency. Because the labeling group is not a modified base, the same modifying compound can be inserted into any position within any oligonucleotide sequence. This disclosure also provides methods for using and making the oligonucleotide compositions.

The compositions of the present disclosure each comprise an oligonucleotide having the general structure 5'-$Y_1$-$L_1$-X-$L_2$-$Y_2$-3', where:

$Y_1$ comprises a sequence of one or more DNA and/or RNA nucleotides, including a first nucleotide $N_1$ having a 3' phosphate covalently linked to $L_1$;

$Y_2$ comprises a sequence of one or more DNA and/or RNA nucleotides, including a second nucleotide $N_2$ having a 5' phosphate covalently linked to $L_2$;

$L_1$ and $L_2$ each independently are a direct bond or a $C_1$-$C_7$ alkyl, alkynyl, alkenyl, heteroalkyl, substituted alkyl, aryl, heteroaryl, substituted aryl, cycloalkyl, alkylaryl, or alkoxyl group;

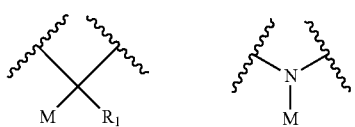

X is or;
R$_1$ is a hydrogen or a C$_1$-C$_8$ alkyl; and
M is a label.

These oligonucleotides may include any desired number of nucleotides, but preferably include 10-50 nucleotides, and even more preferably include 15-35 nucleotides. In some embodiments, L$_1$ and L$_2$ each may be a C$_1$-C$_7$ alkyl, and preferably a C$_2$ alkyl. The 3' phosphate that is covalently linked to L$_1$, and the 5' phosphate that is covalently linked to L$_2$, each independently may be a phosphodiester, a phosphothioate, a phosphodithioate, a methyl phosphonate, a phosphoramidate, a phosphoramidite or a phosphotriester.

In some embodiments, Y$_1$ comprises a sequence of four or more DNA and/or RNA nucleotides, Y$_2$ comprises a sequence of four or more DNA and/or RNA nucleotides, M is a first quencher, and the oligonucleotide is adapted to hybridize to a second oligonucleotide having the structure 3'-Y$_3$-Y$_4$-5', where Y$_3$ comprises a sequence of four or more DNA and/or RNA nucleotides, including a third nucleotide N$_3$, Y$_4$ comprises a sequence of four or more DNA and/or RNA nucleotides, including a fourth nucleotide N$_4$ that is directly attached to nucleotide N$_3$. If the first oligonucleotide hybridizes to the second oligonucleotide, then N$_1$ base pairs with N$_3$ and N$_2$ base pairs with N$_4$. to form a duplex having a T$_m$ that is greater than the T$_m$ of a duplex formed between the second oligonuleotide and a third oligonucleotide having the structure 5'-Y$_1$-Y$_2$-3'. In such embodiments, the first oligonucleotide may be labeled with a fluorophore. For example, the fluorophore may be attached to the last nucleotide on the 5' end of the oligonucleotide, and in preferred embodiments, Y$_1$ may comprise a sequence of 8-12 DNA or RNA nucleotides. Compositions comprising the first oligonucleotide also may comprise the second oligonucleotide.

In some embodiments, Y$_1$ comprises a sequence of 8-12 DNA and/or RNA nucleotides, such as a sequence of 10 DNA and/or RNA nucleotides, where the nucleotide on the 5' end of Y$_1$ is labeled with a fluorophore, and M is a quencher.

In some embodiments, M comprises a fused polycyclic aromatic moiety.

In some embodiments, M is:

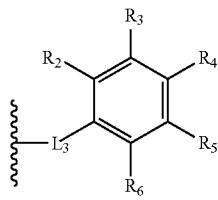

where L$_3$ is a direct bond or a C$_1$-C$_8$ alkyl, alkenyl, alkenyl, heteroalkyl, substituted alkyl, cycloalkyl, or alkoxyl, where R$_2$-R$_6$ each independently are a hydrogen, an alkyl, an alkenyl, a heteroalkyl, a substituted alkyl, an aryl, a heteroaryl, a substituted aryl, a cycloalkyl, an alkylaryl, an alkoxyl, an electron withdrawing group, or an electron donating group, and where one of R$_2$-R$_6$ is —N═N—P, and where P is a fused polycyclic aromatic moiety. Electron withdrawing groups may be selected from the group consisting of —NO$_2$, —SO$_3^-$, —SO$_2^-$, —CN, —NCS, a ketone, an alkoxyl, an ether, a carboxylic acid and a sulfonyl. Electron donating group is selected from the group consisting of an alkoxyl, a heteroalkoxyl, an alkyl, a cycloalkyl, a heteroalkyl, an amino, an alkylamino, or an arylamino.

In some embodiments, M is -L$_4$-P, where L$_4$ is an alkyl, an alkynyl, an alkenyl, a heteroalkyl, a substituted alkyl, or an alkoxyl group, and P is a fused polycyclic aromatic moiety. For example, L$_4$ may be —CH2-O—CH2-CH2-NH— or any other suitable linker.

Various of the oligonucleotides described herein include fused polycyclic aromatic moieties P. In some embodiments, P is

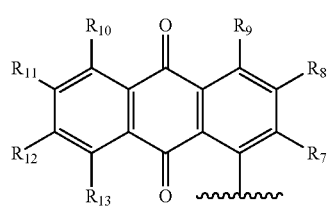

where R$_7$-R$_9$ each independently are a hydrogen, an alkoxyl, an alkyl, an alkylamino, an arylamino, a cycloalkyl, a heteroalkoxyl, a heteroalkyl, or an amino, and R$_{10}$-R$_{13}$ each independently are a hydrogen, a nitro, a cyano, a carboxylate, a sulfonyl, a sulfamoyl, an alkenyl, an alkynyl, an amino, an aryl, a heteroaryl, a biaryl, a bialkenyl, a bialkynyl, an alkoxycarbonyl or a carbamoyl. In preferred embodiments, R$_9$ is

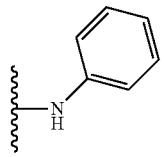 [SMILES: *Nc1ccccc1]

In some embodiments, P is

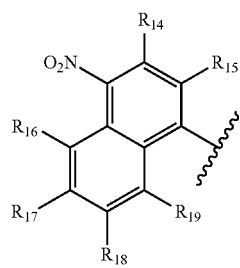

where R$_{14}$-R$_{19}$ each independently are a hydrogen, an alkyl, a heteroalkyl, an aryl, a heteroaryl, an electron withdrawing group, or a five or six membered ring structure formed from the R1, R2 pair, the R$_3$, R$_4$ pair, the R$_4$, R$_5$ pair, or the R$_5$, R$_6$ pair.

Some of the oligonucleotides disclosed herein include a fluorophore, which may include, but is not limited to, 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX); 1-dimethylaminonaphthyl-5-sulfonate, 1-anilino-8-naphthalene sulfonate, 2-p-toluidinyl-6-naphthalene sulfonate, 5-(2'-aminoethyl)aminonaphthalene-1-sulfonic acid (EDANS), a coumarin dye, an acridine dye, indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyloxacarbocyanine (CyA); 1H,5H,11H,15H-Xantheno[2,3,4-ij:5,6,7-i'j']diquinolizin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red), a BODIPY™ dye, benzoxaazole, stilbene and pyrene. In some embodiments, the fluorophore may be attached to the 5' end, such as to the phosphate at the 5' end of the oligonucleotide.

Some of the oligonucleotides disclosed herein include more than one quencher, such as a first internal quencher (described above) and a second quencher. The second quencher may include, but is not limited to dabcyl, Eclipse® quencher, BHQ1, BHQ2 and BHQ3, Iowa Black® FQ, Iowa Black® RQ-n1 or Iowa Black® RQ-n2.

This disclosure also provides methods for using and making the oligonucleotide compositions. Methods for use may include methods for detecting target nucleic acids within a sample. For example, such methods may include contacting the sample with an oligonucleotide adapted to hybridize to the target nucleic acid, where the oligonucleotide includes an internal quencher and a fluorophore, and where the fluorescence of the fluorophore is reduced by fluorescence resonance energy transfer to the quencher or by ground state quenching by the quencher when the oligonucleotide is not hybridized to the second oligonucleotide, and detecting an increase in fluorescence indicating the presence of the second oligonucleotide in the sample.

BRIEF DESCRIPTION OF THE DRAWINGS

FIGS. 7A and 7B are amplification plots for the fluorescein (emission 520 nm) reporter dye probes, wherein the baseline plots are shown in FIG. 7A and baseline normalized plots are shown in FIG. 7B.

DETAILED DESCRIPTION

Figure 1A:
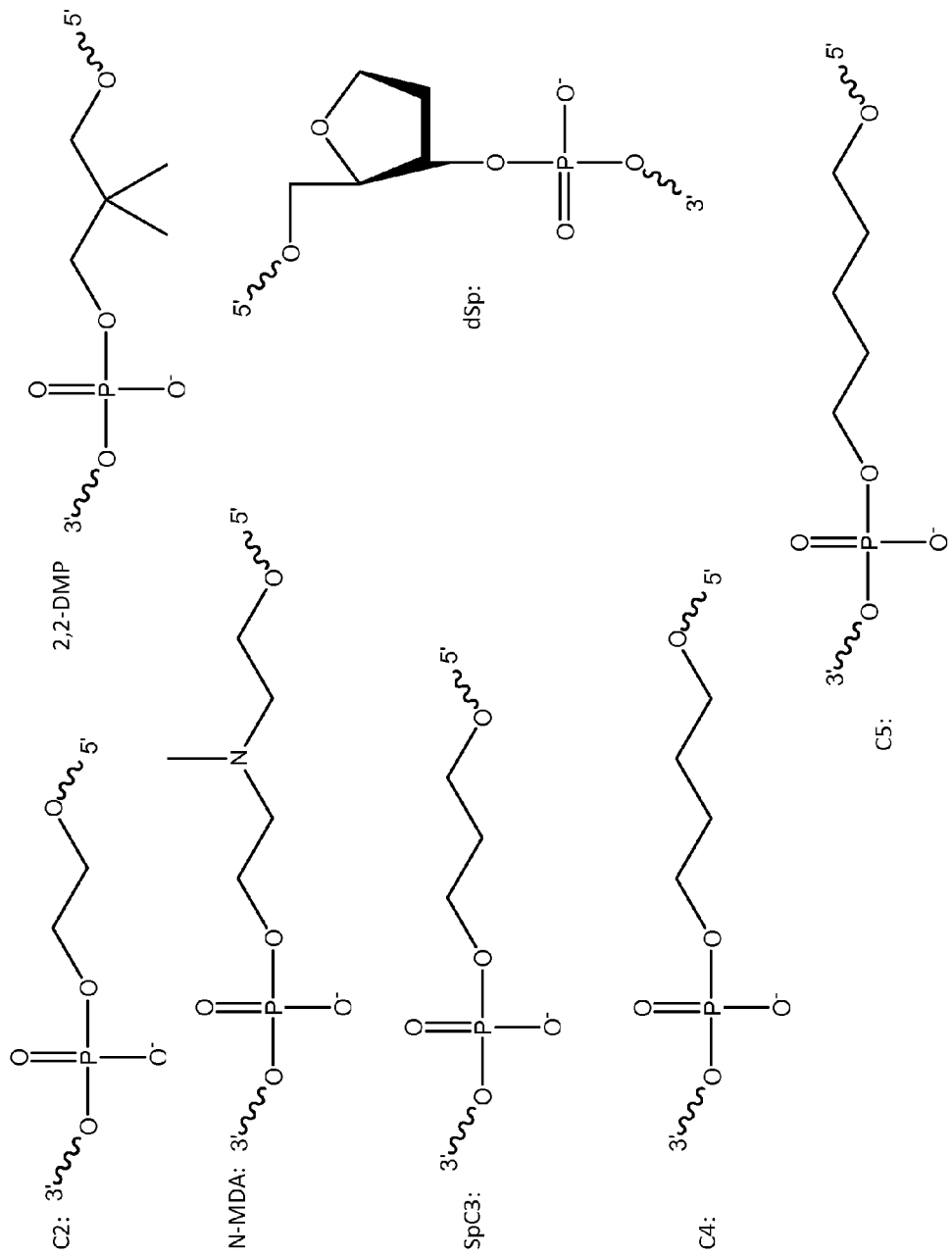
FIGS. 1A, 1B and 1C are structures of modified oligonucleotides tested for their effects on the stability of the duplex formed between the modified oligonucleotide and its complimentary oligonucleotide. The modified oligonucleotides contain various modification compounds inserted between, and attached to the 3' and 5' phosphates of adjacent nucleotides.
Figure 1A:
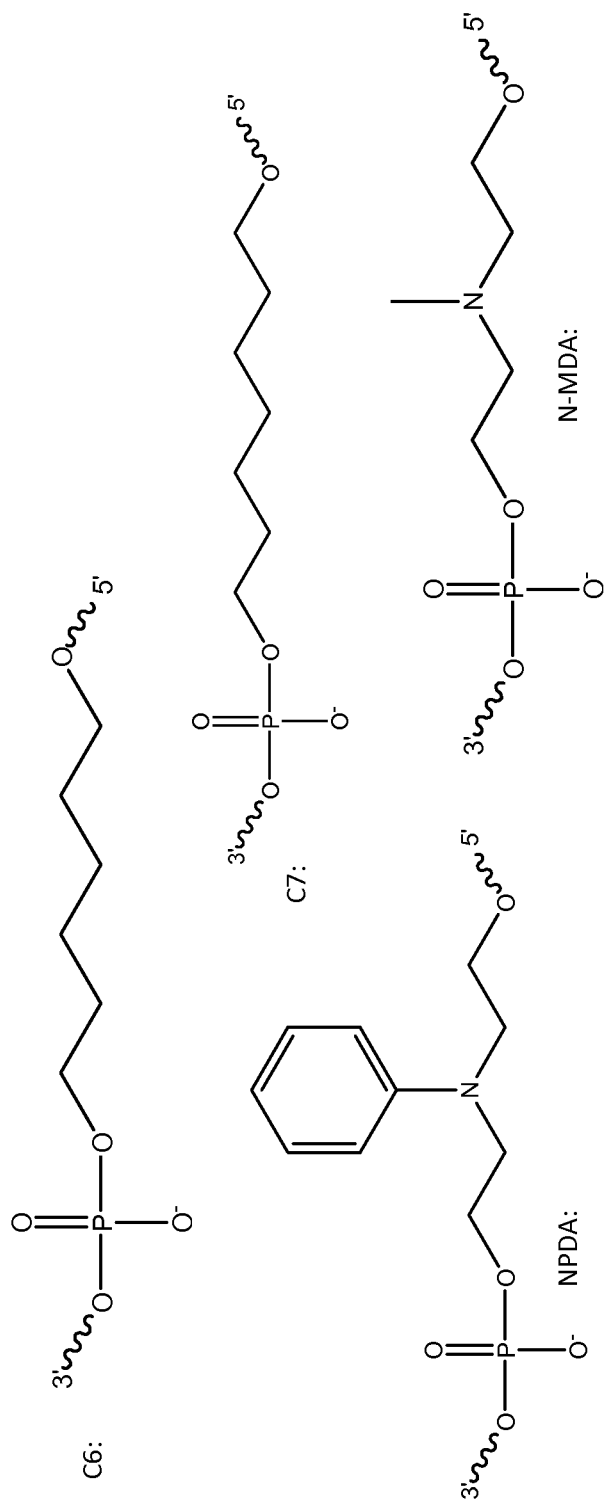

This disclosure provides various compositions comprising oligonucleotides having modifying compounds placed internally within the oligonucleotide sequence between nucleotides. Some of the he modified oligonucleotides surprisingly form equally stable, or even more stable, duplexes with their complimentary oligonucleotide sequences as compared to the stability of the duplex formed between the unmodified oligonucleotide and the complimentary oligonucleotide. The mechanism by which some modifying compounds confer stability to a duplex is unknown. It is particularly surprising and unexpected that modifications of adjacent residues within an oligonucleotide with these compounds should increase duplex stability given the close proximity of the two phosphate groups on either side of reagent when in the double helix. The modifying groups may include a variety of labels, including but not limited to fluorescence quenchers that enable the design of DLPs with very high quenching efficiency. Because the labeling group is not a modified base, the same modifying compound can be inserted into any position within any oligonucleotide sequence. This disclosure also provides methods for using and making the oligonucleotide compositions.

The compositions of the present disclosure each comprise an oligonucleotide having the general structure 5'-$Y_1$-$L_1$-X-$L_2$-$Y_2$-3', where:

$Y_1$ comprises a sequence of one or more DNA and/or RNA nucleotides, including a first nucleotide $N_1$ having a 3' phosphate covalently linked to $L_1$;

$Y_2$ comprises a sequence of one or more DNA and/or RNA nucleotides, including a second nucleotide $N_2$ having a 5' phosphate covalently linked to $L_2$;

$L_1$ and $L_2$ each independently are a direct bond or a $C_1$-$C_7$ alkyl, alkynyl, alkenyl, heteroalkyl, substituted alkyl, aryl, heteroaryl, substituted aryl, cycloalkyl, alkylaryl, or alkoxyl group;

X is

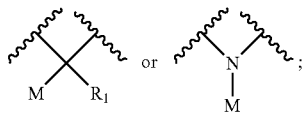

$R_1$ is a hydrogen or a $C_1$-$C_8$ alkyl; and
M is a label.

FIG. 1 provides a non-exclusive exemplary list of modified oligonucleotides having a modifying compound inserted between adjacent nucleotides. These modified oligonucleotides may include any desired number of nucleotides, but preferably include 10-50 nucleotides, and even more preferably include 15-35 nucleotides. Moreover, depending on the application, the labeled oligonucleotide can be DNA, RNA or a chimeric oligonucleotide containing both DNA and RNA residues. Modified nucleosides such as LNA bases, 2'-O-methyl RNA and purine and pyrimidines analogs also may be included within the sequence. For use as a probe or primer, the length of the oligonucleotide is typically between 15 and 35 residues. Because the label is inserted between adjacent residues (as opposed to being a label attached to a particular nucleotide) the same modifying compound may be used to label essentially any sequence.

In some embodiments, $L_1$ and $L_2$ each may be a $C_1$-$C_7$ alkyl, and preferably a $C_2$ alkyl. An increase in the stability of the duplex formed upon hybridization of the modified oligonucleotides to its target sequence can be achieved (see Example 1).

The 3' phosphate that is covalently linked to $L_1$, and the 5' phosphate that is covalently linked to $L_2$, each independently may be a phosphodiester, a phosphothioate, a phosphodithioate, a methyl phosphonate, a phosphoramidate, a phosphoramidite or a phosphotriester. A modified, neutrally charged phosphorous group could be used that would confer even grater stability.

In some embodiments, $Y_1$ comprises a sequence of four or more DNA and/or RNA nucleotides, $Y_2$ comprises a sequence of four or more DNA and/or RNA nucleotides, M is a first quencher, and the oligonucleotide is adapted to hybridize to a second oligonucleotide having the structure 3'-$Y_3$-$Y_4$-5', where $Y_3$ comprises a sequence of four or more DNA and/or RNA nucleotides, including a third nucleotide $N_3$, $Y_4$ comprises a sequence of four or more DNA and/or RNA nucleotides, including a fourth nucleotide $N_4$ that is directly attached to nucleotide $N_3$. If the first oligonucleotide hybridizes to the second oligonucleotide, then $N_1$ base pairs with $N_3$ and $N_2$ base pairs with $N_4$. to form a duplex having a $T_m$ that is greater than the $T_m$ of a duplex formed between the second oligonuleotide and a third oligonucleotide having the structure 5'-$Y_1$-$Y_2$-3'. In such embodiments, the first oligonucleotide may be labeled with a fluorophore. For example, the fluorophore may be attached to the last nucleotide on the 5' end of the oligonucleotide, and in preferred embodiments, $Y_1$ may comprise a sequence of 8-12 DNA or RNA nucleotides for reasons discussed below. Compositions comprising the first oligonucleotide also may comprise the second oligonucleotide.

This disclosure also provides optimized positioning of a quencher relative to a fluorophore in a DLP. In some embodiments, the fluorophore may be attached to the nucleotide at the 5'-end of the oligonucleotide (e.g., to the 5' phosphate) and the quencher may be placed internally within the sequence between about 8 and 12 bases from the fluorophore, such as about 10 bases from the fluorophore (see Example 3). As such, in some embodiments, $Y_1$ comprises a sequence of 8-12 DNA and/or RNA nucleotides, such as a sequence of 10 DNA and/or RNA nucleotides, where the nucleotide on the 5' end of $Y_1$ is labeled with a fluorophore, and M is a quencher.

In some embodiments, M comprises a fused polycyclic aromatic moiety.

In some embodiments, M is:

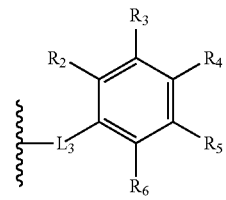

where $L_3$ may be a direct bond or a $C_1$-$C_8$ alkyl, alkenyl, alkenyl, heteroalkyl, substituted alkyl, cycloalkyl, or alkoxyl, where $R_2$-$R_6$ each independently may be a hydrogen, an alkyl, an alkenyl, a heteroalkyl, a substituted alkyl, an aryl, a heteroaryl, a substituted aryl, a cycloalkyl, an alkylaryl, an alkoxyl, a ligand (e.g., amino acids, peptides, antibodies, fluorophores, biotin, enzyme conjugates, vitamins, steroids and other lipids, carbohydrates, digoxigenin and other haptens, etc.), an electron withdrawing group, or an electron donating group, and where one of $R_2$-$R_6$ is —N=N—P, where P is a fused polycyclic aromatic moiety. Electron withdrawing groups may be selected from the group consisting of —$NO_2$, —$SO_3$, —$SO_2^-$, —CN, —NCS, a ketone, an alkoxyl, an ether, a carboxylic acid and a sulfonyl. Electron donating groups may be selected from the group consisting of an alkoxyl, a heteroalkoxyl, an alkyl, a cycloalkyl, a heteroalkyl, an amino, an alkylamino, or an arylamino.

In some embodiments, M is -$L_4$-P, where $L_4$ may be an alkyl, an alkynyl, an alkenyl, a heteroalkyl, a substituted alkyl, or an alkoxyl group, and P is a fused polycyclic aromatic moiety. For example, $L_4$ may be —CH2-O—CH2-CH2-NH— or any other suitable linker.

Various of the oligonucleotides described herein include fused polycyclic aromatic moieties P. In some embodiments, P may be an anthraquinone quencher having the following formula

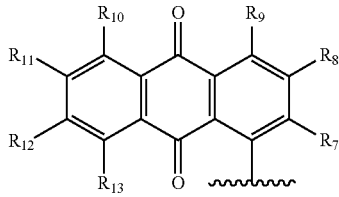

where $R_7$-$R_9$ each independently are a hydrogen, an alkoxyl, an alkyl, an alkylamino, an arylamino, a cycloalkyl, a heteroalkoxyl, a heteroalkyl, or an amino, and $R_{10}$-$R_{13}$ each independently are a hydrogen, a nitro, a cyano, a carboxylate, a sulfonyl, a sulfamoyl, an alkenyl, an alkynyl, an amino, an aryl, a heteroaryl, a biaryl, a bialkenyl, a bialkynyl, an alkoxycarbonyl or a carbamoyl. In preferred embodiments, $R_9$ is

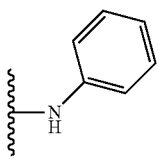 [SMILES: *Nc1ccccc1]

In some embodiments, P may be an azo quencher having the following formula

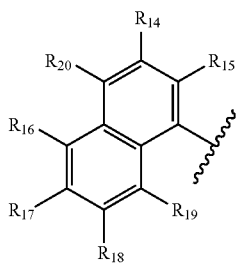

where $R_{14}$-$R_{19}$ each independently may be a hydrogen, an alkyl, a heteroalkyl, an aryl, a heteroaryl, an electron withdrawing group, an electron donating group, or a five or six membered ring structure formed from the R1, R2 pair, the $R_3$, $R_4$ pair, the $R_4$, $R_5$ pair, or the $R_5$, $R_6$ pair, and where $R_{20}$ preferably is an electron withdrawing group, and most preferably —$NO_2$.

Some of the oligonucleotides disclosed herein include a fluorophore, which may include, but is not limited to, 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX); 1-dimethylaminonaphthyl-5-sulfonate, 1-anilino-8-naphthalene sulfonate, 2-p-toluidinyl-6-naphthalene sulfonate, 5-(2'-aminoethyl)aminonaphthalene-1-sulfonic acid (EDANS), a coumarin dye, an acridine dye, indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyloxacarbocyanine (CyA); 1H,5H,11H,15H-Xantheno[2,3,4-ij:5,6,7-i'j']diquinolizin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red), a BODIPY™ dye, benzoxaazole, stilbene and pyrene. In some embodiments, the fluorophore may be attached to the 5' end, such as to the phosphate at the 5' end of the oligonucleotide.

Some of the oligonucleotides disclosed herein may include more than one quencher, such as a first internal quencher (described above) and a second quencher. The second quencher may be placed internally or placed at a terminal end of the oligonucleotide. The second quencher may include, but is not limited to, an azo quencher and an anthraquinone quencher, although any quencher may be used. Examples of azo quenchers include, but are not limited to, the azo quencher shown above, dabcyl, Eclipse® quencher, BHQ1, BHQ2 and BHQ3. Examples of anthraquinone quenchers include, but are not limited to, the anthraquinone quencher shown above, Iowa Black® FQ, Iowa Black® RQ-n1 or Iowa Black® RQ-n2 (see, e.g., Laikhter et al., U.S. Patent App. 2004/0110308). Attachment of multiple quenchers to a probe not only can enhance quenching efficiency but also can provide effective quenching of various fluorophores that fluoresce over a broad spectral range (see Example 7).

The compositions of the present disclosure may be used in various assays for detecting target nucleic acids within a sample. Such methods may include contacting the sample with an oligonucleotide adapted to hybridize to the target nucleic acid, where the oligonucleotide includes an internal quencher and a fluorophore, and where the fluorescence of the fluorophore is reduced by fluorescence resonance energy transfer to the quencher and/or by ground state quenching by the quencher when the oligonucleotide is not hybridized to the second oligonucleotide, and detecting an increase in fluorescence indicating the presence of the second oligonucleotide in the sample. In some assays, such as the 5'-nuclease hydrolysis assay, the increase in fluorescence arises from cleavage of the labeled oligonucleotide. In some assays, the oligonucleotide forms a random-coil conformation when the oligonucleotide is unhybridized, such that the fluorescence of the fluorophore is reduced. In some assays, the oligonucleotide comprises a self-complimentary sequence, and the quencher and fluorophore are attached to the oligonucleotide such that the fluorescence of the fluorophore is quenched by the quencher when the nucleic acid polymer undergoes intramolecular base pairing. These assays have many applications, including, but not limited to, monitoring PCR reactions, where synthesis of the PCR product results in an increase in fluorescence.

Function of dual-labeled probes in the 5'-nuclease hydrolysis assay requires that the fluorophore be effectively quenched by the quencher and also requires that the chemical modifiers employed (dye and quencher) do not interfere with nuclease cleavage. If cleavage is prevented or rendered inefficient by the presence of the chemical modifications, then fluorophore and quencher remain linked during PCR cycles and no detectable signal is generated. The chemical compositions disclosed herein function to efficiently quench the fluorophore and are compatible with probe hydrolysis using 5'-nuclease positive DNA polymerases, like Taq DNA polymerase. The best results are obtained when the internal quencher is positioned as close to the fluorophore as possible (to maximize quenching) yet still permits efficient cleavage of the nucleic acid bases between the dye and quencher (maximize the resulting fluorescent signal). Many fluorescent quenching groups can be placed internally and achieve efficient quenching, however many if not most of these chemical groups interfere with probe cleavage, especially when the distance between fluorophore and quencher is less than 12 nucleotides. This principle is demonstrated in Example 3, where certain quenchers, such as BHQ-1, can achieve very efficient quenching of a 5'-fluorophore, such as Fluorescein (6-FAM), yet the actual magnitude of the fluorescent signal generated during real-time PCR is small, compromising the actual performance and sensitivity of the assay. In contrast, similar internal placement of the quenchers provided herein, are fully compatible with probe hydrolysis and final functional signal generation is large.

Traditional DLPs having a 5'-fluorophore and 3'-quencher perform poorly when probe length nears or exceeds 30 nucleotides (nt), because quenching efficiency drops to the point that the probe remains relatively bright even in the quenched state. The present disclosure provides probes of 30 nt length, 35 nt length, or longer as needed for the precise application, having internal quenchers substantially closer to the fluorophore. Quenching in the compositions of this disclosure remains highly efficient as the internal quencher can be inserted the same distance from the fluorophore regardless of probe length. Thus high quality, efficiently quenched probes of an expanded potential length range are possible, which may be of particular importance when working with nucleic acids which are very AT rich. Sequences that are AT-rich have lower melting temperatures and longer probes must be utilized to function in the temperature ranges typically needed for PCR.

The compounds of this disclosure can also be utilized in molecular beacon assays. Molecular beacon assays contain probes that contain terminal 3' and 5' ends that self-hybridize to form a stem-loop structure. One end typically contains a terminal fluorophore group and the other end contains a terminal quencher group. When the probe hybridizes to the target the quencher is no longer near the fluorophore and the signal increases. Typically the hybridizing portions of the probes are 4-7 base pairs long. Beacon probes that contain insertions as described herein, preferably within the hybridized portion of the beacon, and more preferably within 1-2 bases from the terminal end, the stability is increased. Therefore shorter hybridizing regions can be used to generate the same performance as a conventional beacon.

A wide variety of reactive fluorescent reporter dyes are known in the literature and can be used in the compositions of this disclosure, so long as they are quenched by the precise quencher group or combination of quencher groups employed. The precise fluorophore/quencher pair employed in a dual-labeled probe is usually carefully chosen from a relatively small set of pairings that work well together based upon the emission wavelength of the fluorophore and the absorption wavelength of the quencher. Placement of the quencher in an internal position, as provided here, closer to the fluorophore than is achievable with an end-labeled probe permits efficient quenching even of fluorophore/quencher pairs that usually do not work well together, expanding the utility of the quencher by enabling its use with a wider range of fluorophores. Attachment of a second quencher to the probe can even further expand the useful spectral range.

The oligonucleotide probes provided herein may incorporate one or more fluorophores. The fluorophores can be attached internally or at the 5'- or 3'-end. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluoroscein, rhodamine or other like compound. Suitable fluorescent reporters include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl) aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p-(2-benzoxazolyl) phenyl)maleimide; cyanines, such as indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyloxacarbocyanine (CyA); 1H,5H,11H,15H-Xantheno[2,3,4-ij:5,6,7-i'j']diquinolizin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like. See Haugland, "Molecular Probes Handbook of Fluorescent Probes and Research Chemicals" for further fluorophore examples.

Reagents for incorporation the modification compounds of the present disclosure into oligonucleotides may have the following general structure:

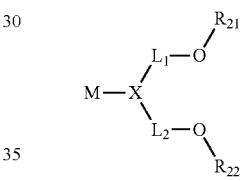

where $R_{13}$ is a protecting group on the oxygen atom, most commonly a trityl group, and preferably a dimethoxytrityl group, and $R_{22}$ is a phosphoramidite, a phosphate group, or a hydrogen phosphate used to couple the reagent to the growing oligonucleotide chain during synthesis. A phosphoramidite is preferred. A N,N-diisopropyl-β-cyanoethyl phosphoramidite is the most preferred reactive group.

As used herein, the terms "nucleic acid" and "oligonucleotide," as used herein, refer to polydeoxyribonucleotides (containing 2-deoxy-D-ribose), polyribonucleotides (containing D-ribose), and to any other type of polynucleotide which is an N glycoside of a purine or pyrimidine base. There is no intended distinction in length between the terms "nucleic acid", "oligonucleotide", "oligomer" or "oligo", and these terms will be used interchangeably. These terms refer only to the primary structure of the molecule. Thus, these terms include double- and single-stranded DNA, as well as double- and single-stranded RNA. An oligonucleotide also can comprise nucleotide analogs in which the base, sugar, or phosphate backbone is modified as well as non-purine or non-pyrimidine nucleotide analogs oligonucleotides, which may comprise naturally occurring nucleosides or chemically modified nucleosides. In some embodiments, the compounds comprise modified sugar moieties, modified internucleoside linkages, or modified nucleobase moieties.

The term "base" as used herein includes purines, pyrimidines and non-natural bases and modifications well-known in the art. Purines include adenine, guanine and xanthine and modified purines such as 8-oxo-$N^6$-methyladenine and 7-deazaxanthine. Pyrimidines include thymine, uracil and cytosine and their analogs such as 5-methylcytosine and 4,4-ethanocytosine. Non-natural bases include 5-fluorouracil, 5-bromouracil, 5-chlorouracil, 5-iodouracil, hypoxanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

The term "base" is sometimes used interchangeably with "monomer", and in this context it refers to a single nucleic acid or oligomer unit in a nucleic acid chain.

The term "probe" as used herein refers to nucleic acid oligonucleotides that produce a detectable response upon interaction with a target. The probes include at least one detectable moiety, a pair of moieties that form an energy transfer pair detectable upon some change of state of the probe in response to its interaction with a binding partner, or more than two moieties such as a fluorophore and more than one quencher.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product. The region of the primer which is sufficiently complementary to the template to hybridize is referred to herein as the hybridizing region.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two step cycles have a high temperature denaturation step followed by a hybridization/elongation (or ligation) step. Three step cycles comprise a denaturation step followed by a hybridization step followed by a separate elongation or ligation step.

The following examples further illustrate the invention but, of course, should not be construed as in any way limiting its scope.

Example 1

This example demonstrates the improved stability of probes containing modifications of the present disclosure compared to a selection of other compounds.

Oligonucleotide Synthesis and Purification.

DNA oligonucleotides were synthesized using solid phase phosphoramidite chemistry, deprotected and desalted on NAP-5 columns (Amersham Pharmacia Biotech, Piscataway, N.J.) according to routine techniques (Caruthers et al., Methods Enzymol 1992, 211:3-20). The oligomers were purified using reversed-phase high performance liquid chromatography (RP-HPLC). The purity of each oligomer was determined by capillary electrophoresis (CE) carried out on a Beckman P/ACE MDQ system (Beckman Coulter, Inc., Fullerton, Calif.). All single strand oligomers were at least 90% pure. Electrospray-ionization liquid chromatography mass spectroscopy (ESI-LCMS) of the oligonucleotides was conducted using an Oligo HTCS system (Novatia, Princeton, N.J.), which consisted of ThermoFinnigan TSQ7000, Xcalibur data system, ProMass data processing software and Paradigm MS4™ HPLC (Michrom BioResources, Auburn, Calif.). Protocols recommended by manufacturers were followed. Experimental molar masses for all single strand oligomers were within 1.5 g/mol of expected molar mass. These results confirm identity of the oligomers.

Preparation of DNA Samples.

Melting experiments were carried out in buffer containing 3.87 mM $NaH_2PO_4$, 6.13 mM $Na_2HPO_4$, 1 mM $Na_2EDTA$ and 1000 mM NaCl. 1 M NaOH was used to titrate each solution to pH 7.0. Total sodium concentrations were estimated to be 1020 mM. The DNA samples were thoroughly dialyzed against melting buffer in a 28-Well Microdialysis System (Life Technologies, Carlsbad, Calif.) following the manufacturer's recommended protocol. Concentrations of DNA oligomers were estimated from the samples' UV absorbance at 260 nm in a spectrophotometer (Beckman Coulter, Inc., Fullerton, Calif.), using extinction coefficients for each oligonucleotide that were estimated using the nearest neighbor model for calculating extinction coefficients. (See, Warshaw et al., J. Mol. Biol. 1966, 20:29-38).

Internal Modifications Studied.

Figure 1B:
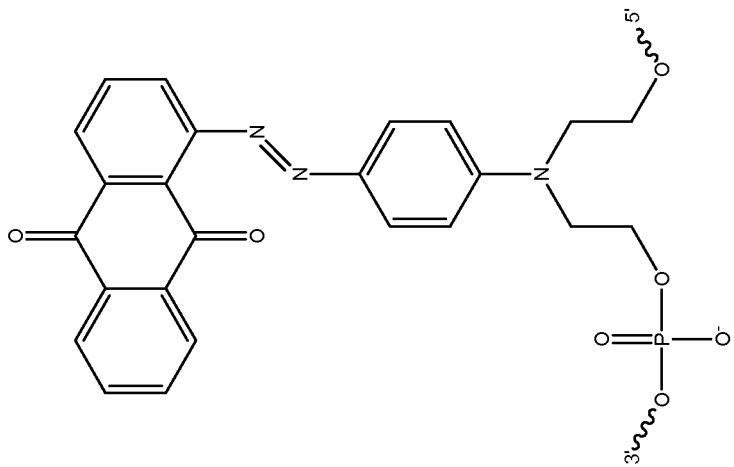
Figure 1B:
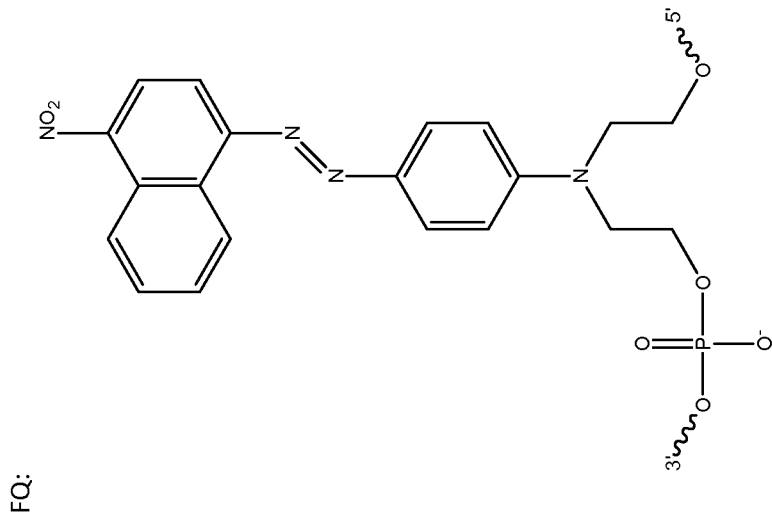
Figure 1B:
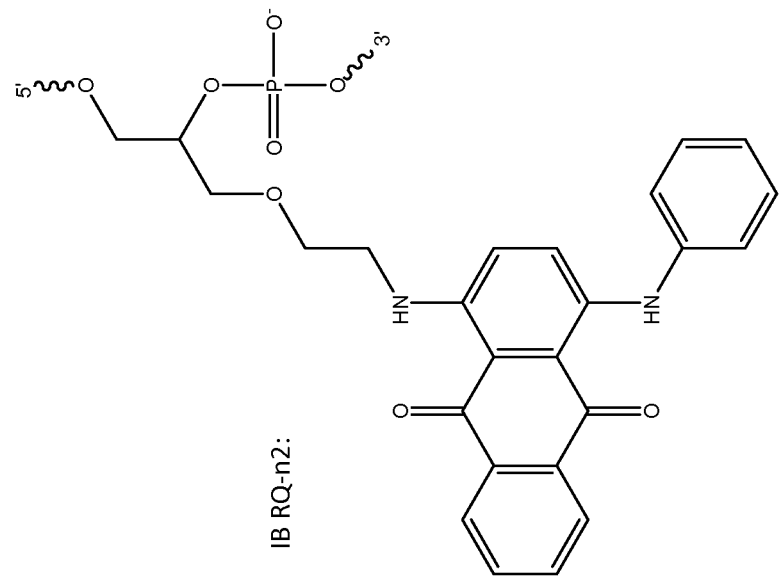
Figure 1B:
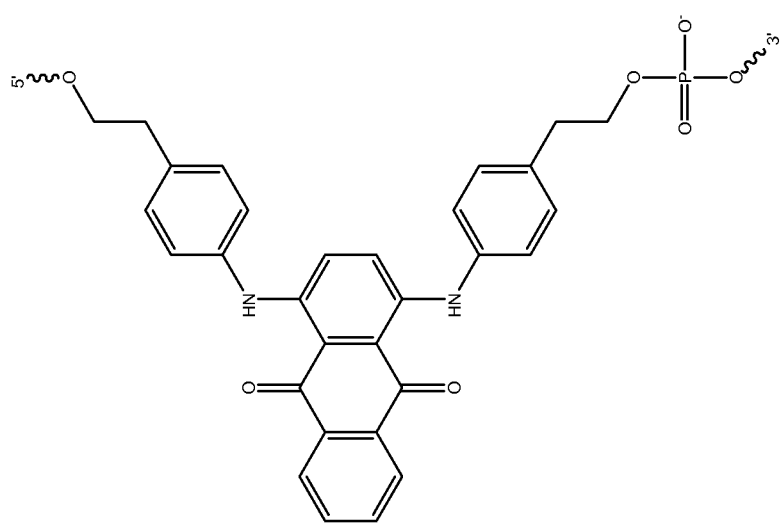
Figure 1C:
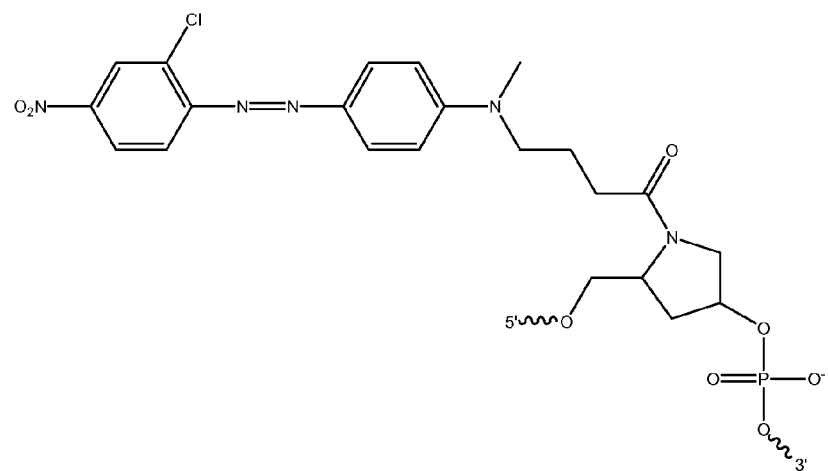
Figure 1C:
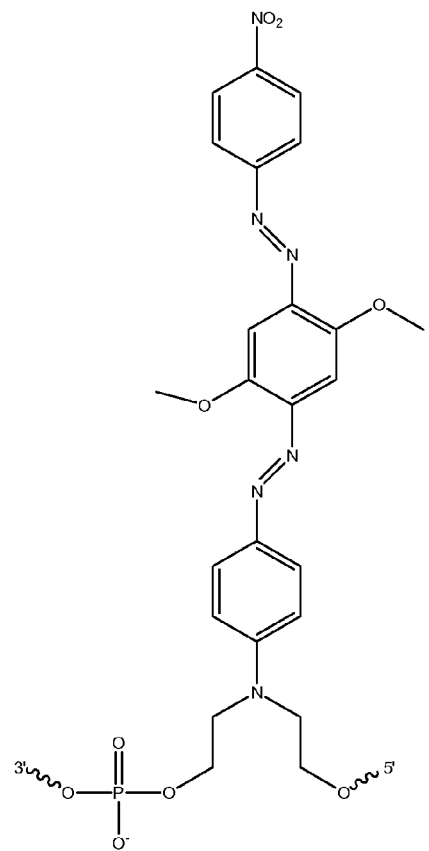

FIGS. 1A-1C show the structures of modified portions of the various modified oligonucleotides studied in this example and in Example 2. The FQ (Integrated DNA Technologies, Inc., sometimes referred to as "iFQ" in this application), was introduced into oligonucleotides using phosphoramidite reagents at the time of synthesis. See Example 10 for synthesis of the phosphoramidite. In the first series of duplexes, the iFQ group was placed as an insertion between bases in the duplex so that a 10 base top strand annealed to a 10 base bottom strand and the iFQ group was not aligned to a base. Additionally, 10-mer oligonucleotides with C3 spacer insertions were also synthesized and studied. The C3 spacer represents the control wherein a linear insertion of a phosphate group plus propanediol is placed between bases, which is similar to the iFQ insertions without having the nathylene-azo ring structures present. Extinction coefficients at 260 nm of iFQ was estimated to be 13340; the C3 spacer does not contribute to UV absorbance. Two 20 base and two 25 base duplexes of similar design were also studied. A second set of 10 base duplexes was studied where the iFQ group was placed as a substitution such that a 10 base top strand (5 bases—iFQ—5 bases) was annealed to an 11 base bottom strand so that the iFQ group functioned as a substitution or replacement for a base. Four duplexes of this design were tested, one comprising each of the 4 bases (AGCT) to pair with the iFQ group.

Measurement of Melting Curves.

Oligomer concentrations were measured at least twice for each sample. If the estimated concentrations for any sample differed more than 4%, the results were discarded and new absorbance measurements were performed. To prepare oligonucleotide duplexes, complementary DNA oligomers were mixed in 1:1 molar ratio, heated to 367 K (i.e., 94° C.) and slowly cooled to an ambient temperature. Each solution of duplex DNA was diluted with melting buffer to a total DNA concentration ($C_T$) of 2 µM.

Melting experiments were conducted on a single beam Beckman DU 650 spectrophotometer (Beckman-Coulter) with a Micro $T_m$ Analysis accessory, a Beckman High Performance Peltier Controller (to regulate the temperature), and 1 cm path-length cuvettes. Melt data were recorded using a PC interfaced to the spectrophotometer. UV-absorbance values at 268 nm wavelength were measured at 0.1 degree increments in the temperature range from 383 to 368 K (i.e., 10-95° C.). Both heating (i.e., denaturation) and cooling (i.e., renaturation) transition curves were recorded in each sample at a controlled rate of temperature change (24.9±0.3° C. per hour). Sample temperatures were collected from the internal probe located inside the Peltier holder, and recorded with each sample's UV-absorbance data. Melting profiles were also recorded for samples of buffer alone (no oligonucleotide), and these blank profiles were digitally subtracted from melting curves of the DNA samples. To minimize systematic errors, at least two melting curves were collected for each sample in different cuvettes and in different positions within the Peltier holder.

Determination of Melting Temperatures.

To determine each sample's melting temperature, the melting profiles were analyzed using methods that have been previously described (see, Doktycz et al., *Biopolymers* 1992, 32:849-864; Owczarzy et al., *Biopolymers* 1997, 44:217-239; Owczarzy R., *Biophys. Chem.* 2005, 117: 207-215.). Briefly, the experimental data for each sample was smoothed, using a digital filter, to obtain a plot of the sample's UV-absorbance as a function of its temperature. The fraction of single-stranded oligonucleotide molecules, θ, was then calculated from that plot. The melting temperature or $T_m$ of a sample was defined as the temperature where θ=0.5.

Table 1 lists the sequences tested, the internal quenchers used, and the resulting melting temperatures.

TABLE 1

Melting Temperatures for nucleic acids containing internal quencher moieties, where iFQ = internal FQ azo quencher, and iSpC3 = internal C3 spacer.

| SEQ ID NO. | Duplex Sequence | N | $T_m$(C.) | $\Delta T_m$(C.) |
|---|---|---|---|---|
| 1 | 5'-ATCGTTGCTA-3' | 10 | 43.85 | 0.0 |
| 2 | 3'-TAGCAACGAT-5' | 10 | | |
| 3 | 5'-ATC/iFQ/GTTGCTA-3' | 10 | 48.05 | 4.2 |
| 2 | 3'-TAGCAACGAT-5' | 10 | | |
| 4 | 5'-ATCG/iFQ/TTGCTA-3' | 10 | 48.55 | 4.7 |
| 2 | 3'-TAGCAACGAT-5' | 10 | | |
| 5 | 5'-ATCGT/iFQ/TGCTA-3' | 10 | 46.35 | 2.5 |
| 2 | 3'-TAGCAACGAT-5' | 10 | | |
| 6 | 5'-CTTGGATCGTTGCTAGTAGG-3' | 20 | 69.55 | 0.0 |
| 7 | 3'-GAACCTAGCAACGATCATCC-5' | 20 | | |
| 8 | 5'-CTTGGATCGT/iFQ/TGCTAGTAGG-3' | 20 | 71.35 | 1.8 |
| 7 | 3'-GAACCTAGCAACGATCATCC-5' | 20 | | |
| 9 | 5'-CACTTGGATCGTTGCTAGTAGGGTC-3' | 25 | 76.15 | 0.0 |
| 10 | 3'-GTGAACCTAGCAACGATCATCCCAG-5' | 25 | | |

TABLE 1-continued

Melting Temperatures for nucleic acids containing
internal quencher moieties, where iFQ = internal
FQ azo quencher, and iSpC3 = internal C3 spacer.

| SEQ ID NO. | Duplex Sequence | N | $T_m$(C.) | $\Delta T_m$(C.) |
|---|---|---|---|---|
| 11 | 5'-CACTTGGATC/iFQ/GTTGCTAGTAGGGTC-3' | 25 | 77.05 | 0.9 |
| 10 | 3'-GTGAACCTAGCAACGATCATCCCAG-5' | 25 | | |
| 12 | 5'-ATC/iSpC3/GTTGCTA-3' | 10 | 36.35 | -7.5 |
| 2 | 3'-TAGCAACGAT-5' | 10 | | |
| 13 | 5'-ATCG/iSpC3/TTGCTA-3' | 10 | 36.55 | -7.3 |
| 2 | 3'-TAGCAACGAT-5' | 10 | | |
| 14 | 5'-ATCGT/iSpC3/TGCTA-3' | 10 | 32.55 | -11.3 |
| 2 | 3'-TAGCAACGAT-5' | 10 | | |
| 5 | 5'-ATCGT/iFQ/TGCTA-3' | 10 | 47.35 | 3.5 |
| 15 | 3'-TAGCA/iSpC3/ACGAT-5' | 10 | | |
| 5 | 5'-ATCGT/iFQ/TGCTA-3' | 10 | 42.24 | -1.6 |
| 16 | 3'-TAGCAAACGAT-5' | 11 | | |
| 5 | 5'-ATCGT/iFQ/TGCTA-3' | 10 | 45.27 | 1.4 |
| 17 | 3'-TAGCACACGAT-5' | 11 | | |
| 5 | 5'-ATCGT/iFQ/TGCTA-3' | 10 | 40.44 | -3.4 |
| 18 | 3'-TAGCAGACGAT-5' | 11 | | |
| 5 | 5'-ATCGT/iFQ/TGCTA-3' | 10 | 45.27 | 1.4 |
| 19 | 3'-TAGCATACGAT-5' | 11 | | |

Three different insertion placement sites were studied using a 10-mer oligonucleotide scaffold. Use of the shorter sequences most clearly demonstrates the potential effects on $T_m$ and testing different placement sites illustrate that the $T_m$ effects can be sequence context dependent. The relative $\Delta T_m$ shifts for the modified vs. unmodified 10mer sequences were averaged and are summarized in Table 2 below.

TABLE 2

Average $\Delta T_m$ shifts for three 10mer sequences with internal modifiers

| Modifier | iFQ (insertion) | iFQ (substitution) | iSpC3 |
|---|---|---|---|
| $\Delta T_m$ | +3.8° C. | -0.6° C. | -8.7° C. |

As Tables 1 and 2 illustrate, disrupting a DNA sequence with a modification that is small and offers no steric hindrance (or stabilization) like a propanediol group (C3 spacer) has a significant negative impact on the $T_m$ of a duplex ($\Delta T_m$ of -8.7° C.). In contrast, the napthylene-azo-class quencher studied (iFQ) significantly stabilized the duplex compared with the iC3 control. A greater degree of stabilization was seen when the iFQ was placed as an insertion ($\Delta T_m$ of +12.5° C. relative to the iSpC3) than when the iFQ was placed as a base substitution ($\Delta T_m$ of +8.1° C. relative to the iSpC3). Unexpectedly, use of the iFQ group as an insertion between bases stabilized the duplex compared to the unmodified parent duplex ($\Delta T_m$ of +3.8° C. relative to the unmodified duplex), while base substitution resulted in slight destabilization ($\Delta T_m$ of -0.6° C. relative to the unmodified duplex).

Therefore internal incorporation of the napthylene-azo group within a DNA duplex stabilizes the duplex when placed as an insertion between bases.

Certain anthraquinone groups can stabilize a duplex when placed on the ends (J. Am. Chem. Soc., 131:12671-12681, 2009); however this effect has not been described for internal placement or using napthylene-azo compounds. Therefore the use of internal napthylene-azo-class quenchers would be preferred to maintain duplex stability.

Example 2

The following example compares 10 base pair sets of duplexes with varying modification insertions placed at varying location along the 10-mer oligonucleotide. The structures of the modified portions of the various modified oligonucleotides are illustrated in FIGS. 1A-1C. As noted earlier, the synthesis of FQ phosphoramidite is described in Example 10. The structure "IB 1.1" is synthesized in the same manner as FQ except an aminoanthraquinone reagent is used instead of 4-nitro-1-napthylamine. The IB RQ quenchers are anthraquinone-based compounds (U.S. Pat. Application 2004/0110308) which are commonly used with red wavelength fluorescent dyes.

The preparation of the DNA samples, the measurement of melting curves and determination of melting temperatures were performed as in Example 1. Table 3 lists the resulting Tm data for each duplex studied, as well as the $\Delta T_m$ relative to the duplex formed with the unmodified oligonucleotide.

TABLE 3

| SEQ ID No. | Sequence | $T_m$ | $\Delta T_m$ |
|---|---|---|---|
| 1 | 5' ATCGTTGCTA | 43.9 | — |
| 2 | 3' TAGCAACGAT | | |
| 20 | 5' ATC/GTTGCTA N-MDA "/" | 31.0 | -12.9 |
| 2 | 3' TAG CAACGAT | | |

TABLE 3-continued

| SEQ ID No. | Sequence | $T_m$ | $\Delta T_m$ |
|---|---|---|---|
| 21 | 5' ATC/GTTGCTA C2 "/"<br>2  3' TAG CAACGAT | 37.8 | −6.1 |
| 22 | 5' ATC/GTTGCTA 2,2 DMP "/"<br>2  3' TAG CAACGAT | 34.9 | −9.0 |
| 12 | 5' ATC/GTTGCTA iSpC3 "/"<br>2  3' TAG CAACGAT | 36.3 | −7.6 |
| 23 | 5' ATC/GTTGCTA C4 "/"<br>2  3' TAG CAACGAT | 30.1 | −13.8 |
| 24 | 5' ATC/GTTGCTA C5 "/"<br>2  3' TAG CAACGAT | 27.3 | −16.6 |
| 25 | 5' ATC/GTTGCTA C6 "/"<br>2  3' TAG CAACGAT | 26.1 | −17.8 |
| 26 | 5' ATC/GTTGCTA C7 "/"<br>2  3' TAG CAACGAT | 24.7 | −19.1 |
| 27 | 5' ATC/GTTGCTA iSpS9 "/"<br>2  3' TAG CAACGAT | 28.5 | −15.4 |
| 28 | 5' ATC/GTTGCTA idSp "/"<br>2  3' TAG CAACGAT | 33.5 | −10.4 |
| 3 | 5' ATC/GTTGCTA iFQ "/"<br>2  3' TAG CAACGAT | 48.0 | +4.1 |
| 29 | 5' ATC/GTTGCTA iBHQ2 "/"<br>2  3' TAG CAACGAT | 45.0 | +1.1 |
| 30 | 5' ATC/GTTGCTA iRQ-n1 "/"<br>2  3' TAG CAACGAT | 38.7 | −5.2 |
| 31 | 5' ATC/GTTGCTA iRQ-n2 "/"<br>2  3' TAG CAACGAT | 46.0 | +2.1 |
| 32 | 5' ATC/GTTGCTA iEc "/"<br>2  3' TAG CAACGAT | 40.1 | −3.8 |
| 33 | 5' ATC/GTTGCTA IB 1.1 "/"<br>2  3' TAG CAACGAT | 47.6 | +3.7 |
| 34 | 5' ATC/GTTGCTA NPDA "/"<br>2  3' TAG CAACGAT | 29.3 | −14.6 |
| 35 | 5' ATCG/TTGCTA N-MDA "/"<br>2  3' TAGC AACGAT | 34.1 | −9.8 |
| 36 | 5' ATCG/TTGCTA C2 "/"<br>2  3' TAGC AACGAT | 38.6 | −5.3 |
| 37 | 5' ATCG/TTGCTA 2,2 DMP "/"<br>2  3' TAGC AACGAT | 35.5 | −8.4 |
| 13 | 5' ATCG/TTGCTA iSpC3 "/"<br>2  3' TAGC AACGAT | 36.6 | −7.3 |
| 38 | 5' ATCG/TTGCTA C4 "/"<br>2  3' TAGC AACGAT | 32.0 | −11.9 |
| 39 | 5' ATCG/TTGCTA C5 "/"<br>2  3' TAGC AACGAT | 28.1 | −15.8 |
| 40 | 5' ATCG/TTGCTA C6 "/"<br>2  3' TAGC AACGAT | 26.5 | −17.4 |
| 41 | 5' ATCG/TTGCTA C7 "/"<br>2  3' TAGC AACGAT | 24.7 | −19.2 |
| 42 | 5' ATCG/TTGCTA iSpS9 "/"<br>2  3' TAGC AACGAT | 29.1 | −14.8 |
| 43 | 5' ATCG/TTGCTA idSp "/"<br>2  3' TAGC AACGAT | 34.1 | −9.8 |

TABLE 3-continued

| SEQ ID No. | Sequence | $T_m$ | $\Delta T_m$ |
|---|---|---|---|
| 4 | 5' ATCG/TTGCTA iFQ "/"<br>2  3' TAGC AACGAT | 48.6 | +4.7 |
| 44 | 5' ATCG/TTGCTA iBHQ2 "/"<br>2  3' TAGC AACGAT | 43.3 | −0.6 |
| 45 | 5' ATCG/TTGCTA iRQ-n1 "/"<br>2  3' TAGC AACGAT | 34.7 | −9.2 |
| 46 | 5' ATCG/TTGCTA iRQ-n2 "/"<br>2  3' TAGC AACGAT | 44.7 | +0.8 |
| 47 | 5' ATCG/TTGCTA iEc "/"<br>2  3' TAGC AACGAT | 35.7 | −8.2 |
| 48 | 5' ATCG/TTGCTA IB 1.1 "/"<br>2  3' TAGC AACGAT | 45.9 | +2.1 |
| 49 | 5' ATCG/TTGCTA NPDA "/"<br>2  3' TAGC AACGAT | 30.0 | −13.9 |
| 50 | 5' ATCGT/TGCTA C2 "/"<br>2  3' TAGCA ACGAT | 34.0 | −9.9 |
| 51 | 5' ATCGT/TGCTA 2,2 DMP "/"<br>2  3' TAGCA ACGAT | 33.1 | −10.8 |
| 14 | 5' ATCGT/TGCTA iSpC3 "/"<br>2  3' TAGCA ACGAT | 32.6 | −11.3 |
| 52 | 5' ATCGT/TGCTA C4 "/"<br>2  3' TAGCA ACGAT | 26.4 | −17.5 |
| 53 | 5' ATCGT/TGCTA C5 "/"<br>2  3' TAGCA ACGAT | 23.3 | −20.6 |
| 54 | 5' ATCGT/TGCTA C6 "/"<br>2  3' TAGCA ACGAT | 21.9 | −22.0 |
| 55 | 5' ATCGT/TGCTA C7 "/"<br>2  3' TAGCA ACGAT | 20.4 | −23.5 |
| 56 | 5' ATCGT/TGCTA iSpS9 "/"<br>2  3' TAGCA ACGAT | 24.4 | −19.5 |
| 57 | 5' ATCGT/TGCTA idSp "/"<br>2  3' TAGCA ACGAT | 31.8 | −12.1 |
| 5 | 5' ATCGT/TGCTA iFQ "/"<br>2  3' TAGCS ACGAT | 46.3 | +2.4 |
| 58 | 5' ATCGT/TGCTA iBHQ2 "/"<br>2  3' TAGCA ACGAT | 41.5 | −2.4 |
| 59 | 5' ATCGT/TGCTA iRQ-n1 "/"<br>2  3' TAGCA ACGAT | 32.1 | −11.8 |
| 60 | 5' ATCGT/TGCTA iRQ-n2 "/"<br>2  3' TAGCA ACGAT | 42.6 | −1.3 |
| 61 | 5' ATCGT/TGCTA iEc "/"<br>2  3' TAGCA ACGAT | 33.1 | −10.8 |
| 62 | 5' ATCGT/TGCTA IB 1.1 "/"<br>2  3' TAGCA ACGAT | 44.7 | +0.8 |
| 63 | 5' ATCGT/TGCTA NPDA "/"<br>2  3' TAGCA ACGAT | 26.8 | −17.1 |
| 64 | 5' A/TCGTTGCTA N-MDA "/"<br>2  3' T AGCAACGAT | 40.9 | −3.0 |
| 65 | 5' A/TCGTTGCTA C2 "/"<br>2  3' T AGCAACGAT | 43.5 | −0.4 |

TABLE 3-continued

| SEQ ID No. | Sequence | $T_m$ | $\Delta T_m$ |
|---|---|---|---|
| 66 | 5' A/TCGTTGCTA 2,2 DMP "/" | 43.4 | −0.4 |
| 2 | 3' T AGCAACGAT | | |
| 67 | 5' A/TCGTTGCTA iSpC3 "/" | 44.6 | +0.7 |
| 2 | 3' T AGCAACGAT | | |
| 68 | 5' A/TCGTTGCTA C4 "/" | 43.3 | −0.6 |
| 2 | 3' T AGCAACGAT | | |
| 69 | 5' A/TCGTTGCTA C5 "/" | 41.5 | −2.4 |
| 2 | 3' T AGCAACGAT | | |
| 70 | 5' A/TCGTTGCTA C6 "/" | 41.6 | −2.3 |
| 2 | 3' T AGCAACGAT | | |
| 71 | 5' A/TCGTTGCTA C7 "/" | 43.2 | −0.7 |
| 2 | 3' T AGCAACGAT | | |
| 72 | 5' A/TCGTTGCTA iSpS9 "/" | 41.5 | −2.4 |
| 2 | 3' T AGCAACGAT | | |
| 73 | 5' A/TCGTTGCTA idSp "/" | 43.0 | −0.9 |
| 2 | 3' T AGCAACGAT | | |
| 74 | 5' A/TCGTTGCTA iFQ "/" | 51.8 | +7.9 |
| 2 | 3' T AGCAACGAT | | |
| 75 | 5' A/TCGTTGCTA iBHQ2 "/" | 48.9 | +5.0 |
| 2 | 3' T AGCAACGAT | | |
| 76 | 5' A/TCGTTGCTA iRQ-n1 "/" | 48.2 | +4.3 |
| 2 | 3' T AGCAACGAT | | |
| 77 | 5' A/TCGTTGCTA iRQ-n2 "/" | 49.1 | +5.2 |
| 2 | 3' T AGCAACGAT | | |
| 78 | 5' A/TCGTTGCTA iEc "/" | 44.5 | +0.6 |
| 2 | 3' T AGCAACGAT | | |
| 79 | 5' A/TCGTTGCTA IB 1.1 "/" | 51.2 | +7.3 |
| 2 | 3' T AGCAACGAT | | |
| 80 | 5' A/TCGTTGCTA NPDA "/" | 41.0 | −2.9 |
| 2 | 3' T AGCAACGAT | | |
| 81 | 5' ATCGTTGCT/A C2 "/" | 44.2 | +0.3 |
| 2 | 3' TAGCAACGA T | | |
| 82 | 5' ATCGTTGCT/A 2,2 DMP "/" | 43.8 | −0.1 |
| 2 | 3' TAGCAACGA T | | |
| 83 | 5' ATCGTTGCT/A iSpC3 "/" | 44.5 | +0.6 |
| 2 | 3' TAGCAACGA T | | |
| 84 | 5' ATCGTTGCT/A C4 "/" | 43.4 | −0.5 |
| 2 | 3' TAGCAACGA T | | |
| 85 | 5' ATCGTTGCT/A C5 "/" | 42.8 | −1.0 |
| 2 | 3' TAGCAACGA T | | |
| 86 | 5' ATCGTTGCT/A C6 "/" | 43.3 | −0.6 |
| 2 | 3' TAGCAACGA T | | |
| 87 | 5' ATCGTTGCT/A C7 "/" | 40.9 | −3.0 |
| 2 | 3' TAGCAACGA T | | |
| 88 | 5' ATCGTTGCT/A iSpS9 "/" | 44.2 | +0.3 |
| 2 | 3' TAGCAACGA T | | |
| 89 | 5' ATCGTTGCT/A idSp "/" | 44.7 | +0.8 |
| 2 | 3' TAGCAACGA T | | |
| 90 | 5' ATCGTTGCT/A iFQ "/" | 50.3 | +6.4 |
| 2 | 3' TAGCAACGA T | | |
| 91 | 5' ATCGTTGCT/A iBHQ2 "/" | 50.7 | +6.8 |
| 2 | 3' TAGCAACGA T | | |
| 92 | 5' ATCGTTGCT/A iRQ-n1 "/" | 48.6 | +4.7 |
| 2 | 3' TAGCAACGA T | | |
| 93 | 5' ATCGTTGCT/A iRQ-n2 "/" | 47.5 | +3.6 |
| 2 | 3' TAGCAACGA T | | |
| 94 | 5' ATCGTTGCT/A iEc "/" | 45.8 | +1.9 |
| 2 | 3' TAGCAACGA T | | |
| 95 | 5' ATCGTTGCT/A IB 1.1 "/" | 50.9 | +7.0 |
| 2 | 3' TAGCAACGA T | | |
| 96 | 5' ATCGTTGCT/A NPDA "/" | 43.9 | +0.0 |
| 2 | 3' TAGCAACGA T | | |

Figure 14A:
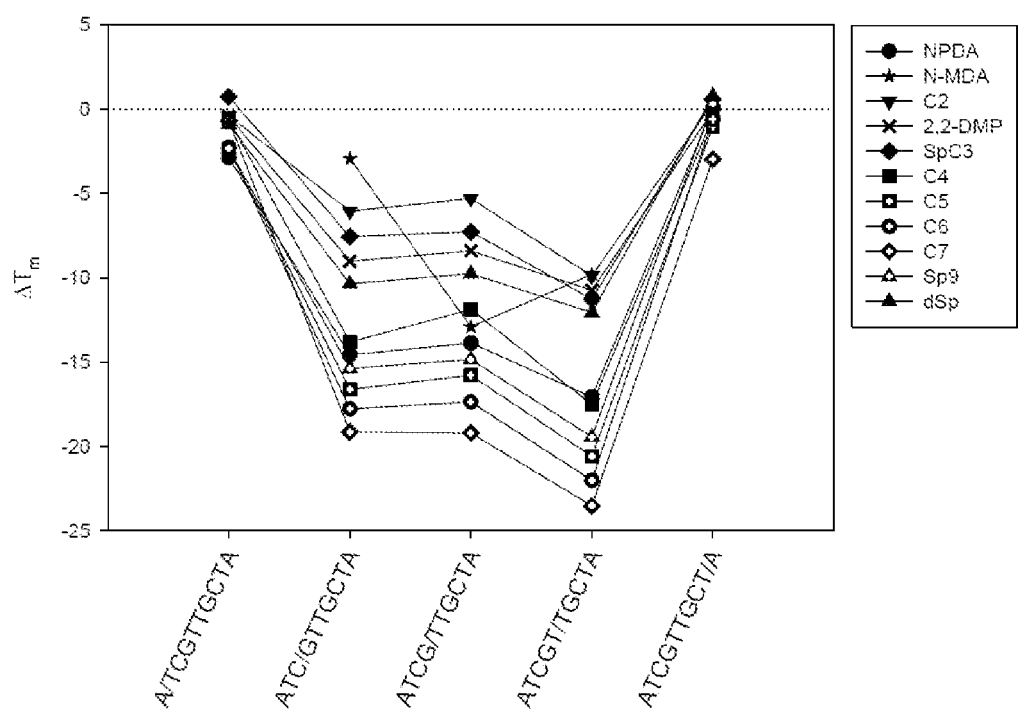
FIGS. 14A and 14B are plots showing the dependence of $\Delta T_m$ on the position of the insertion within an oligonucleotide for various modification compounds.
Figure 14B:
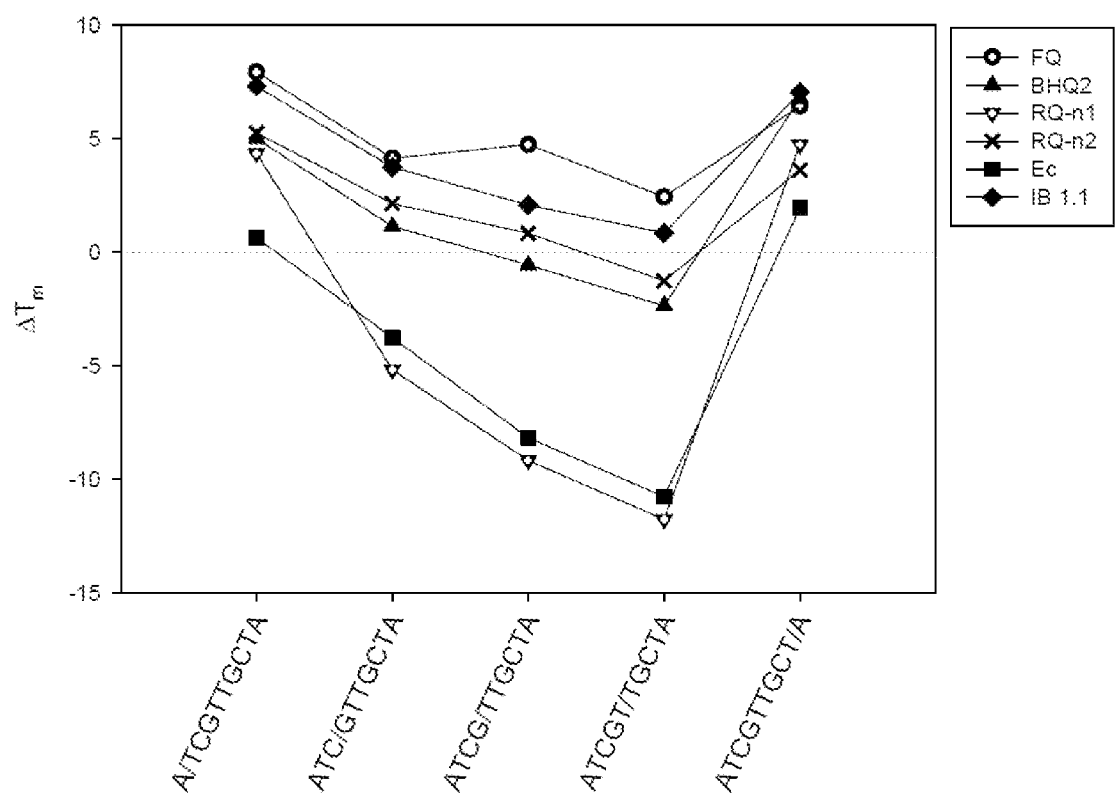

FIGS. 13A, 13B, 13C, 13D and 13E are bar charts each showing the $\Delta T_m$ caused by each of the modifications at a particular location within the nucleotide. FIGS. 14A and 14B are plots showing the dependence of $\Delta T_m$ on the position of the insertion within an oligonucleotide for each of the various modification compounds. In general, the insertion of a modification nearer the end of an oligonucleotide is less destabilizing than when it is inserted towards the middle of the oligonucleotide. The spacer modifications were all destabilizing, with the degree of destabilization increasing as the size of the spacer increased.

The FQ modification had a positive effect on stability whether it was inserted near an end or in the middle of the duplex. The IB 1.1 had nearly the same stability profile as FQ. The iRQ-n2 modification was also positive or negligible in its effect on duplex stability.

Example 3

This example details the predictive modeling for oligonucleotides containing an internal quencher.

The thermodynamic impact of internal FQ azo quencher (iFQ) modification was determined from the difference between modified and native duplex DNAs. Melting experiments were conducted at 2 μM DNA concentration ($C_t$) and in 1M Na⁺ buffer. Transition enthalpies (ΔH°) and entropies (ΔS°) where obtain from fits to individual melting profiles (Petersheim, M.& Turner, D. H. (1983) *Biochemistry*, 22, 256-263). The equilibrium constant $K_a$ was calculated from the fraction of broken base pairs (θ) at each temperature, $$K_a = \frac{2(1-\theta)}{\theta^2 C_t} \quad (1)$$

The graphs of $-\ln K_a$ vs. 1/T were least-square fit to straight lines and thermodynamic parameters were calculated from the slope and the intercept, $$-\ln K_a = \frac{\Delta H°}{RT} - \frac{\Delta S°}{R} \quad (2)$$

The fits were limited to the range of θ from 0.15 to 0.85, where θ and $K_a$ are the most accurate. The symbol R is the ideal gas constant (1.9865 cal/(mol*K)). Reported values of ΔH°, and ΔS° are averages from at least four heating and cooling melting profiles. This thermodynamic analysis assumes that the transition enthalpies and entropies are temperature-independent and melting transitions proceed in two-state manner. The results are summarized in Table 4. Average thermodynamic effect of inserted FQ azo quencher could be estimated from the following relationships, $$\Delta H° \text{ (modified oligo)} = \Delta H° \text{ (native oligo)} - 1272 \text{ cal/mol}$$

$$\Delta S° \text{ (modified oligo)} = \Delta S° \text{ (native oligo)} - 1.44 \text{ cal/(mol·K)}$$

When these equations were employed to predict melting temperatures of 20 and 25 base pair duplexes (Table 5), the average error of predictions was 0.7° C.

TABLE 6

Sequences used in q-PCR assays

| SEQ ID No. | Sequence Name | Sequence |
|---|---|---|
| 97 | HPRT Forward | GACTTTGCTTTCCTTGGTCAG |
| 98 | HPRT Reverse | GGCTTATATCCAACACTTCGTG |
| 99 | HPRT Probe | ATGGTCAAGGTCGCAAGCTTGCTGGT |

All oligonucleotides were synthesized by IDT (Integrated DNA Technologies, Coralville, Iowa). Probe oligonucleotides were HPLC purified. Mass identity of all oligonucleotides was verified by mass spectrometry. All target amplicons were cloned and sequence verified. The target plasmids

TABLE 4

Thermodynamic effects of internal FQ modifications

| SEQ ID No. | DNA sequence (5' to 3')[a] | ΔH° cal/mol | ΔΔH° cal/mol | ΔS° cal/(mol · K) | ΔΔS° cal/(mol · K) |
|---|---|---|---|---|---|
| 1 | ATCGTTGCTA | −68012 | | −185.62 | |
| 3 | ATC/iFQ/GTTGCTA | −71827 | −3815 | −194.73 | −9.12 |
| 4 | ATCG/iFQ/TTGCTA | −69783 | −1771 | −188.00 | −2.38 |
| 5 | ATCGT/iFQ/TGCTA | −66241 | 1771 | −178.45 | 7.17 |
| | Average effect | | −1272 | | −1.44 |

[a]Complementary DNA strand was 5'-TAGCAACGAT-3'.
Calculations were done using non-rounded values.

TABLE 5

Accuracy of $T_m$ predictions for two duplex DNAs containing internal FQ quencher that were not used to derive equations (1) and (2).

| SEQ ID No. | DNA sequence (5' to 3')[a] | $N_{bp}$ | Exper. $T_m$ (° C.) | Predicted $T_m$ (° C.) | Error of $T_m$ prediction (° C.) |
|---|---|---|---|---|---|
| 8 | CTTGGATCGT/iFQ/TGCTAGTAGG | 20 | 71.3 | 71.6 | 0.3 |
| 11 | CACTTGGATC/iFQ/GTTGCTAGTAGGGTC | 25 | 77.1 | 78.2 | 1.1 |

[a]Melting temperatures were calculated using the nearest-neighbor model (SantaLucia, J., Jr. (1998) *Proc. Natl. Acad. Sci. USA*, 95, 1460-1465) and equations (1) and (2).

The low error of prediction demonstrates the consistency and predictability of the effect of the addition of an internal quencher into an oligonucleotide.

Example 4

This example demonstrates the functional performance through quantitative real time PCR (q-PCR) using probes containing the novel internal quenchers disclosed herein.

Validated qPCR assays were used to assess the performance of the different designs of fluorescence quenched probes. The primer sequences employed were specific for the human HPRT gene (NM 00194); probe and primer sequences and are listed below in Table 6.

were linearized by restriction endonuclease digestion and 10 fold serial dilutions were performed to create standard curves.

HPRT q-PCR reactions were comprised of 0.4 U Immolase DNA Polymerase (Bioline, Taunton, Mass.), 0.8 mM dNTP mix, 3 mM $MgCl_2$, and primer/probe concentrations at 200 nM each. Q-PCR reactions were performed on a Roche Lightcycler® 480 platform. Plasmid copy number standards were run in triplicate starting with $2 \times 10^7$ down to $2 \times 10^2$ (10 fold increments). The thermocycling profile used was $95^{10:00}$–$(95^{0:15}$–$60^{1:00}) \times 40$. Data analysis was performed using software supplied by the manufacturer.

Effects of Placement of Internal FQ (iFQ).

Figure 2A:
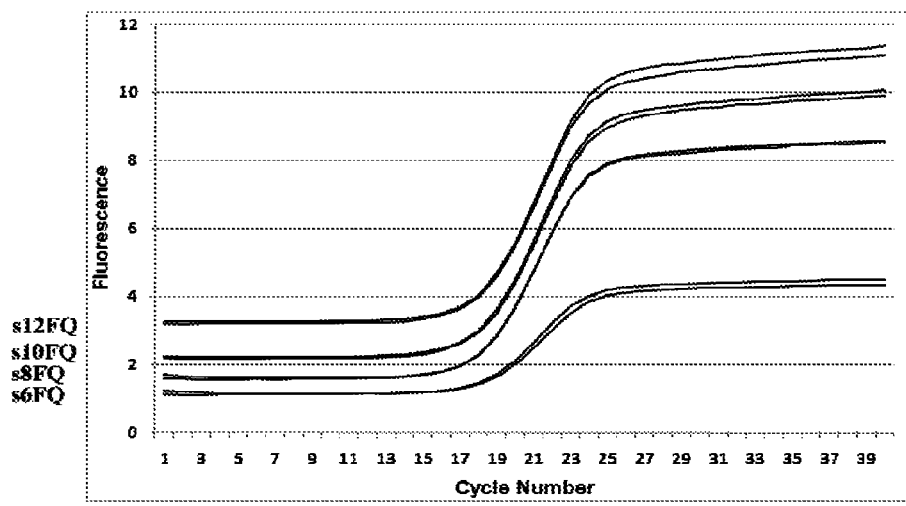
FIG. 2A is an amplification plot that illustrates the relative fluorescence intensity ($R_n$) of an HPRT q-PCR assay of the substitution data set for the FQ quencher located 6, 8, 10 and 12 positions from the 5'-fluorophore.
Figure 2B:
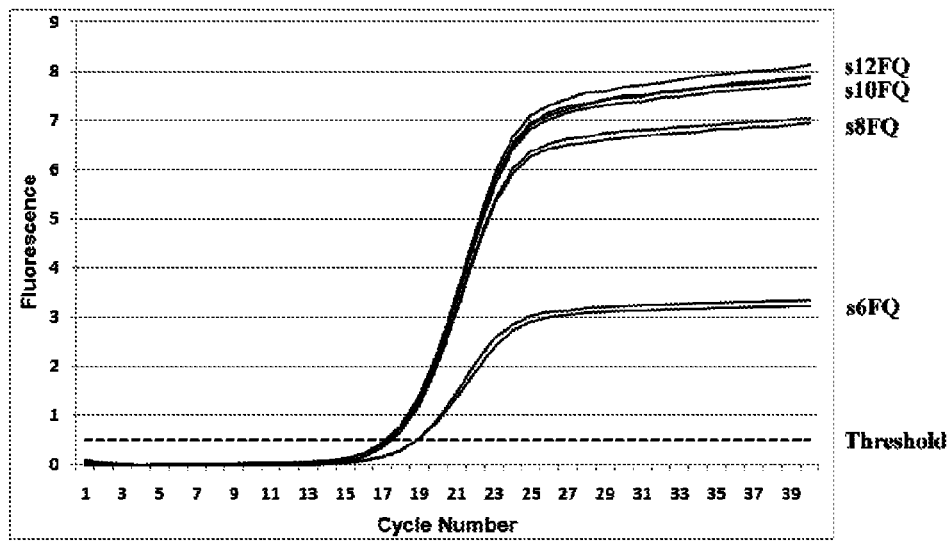
FIG. 2B is an amplification plot that illustrates the baseline adjusted fluorescence of results in FIG. 2A ($\Delta R_n$).
Figure 3A:
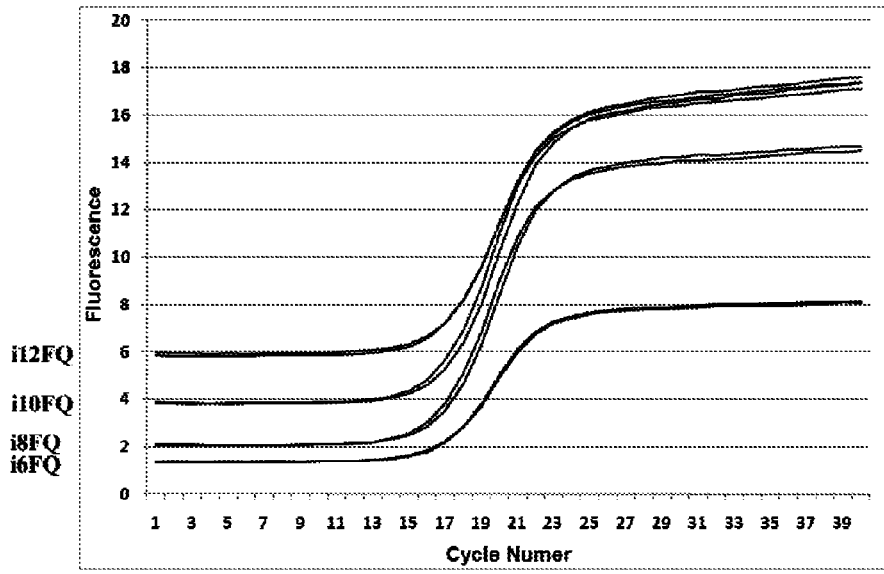
FIG. 3A is an amplification plot that illustrates the relative fluorescence intensity ($R_n$) of the HPRT q-PCR assay of the insertion data set for FQ quencher located 6, 8, 10 and 12 positions from the 5'-fluorophore.
Figure 3B:
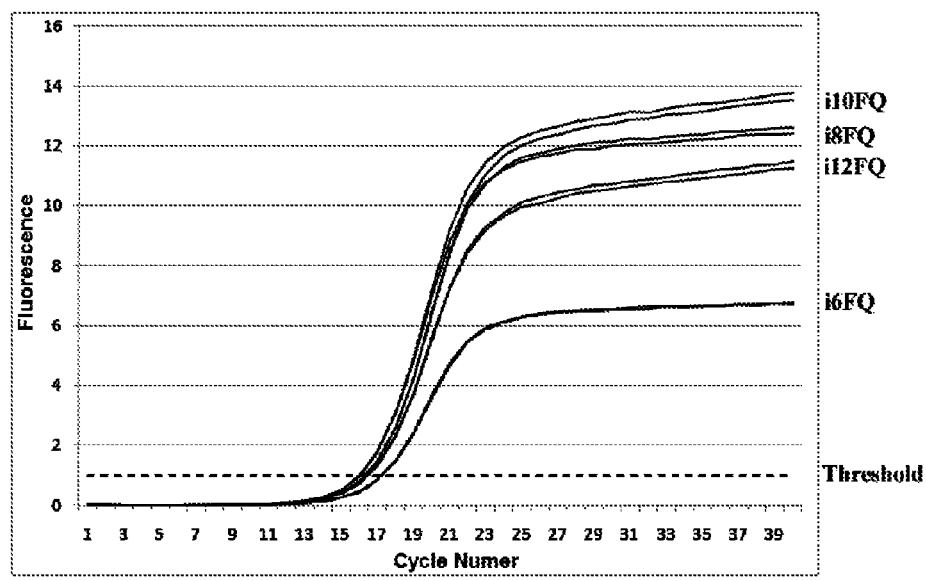
FIG. 3B is an amplification plot that illustrates baseline adjusted fluorescence of the data in FIG. 3A ($\Delta R_n$).

A series of oligonucleotide probes having a 5'-FAM reporter dye and an internal iFQ quencher were synthesized using the HPRT probe sequence varying the relative placement of the iFQ group. In one set the iFQ group was placed as a base substitution (replacing a base within the sequence). In another set the iFQ group was placed as a base insertion between residues. The distance of the iFQ from the 5'-dye was varied including 6, 8, 10, or 12 positions from the 5'-end. Henceforth, a modification placed as an insertion at position 6 is indicated as an "i6" and as a substitution at position 8 is indicated as a "s8", etc. The probes were used in qPCR as outlined above using the HPRT primers (SEQ ID Nos. 97 and 98) and $2\times10^6$ copies of a cloned HPRT amplicon plasmid target. Amplification plots for the substitution series probes (SEQ ID Nos. 100-103) are shown in FIG. 2A and baseline normalized plots are shown in FIG. 2B. Amplification plots for the insertion series (SEQ ID Nos. 104-107) are shown in FIG. 3A and baseline normalized plots are shown in FIG. 3B. It is clear that precise placement of the iFQ group within the probe affected probe characteristics, with changes seen in both the baseline fluorescence, magnitude of signal generation, and quantification cycle number (Cq, the cycle number where amplification signal is first detected).

Relative metrics for assessing probe quality from the amplification plots are reported in Table 7, including the baseline fluorescence measured in the qPCR device (as a measure of quenching efficiency) and the $\Delta R_E$, the difference in the fluorescence intensity between the start and end of the qPCR run (as a measure of the magnitude of signal generated). Having low baseline fluorescence coupled with high relative $\Delta R_n$ signal generation leads to improved probe performance.

The relative distance of the iFQ group from the 5'-FAM reporter dye had a significant impact on baseline fluorescence and on signal generation. In FIG. 3A, background fluorescence levels were i6<i8<i10<i12. Placing the quencher group closer to the reporter dye reduced background fluorescence. This effect was expected as FRET based quenching improves with the proximity of the reporter and quencher. Unexpectedly, the relative placement of the iFQ group also affected the magnitude of signal generation during an amplification run and final functional fluorescence (positive signal) was i10>i8>i12>>i6 (FIG. 3B). Interestingly, the i6 probes showed poor fluorescence signal for both the insertion and substitution series. This reduced signal compromised assay quality and delayed the Cq point for these probes, indicating lower assay sensitivity. We hypothesize that placing the iFQ group too close to the fluorophore results in probes that are not fully cleaved by the DNA polymerase during amplification (5'-nuclease assay format), resulting in decreased release of reporter dye from quencher. Peak probe performance is realized at a point which is a compromise between quenching, which improves as quencher and fluorophore are placed more closely, and cleavage, which improves as quencher and fluorophore are separated by a greater number of nucleic acid bases. The precise range where this relationship is optimal is non-obvious and may be different for different reporter dye/quencher combinations. For this reporter dye/quencher combination, optimum performance of the assay was seen with i8 and i10 placement. For these probes, background fluorescence was low and signal generation was high.

TABLE 7

Internal placement of iFQ in FAM labeled probes (HPRT assay)

| SEQ ID No. | Sequence | Baseline fluorescence | $\Delta R_n$ |
|---|---|---|---|
| | Sequence (Substitution) | | |
| 100 | FAM-ATGGTCAAGGT/iFQ/GCAAGCTTGCTGGT-SpC3 (s12) | 3.2 | 8.0 |
| 101 | FAM-ATGGTCAAG/iFQ/TCGCAAGCTTGCTGGT-SpC3 (s10) | 2.2 | 7.8 |
| 102 | FAM-ATGGTCA/iFQ/GGTCGCAAGCTTGCTGGT-SpC3 (s8) | 1.7 | 7.0 |
| 103 | FAM-ATGGT/iFQ/AAGGTCGCAAGCTTGCTGGT-SpC3 (s6) | 1.1 | 3.3 |
| | Sequence (Insertion) | | |
| 104 | FAM-ATGGTCAAGGT/iFQ/CGCAAGCTTGCTGGT-SpC3 (i12) | 6.0 | 11.6 |
| 105 | FAM-ATGGTCAAG/iFQ/GTCGCAAGCTTGCTGGT-SpC3 (i10) | 4.0 | 13.7 |
| 106 | FAM-ATGGTCA/iFQ/AGGTCGCAAGCTTGCTGGT-SpC3 (i8) | 2.0 | 12.5 |
| 107 | FAM-ATGGT/iFQ/CAAGGTCGCAAGCTTGCTGGT-SpC3 (i6) | 1.7 | 6.8 |

All probe designs functioned in the above qPCR assay, thus the iFQ group can be used in the methods of this disclosure as either a base substitution or as an insertion between bases. Placing the iFQ group as a base substitution resulted in slightly better quenching than when used as an insertion between bases, however as a group the substitution probes showed lower signal generation. Further, iFQ placed as a base substitution is slightly destabilizing (lowers $T_m$) whereas iFQ placed as a base insertion is stabilizing (increases $T_m$) (see Example 1 above). Given the better signal generation and improved duplex stabilization properties, placement of the iFQ as an insertion is considered to be a more preferred embodiment and all subsequent examples will be done using only iFQ insertion probes.

Example 5

The following example demonstrates the efficacy of the internal quencher probe design at varying target concentrations.

Example 4 examined the performance of 8 different probe designs using a single concentration of target nucleic acid. In the present example, six concentrations of target were tested in HPRT qPCR assays comparing performance of four of the probes from Example 4. HPRT specific probes using internal FQ (iFQ) quencher with FAM reporter were employed including substitution design s6 and s10 (SEQ ID Nos. 103 and 101) and insertion design i6 and i10 (SEQ ID Nos. 107 and 105). Amplification reactions were run as outlined in Example 3 using input target plasmid copy numbers of $2\times10^2$, $2\times10^3$, $2\times10^4$, $2\times10^5$, $2\times10^6$ and $2\times10^7$. Each reaction was run in triplicate.

Figure 4A:
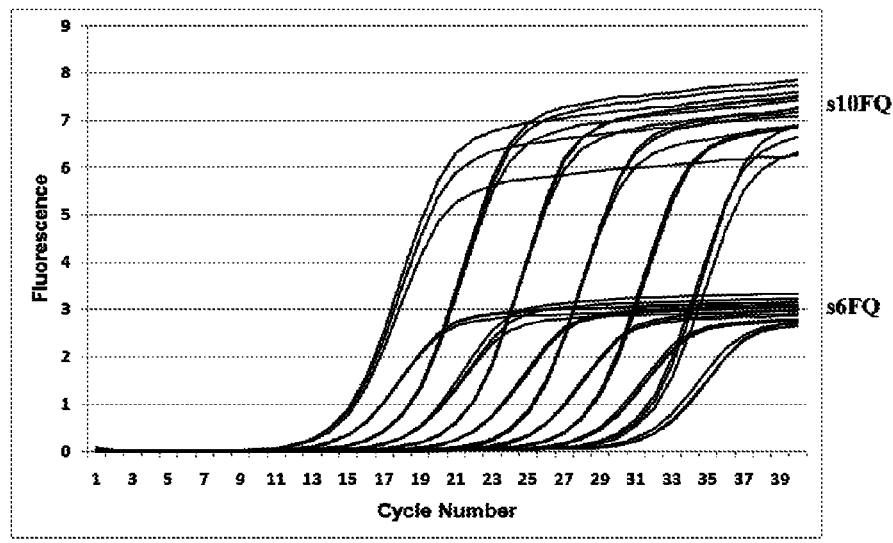
FIG. 4A is an amplification plot that shows the results of the baseline adjusted substitution analogs s10FQ and s6FQ and FIG. 4B is an amplification plot that shows the results for the baseline adjusted insertion analogs s10FQ and s6FQ where various plasmid copy target amounts ($2 \times 10^2$, $2 \times 10^3$, $2 \times 10^4$, $2 \times 10^5$, $2 \times 10^6$ and $2 \times 10^7$) were tested.
Figure 4B:
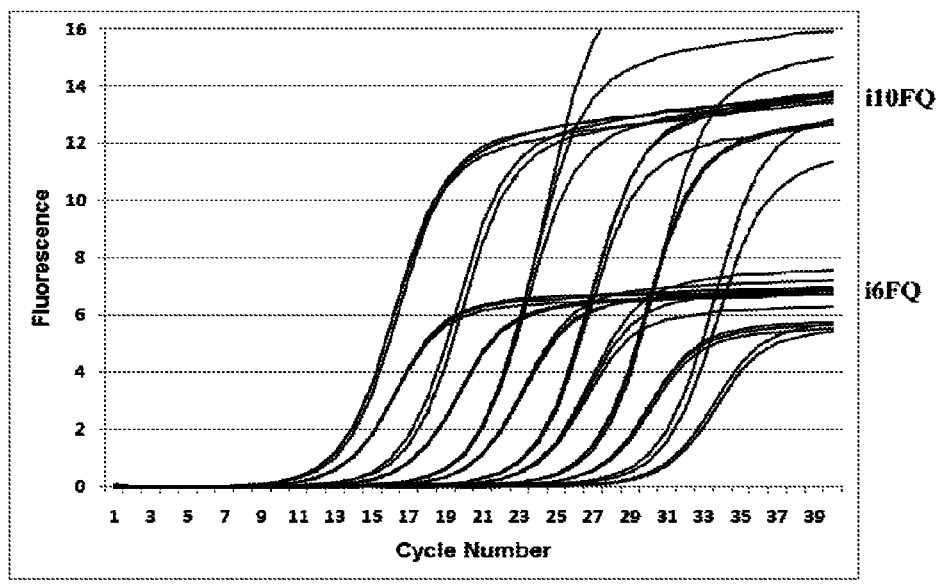

FIG. 4A shows the results of the baseline adjusted substitution set and FIG. 4B shows the results for the baseline adjusted insertion set. There is a clear progression of the amplification plot curves corresponding to the expected difference of ~3.3 cycles for every 10-fold change of input target nucleic acid, wherein the curves align from left to right the highest concentration of template to the lowest concentration. The insertion probe set outperformed the substitution probe set at all concentrations tested as evidenced by the improved magnitude of signal generated for all comparable data points. Further, the quencher i10 placement outperformed the quencher i6 placement series. Subsequent examples will therefore focus on use of the substitution i10 probe design.

Example 6

The following example demonstrates the use of an inserted internal quencher coupled with a second quencher positioned at the 3'-end of the probe.

A new series of probes were synthesized targeting the HPRT gene all having a 5'-fluorescein reporter dye (6-FAM) and having quenchers located at varying positions, including compositions having two quencher groups in the same probe molecule. Internal quenchers were added as insertions between bases. Single quencher probes (FQ quencher on the 3'-terminus, FQ quencher at the i10 position) were compared with dual quencher version of the same sequences. Dual quencher probes were made using the FQ chemical group or the Black Hole Quencher™-1 (BHQ1, shown below), a different commercially available dark quencher (Biosearch Technologies, Novato, Calif.). Table 8 lists the probe sequences tested. HPRT qPCR assays were performed as described in Example 4, using $2\times10^6$ copies of an HPRT amplicon-containing plasmid as target.

Figure 5A:
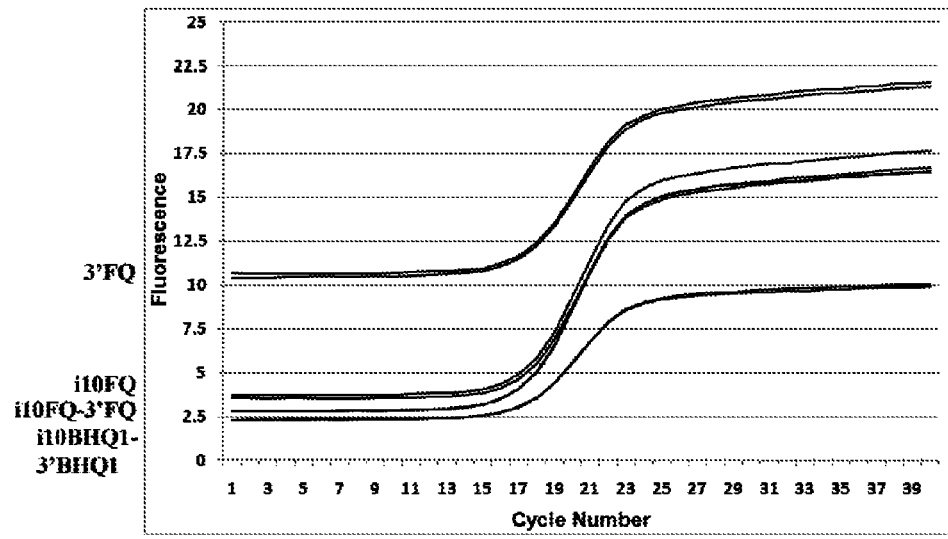
FIGS. 5A and 5B are amplification plots (baseline comparison ($R_n$) and baseline adjusted ($\Delta R_n$) comparison respectively) that demonstrate the improved performance of internal FQ (10) by itself or as a dual quenched probe compared to an internal BHQ1 (10) dual quenched probe.
Figure 5B:
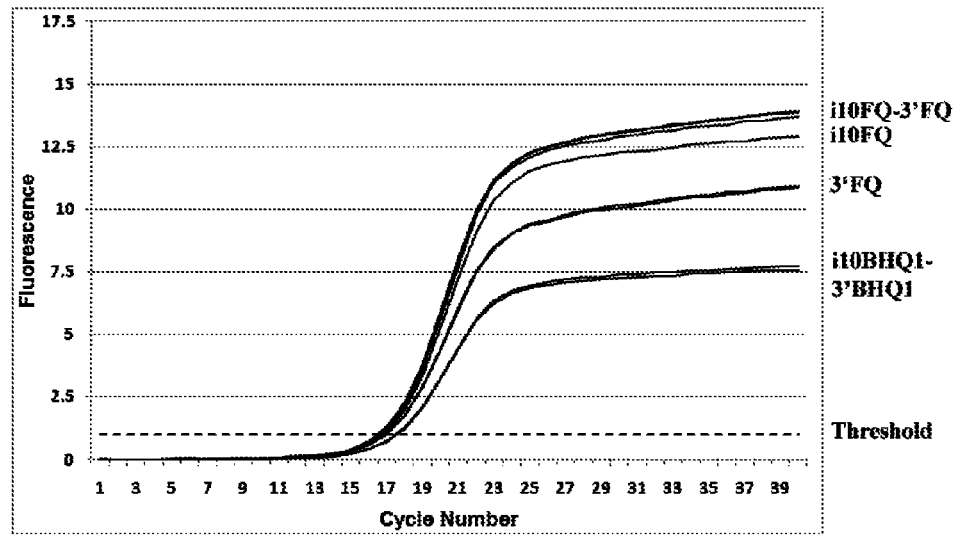

These four probes were used in qPCR as outlined in Example 4 above using the HPRT primers (SEQ ID Nos. 97 and 98) and $2\times10^6$ copies of a cloned HPRT amplicon plasmid target. Amplification plots are shown in FIG. 5A and baseline normalized plots are shown in FIG. 5B. Relative metrics for assessing probe quality from the amplification plots are also reported in Table 8, including the baseline fluorescence measured in the qPCR device (as a measure of quenching efficiency) and the $\Delta R_n$ seen between the start and end of the qPCR run (as a measure of the magnitude of signal generated). Having low baseline fluorescence coupled with high relative $\Delta R_n$ signal generation leads to improved probe performance.

The traditional probe design with a 5'-reporter dye and 3'-quencher (SEQ ID No. 108) showed the highest baseline fluorescence (i.e., worst quenching). The single quencher internal i10 placement probe (SEQ ID No. 105) showed significantly lower baseline fluorescence and the dual-quencher probes (SEQ ID Nos. 109, 110) showed the lowest baseline fluorescence (i.e., best quenching). Thus the dual quencher probes in FIGS. 5A and 5B showed slightly better performance than the i10FQ quencher alone, demonstrating that the presence of two quenchers not only does not negatively affect their quenching properties but rather improves the overall quenching properties.

The relative fluorescence signal generated using the different probe designs also varied with quencher type and placement. The three FQ probes generated a $\Delta R_n$ of 11-14 with the highest relative fluorescent signal produced by the dual-quencher i10FQ-3'-FQ probe (SEQ ID No. 109). Interestingly, the same design using the alternative commercial dark quencher BHQ-1 (SEQ ID No. 110) performed significantly worse, showing a $\Delta R_n$ of only 7.5. This probe also showed a delayed Cq value (the cycle number where amplification signal is first detected), indicating worse functional sensitivity. This clearly demonstrates that all dark quencher chemical

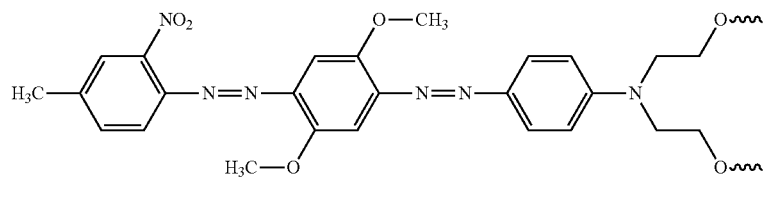

BHQ1

TABLE 8

Single and Dual Quenched Probes

| SEQ ID No. | Probe Name | Sequence | Baseline fluorescence | $\Delta R_n$ |
|---|---|---|---|---|
| 105 | i10FQ | FAM-ATGGTCAAG/iFQ/GTCGCAAGCTTGCTGGT-SpC3 | 4.0 | 12.7 |
| 108 | 3'FQ | FAM-ATGGTCAAGGTCGCAAGCTTGCTGGT-FQ | 10.5 | 11.0 |
| 109 | i10FQ +3'FQ | FAM-ATGGTCAAG/iFQ/GTCGCAAGCTTGCTGGT-FQ | 2.6 | 14.0 |
| 110 | i10BHQ +3'BHQ | FAM-ATGGTCAAG/iBHQ1/GTCGCAAGCTTGCTGGT-BHQ1 | 2.5 | 7.5 | compositions are not functionally interchangeable and that the napthylene-azo quencher (FQ) performs in a superior fashion using the methods of this disclosure.

Example 7

Examples 4, 5, and 6 were performed using a single probe sequence specific for the human HPRT gene. The following example illustrates that the functional qPCR results detailed in Examples 4-6 are consistent when run using a different probe sequence, for a different target gene, using a different thermal cycler platform and different reagents.

A new qPCR assay was employed specific for a strain of the H1N1 Influenza virus (SW H1, also known as the "swine flu"). Primer and probe sequences and are listed below in Table 9.

TABLE 9

Sequences used in an Influenza qPCR assay

| SEQ ID No. | Sequence Name | Sequence |
|---|---|---|
| 111 | SW H1 Forward | GTGCTATAAACACCAGCCTYCCA |
| 112 | SW H1 Reverse | CGGGATATTCCTTAATCCTGTRGC |
| 113 | SW H1 Probe | CAGAATATACATCCAGTCACAATTGGAAAA |

A set of Influenza virus H1N1 specific (SW H1) probes were synthesized and qPCR assays were performed using the same methods as described in Example 4 except that the assays were run on an Applied Biosystems 7900HT Sequence Detection System (Applied Biosystems, Foster City, Calif.) according to manufacturer's instructions, using 1× TaqMan Gene Expression Master Mix (Life Technologies, Carlsbad, Calif.), 250 nM probe and 1000 nM primers per the Center for Disease Control (CDC) document (CEC REF#1-007-005 Protocol for Detection and Characterization of Swine Influenza, 2009) recommendations. Assays run using different probe sequences and targets in the present example demonstrate that the performance of the probes of this disclosure are not sequence dependent, instrument dependent or polymerase formulation dependent.

The assays were run in duplicate with 2×10⁶ copies of plasmid target used. Table 10 lists the probe sequences tested. All internal quencher groups were placed as insertions. Relative metrics for assessing probe quality from the amplification plots are also reported in Table 10, including the baseline fluorescence measured in the qPCR device (as a measure of quenching efficiency) and the $\Delta R_n$ seen between the start and end of the qPCR run (as a measure of the magnitude of signal generated). Note that the numbers reported are "relative fluorescence units" and that this example was performed on a different machine than the plots shown in Examples 4-6 above. The absolute numbers are different between machines; however the relative performance of the various probe designs is directly comparable.

TABLE 10

Single and dual quenched influenza SW H1 assays

| SEQ ID No. | Name | Sequence | Baseline | $\Delta R_a$ |
|---|---|---|---|---|
| 114 | 3'FQ | FAM-CAGAATATACATCCAGTCACAATTGGAAAA-FQ | 2.6 | 1.5 |
| 115 | i10FQ | FAM-CAGAATATA/iFQ/CATCCAGTCACAATTGGAAAA-SpC3 | 0.7 | 2.4 |
| 116 | iF10Q+3'FQ | FAM-CAGAATATA/iFQ/CATCCAGTCACAATTGGAAAA-FQ | 0.6 | 2.9 |
| 117 | i10BHQ1+3'BHQ1 | FAM-CAGAATATA/iBHQ1/CATCCAGTCACAATTGGAAAA-BHQ1 | 0.45 | 0.8 |

Figure 6A:
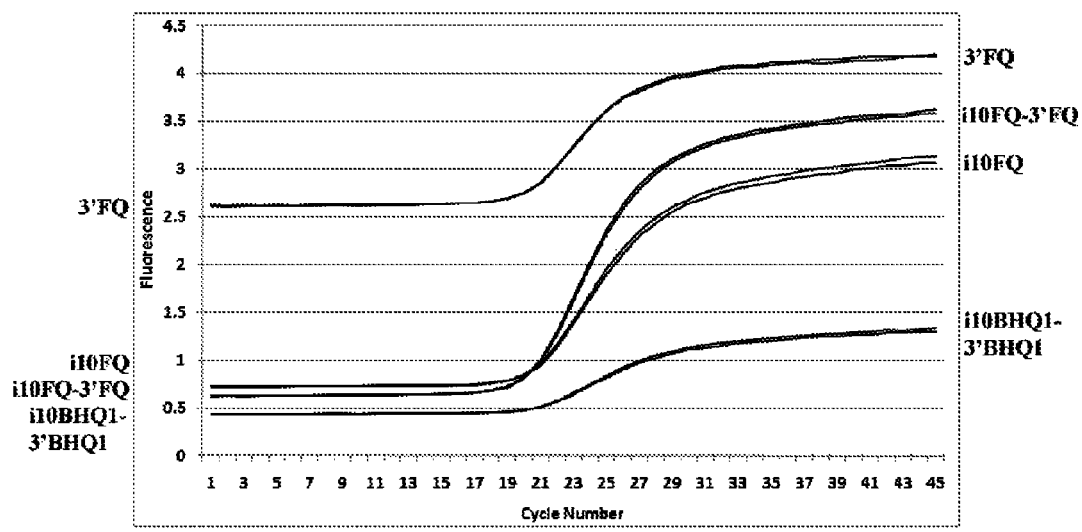
FIGS. 6A and 6B are amplification plots (baseline comparison ($R_n$) and baseline adjusted ($\Delta R_n$) respectively) that demonstrate the increased performance of internal FQ (iFQ) by itself or as a dual quenched containing probes compared to internal BHQ1 (iBHQ1) dual quenched probe using a different probe sequence.
Figure 6B:
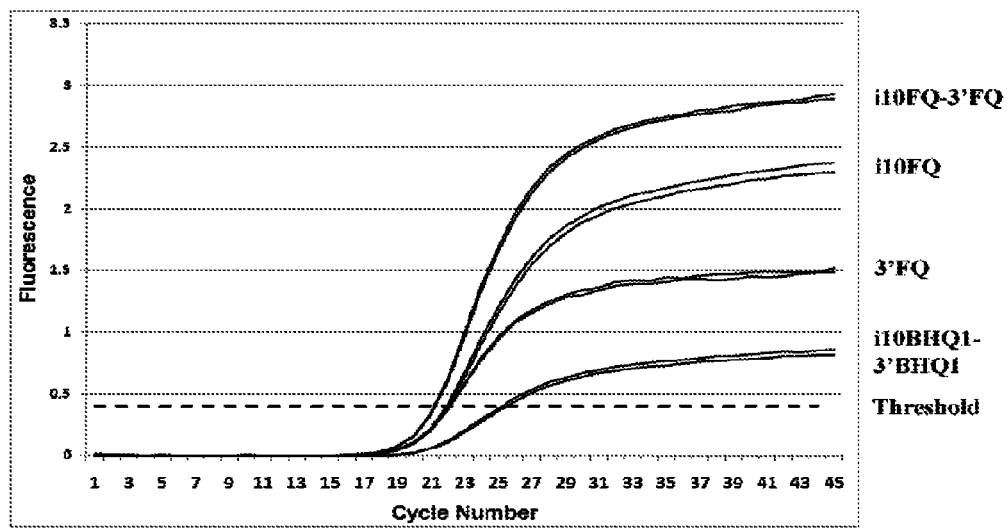

Amplification plots for the influenza qPCR assays are shown in FIG. 6A and baseline normalized amplification plots are shown in FIG. 6B. Similar to the results described in Example 6 for the HPRT assays, the probe containing the 3'FQ quencher alone did not perform as well as any of the internal FQ containing probes. In particular, the internal-quencher probes showed markedly lower baseline (background) fluorescence, with the dual-quencher probes having the lowest background. As before, the dual quencher probes outperformed the single quencher probes, with the iFQ+3'FQ combination working the best. The SWH1 probe is 30 bases long and represents a relatively long probe sequence for use as a dual-quenched probe in hydrolysis assays, which contributes to the greater difference seen between 3'-quencher probes and internal quencher probes in this example compared with the HPRT probes in Example 6 (the HPRT probe is 26 bases long). This illustrates another benefit of the methods of this disclosure. Long probes (as are frequently required in AT-rich target sequences) perform poorly using 3'-quencher design; however probe length does not affect performance of internally quenched probes.

Similar to the results observed in Example 6 above, the dual-quencher i10FQ+3'FQ probe performed the best of the set tested, showing both low baseline fluorescence and high positive signal strength. Of note, again in the influenza probe sequence context the dual-quencher i10BHQ1+3'BHQ1 probe showed low baseline fluorescence with very low signal strength and functioned poorly in the assay, showing a delayed Cq value relative to the other probes.

Example 8

The following example demonstrates the efficacy of the internal quencher probes of the present disclosure when used with various fluorophores.

In previous examples, all probes contained a 5'-fluorescein reporter dye (6-FAM). Typically, quencher molecules perform well with a limited subset of reporter dyes that are matched such that the fluorophore fluorescence emission wavelength overlaps well with the absorbance wavelengths of the quencher. A dye with emission in the red region, such as Cy5, typically requires use of a different quencher than one that is useful with a dye that has a shorter wavelength emission spectra, such as fluorescein. The probes in this example comprise different fluorophores having a wide range of emission wavelengths (Table 10) and demonstrate that the use of internal quencher probes in the dual-quencher format function well across a wide spectral range. All probes in the present example place the iFQ quencher at position i10 as an insertion. The dual-quencher probes of the present example are made using the i10FQ combined with either a 3'-FQ or with a 3'-IB RQ-n1 (also referred to as "RQ"). In traditional single 3'-quencher probe format, the FQ quencher (which has a peak absorbance around 534 nm) is typically employed with reporter dyes having emission in the 500-580 nm wavelength range. The RQ quencher (which has a bimodal peak absorbance around 610 and 640 nm) is typically employed with reporter dyes having emission in the 550-700 nm wavelength range.

TABLE 10

Fluorescent reporter dyes and their excitation and emission wavelengths.

| Dye | Excitation Max (nm) | Emission Max (nm) |
|---|---|---|
| 6-FAM | 495 | 520 |
| MAX | 524 | 557 |
| Cy3 | 550 | 564 |
| TEX-615 | 596 | 615 |
| Cy5 | 648 | 668 |

A series of dual quencher probes specific for the human HPRT gene were synthesized having an insertion of the FQ quencher at the i10 position and either a 3'-FQ or a 3'-RQ quencher. Probe sequences are shown in Table 11 below. The probes were used in qPCR as described in Example 4 above using the HPRT primers (SEQ ID Nos. 97 and 98) and 2×10$^6$ copies of a cloned HPRT amplicon plasmid target. The FAM and MAX probes were run using the Applied Biosystems AB7900HT Sequence Detection platform. The Cy3 probes were run using the BIO-RAD iQ5 platform. The TEX615 and Cy5 probes were run using the Roche LightCycler 480 platform.

Figure 7A:
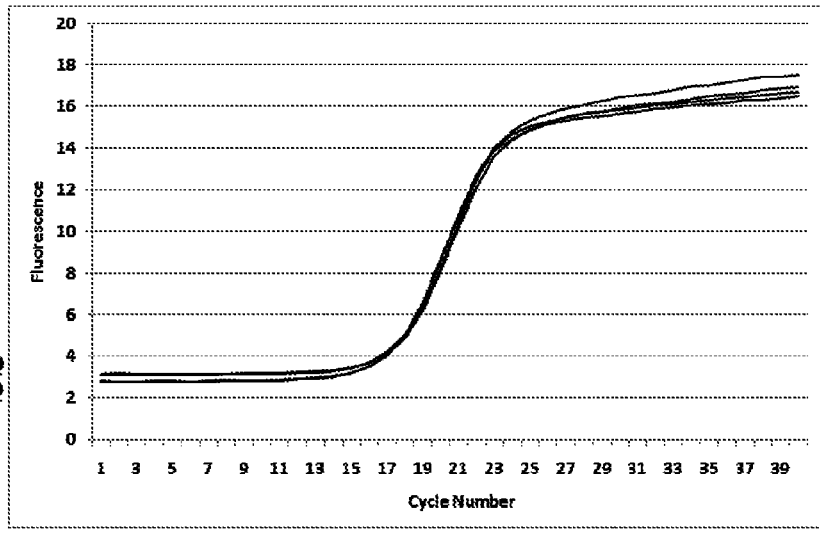
FIGS. 7A and 7B are amplification plots (baseline comparison ($R_n$) and baseline adjusted comparison ($\Delta R_n$) respectively) using an AB 7900HT instrument comparing a 5' FAM labeled dual quencher probes iFQ-3'FQ and iFQ-3'RQ-n1, illustrating the enhanced performance of an internally quenched probe in conjunction with a different 3' end quencher.
Figure 7B:
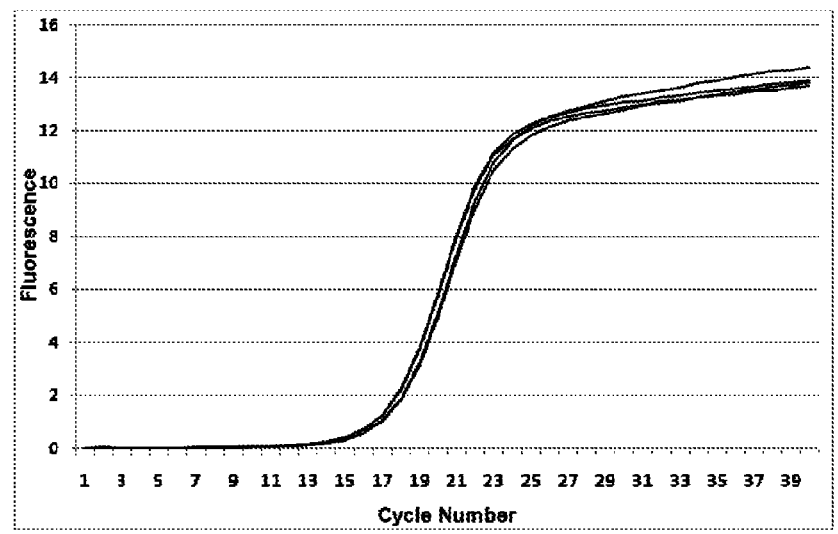

Examples 6 and 7 demonstrated that the dual-quencher iFQ-3'FQ combination performed slightly better for FAM reporter dye probes than iFQ alone, although the single quencher iFQ probes also performed well. Amplification plots for the fluorescein (emission 520 nm) reporter dye probes (SEQ ID Nos. 109 and 118) are shown in FIG. 7A and baseline normalized plots are shown in FIG. 7B. In this comparison, performance is nearly identical for the i10FQ-3'FQ vs. i10FQ-3'RQ probes, even though the RQ quencher is best suited for red wavelength dyes. The i10FQ-3'FQ probe did, however, perform slightly better.

Figure 8A:
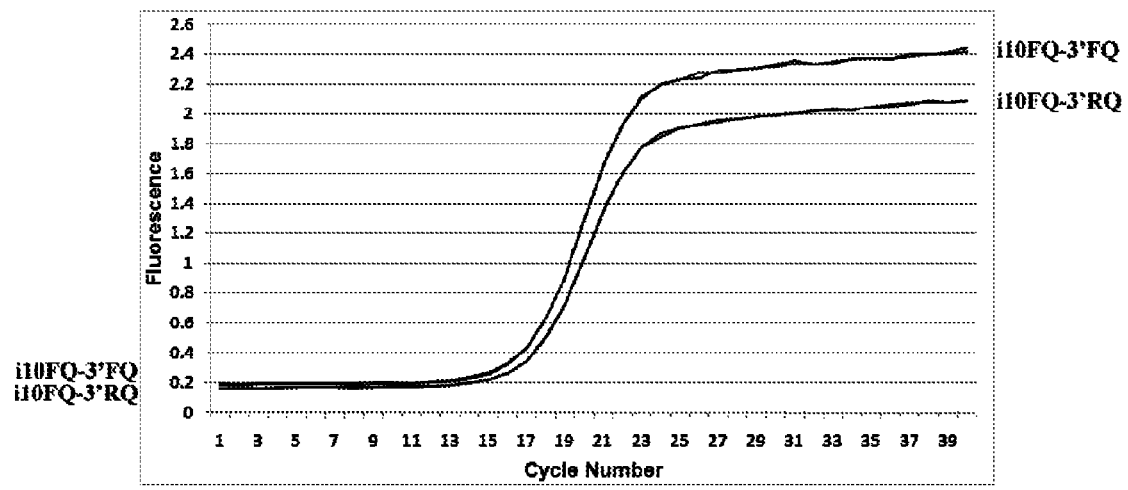
FIGS. 8A and 8B are amplification plots (baseline comparison ($R_n$) and baseline adjusted comparison ($\Delta R_n$) respectively) using an AB 7900HT instrument comparing a 5' MAX labeled dual quencher probes iFQ-3'FQ and iFQ-3'RQ-n1, illustrating the enhanced performance of an internally quenched probe in conjunction with a different 3' end quencher.
Figure 8B:
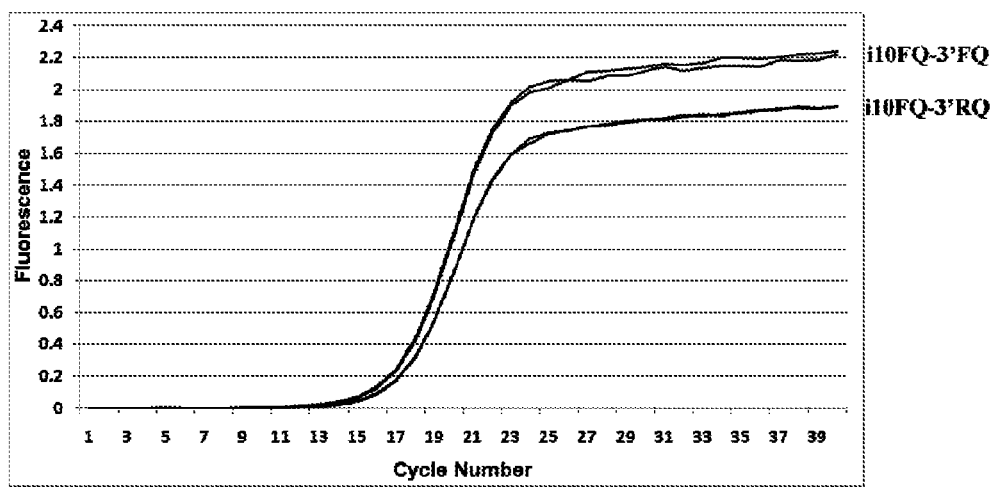

Amplification plots for the MAX (emission 557 nm) reporter dye probes (SEQ ID Nos. 119 and 120) are shown in FIG. 8A and baseline normalized plots are shown in FIG. 8B. Baseline quenching was nearly identical for the i10FQ-3'FQ vs. i10FQ-3'RQ probes, however peak signal intensity was superior with the i10FQ-3'FQ probe. Both designs worked well but the i10FQ-3'FQ design is preferred.

Figure 9A:
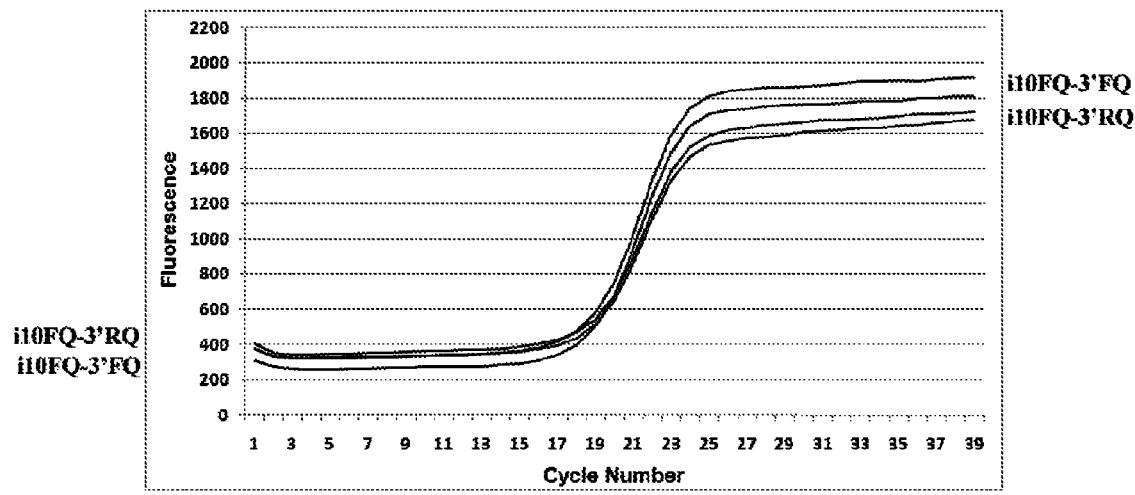
FIGS. 9A and 9B are amplification plots (baseline comparison ($R_n$) and baseline adjusted comparison ($\Delta R_n$) respectively) using an iQ5 BioRad instrument comparing a CY3 labeled dual quencher probes iFQ-3'FQ and iFQ-3'RQ-n1, illustrating the enhanced performance of an internally quenched probe in conjunction with a different 3' end quencher.
Figure 9B:
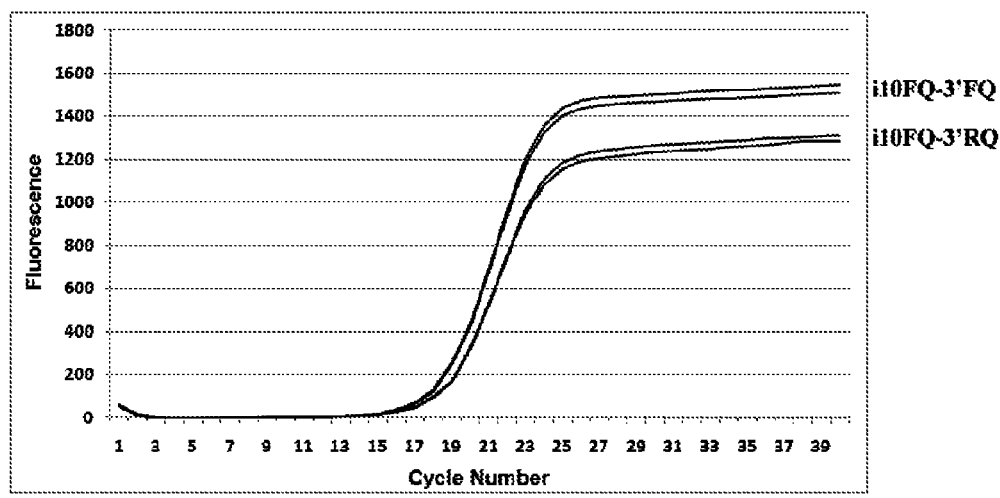

Amplification plots for the Cy3 (emission 564 nm) reporter dye probes (SEQ ID Nos. 121 and 122) are shown in FIG. 9A and baseline normalized plots are shown in FIG. 9B. Baseline quenching was slightly lower for the i10FQ-3'FQ vs. i10FQ-3'RQ probes, and peak signal intensity was also slightly superior with the i10FQ-3'FQ probe. Both designs worked well but the i10FQ-3'FQ design is preferred.

Figure 10A:
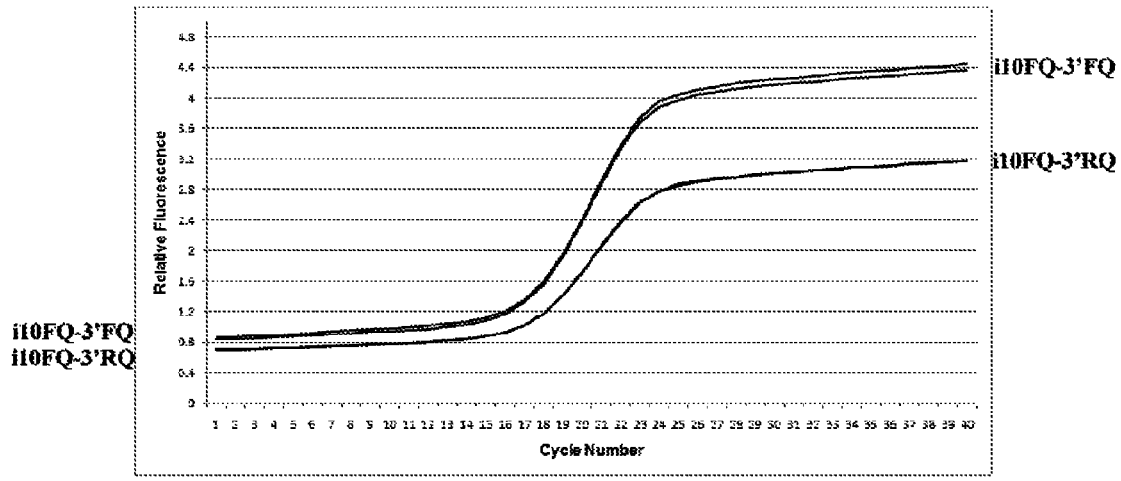
FIGS. 10A and 10B are amplification plots (baseline comparison ($R_n$) and baseline adjusted comparison ($\Delta R_n$) respectively) using a LC480 Roche instrument comparing a 5'TEX615 labeled dual quencher probes iFQ-3'FQ and iFQ-3'RQ-n1, illustrating the enhanced performance of an internally quenched probe in conjunction with a different 3' end quencher.
Figure 10B:
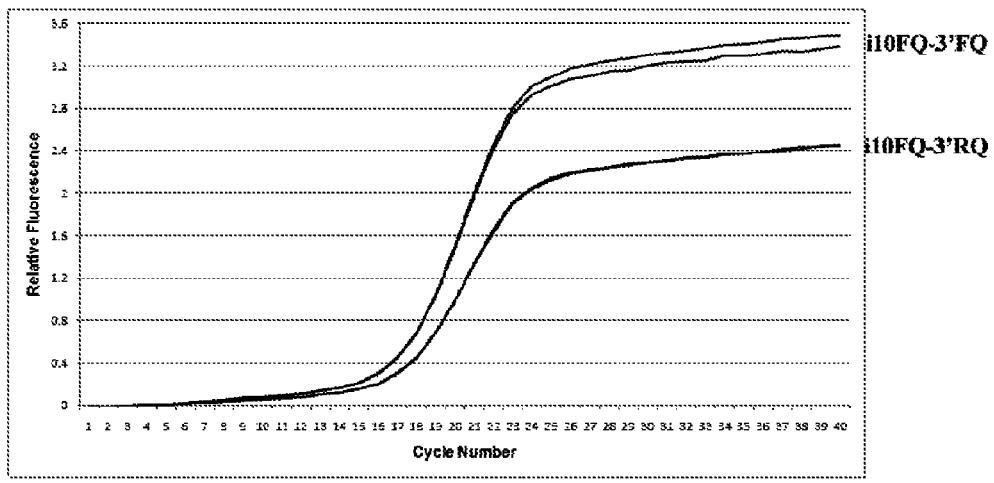

Amplification plots for the TEX615 (emission 615 nm) reporter dye probes (SEQ ID Nos. 123 and 124) are shown in FIG. 10A and baseline normalized plots are shown in FIG. 10B. Baseline quenching was slightly lower for the i10FQ-3'RQ vs. i10FQ-3'FQ probes, however peak signal intensity was superior with the i10FQ-3'FQ probe. Both designs worked well but the i10FQ-3'FQ design is preferred.

Figure 11A:
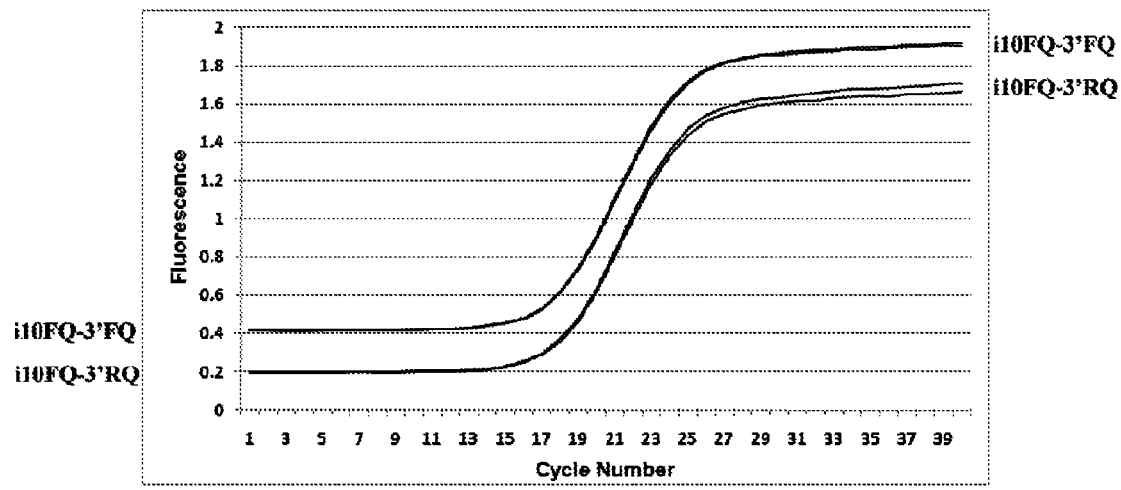
FIGS. 11A and 11B are amplification plots (baseline comparison ($R_n$) and baseline adjusted comparison ($\Delta R_n$) respectively) using a LC480 Roche instrument comparing a 5' CY5 labeled dual quencher probes iFQ-3'FQ and iFQ-3'RQ-n1, illustrating the enhanced performance of an internally quenched probe in conjunction with a different 3' end quencher.
Figure 11B:
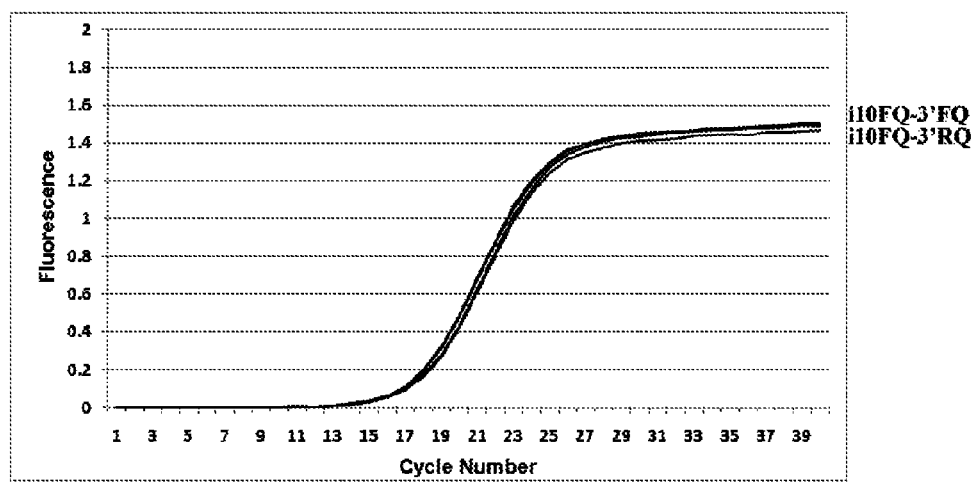

Amplification plots for the Cy5 (emission 668 nm) reporter dye probes (SEQ ID Nos. 125 and 126) are shown in FIG. 11A and baseline normalized plots are shown in FIG. 11B. Baseline quenching was lower for the i10FQ-3'RQ vs. i10FQ-3'FQ probes; however peak signal intensity was identical for both designs. Both designs worked well but the i10FQ-3'RQ design showed lower baseline fluorescence.

The relative metrics for assessing probe quality from the amplification plots are also reported in Table 12, including the baseline fluorescence measured in the qPCR device (as a measure of quenching efficiency) and the $\Delta R_n$ seen between the start and end of the qPCR run (as a measure of the magnitude of signal generated). Having low baseline fluorescence coupled with high relative $\Delta R_n$ signal generation leads to improved probe performance. Note that different real-time PCR machines were employed for different probe pairs (see above) and that the arbitrary fluorescence units reporting fluorescence intensity vary between platforms.

TABLE 12

Dual-quencher probes with various reporter dyes and an internal i10FQ with either 3'-FQ or 3'-RQ

| SEQ ID No. | Name | Sequence | Baseline fluorescence | $\Delta R_a$ |
|---|---|---|---|---|
| 109 | FAM i10FQ-3'FQ | FAM-ATGGTCAAG/iFQ/GTCGCAAGCTTGCTGGT-FQ | 2.9 | 14 |
| 118 | FAM i10FQ-3'RQ | FAM-ATGGTCAAG/iFQ/GTCGCAAGCTTGCTGGT-RQ | 3.1 | 13.8 |
| 119 | MAX i10FQ-3'FQ | MAX-ATGGTCAAG/iFQ/GTCGCAAGCTTGCTGGT-FQ | 0.2 | 2.1 |
| 120 | MAX i10FQ-3'RQ | MAX-ATGGTCAAG/iFQ/GTCGCAAGCTTGCTGGT-RQ | 0.2 | 1.9 |
| 121 | Cy3 i10FQ-3'FQ | Cy3-ATGGTCAAG/iFQ/GTCGCAAGCTTGCTGGT-FQ | 350 | 1500 |

TABLE 12-continued

Dual-quencher probes with various reporter dyes and an internal i10FQ with either 3'-FQ or 3'-RQ

| SEQ ID No. | Name | Sequence | Baseline fluorescence | $\Delta R_a$ |
|---|---|---|---|---|
| 122 | Cy3 i10FQ-3'RQ | Cy3-ATGGTCAAG/iFQ/GTCGCAAGCTTGCTGGT-RQ | 250 | 1300 |
| 123 | TEX i10FQ-3'FQ | TEX-ATGGTCAAG/iFQ/GTCGCAAGCTTGCTGGT-FQ | 0.8 | 3.4 |
| 124 | TEX i10FQ-3'RQ | TEX-ATGGTCAAG/iFQ/GTCGCAAGCTTGCTGGT-RQ | 0.7 | 2.4 |
| 125 | Cy5 i10FQ-3'FQ | Cy5-ATGGTCAAG/iFQ/GTCGCAAGCTTGCTGGT-FQ | 0.4 | 1.5 |
| 126 | Cy5 i10FQ-3'RQ | Cy5-ATGGTCAAG/iFQ/GTCGCAAGCTTGCTGGT-RQ | 0.2 | 1.5 |

The use of an internal quencher paired with a 3'-quencher in the above dual-quencher probes enables use of a single quencher compound (FQ) in probes with reporter dyes ranging from FAM to Cy5. This novel format thus permits use of a quencher with dyes that it is not suitable to work with when used in the traditional 3'-quencher alone probe design format.

Example 9

The following example demonstrates that placement of the internal iFQ insertion can vary with the Cy5 reporter dye.

The probes studied in Example 8 all employed the FQ quencher placed as an insertion at position i10. This example compares function of a dual-quenched Cy5 probes having i10FQ vs. i12FQ.

Probe sequences are shown in Table 13 below. The probes were used in qPCR as described in Example 4 above using the HPRT primers (SEQ ID Nos. 97 and 98) and $2 \times 10^7$ to $2 \times 10^2$ copies of a cloned HPRT amplicon plasmid target. The Cy5 probes were run using the Roche LightCycler 480 platform.

TABLE 13

Dual-quencher probes with Cy5 reporter dye comparing i10FQ vs. i12FQ

| SEQ ID No. | Name | Sequence |
|---|---|---|
| 125 | Cy5 i10FQ-3'FQ | Cy5-ATGGTCAAG/iFQ/GTCGCAAGCTTGCTGGT-FQ |
| 127 | Cy5 i12FQ-3'FQ | Cy5-ATGGTCAAGGT/iFQ/CGCAAGCTTGCTGGT-RQ |

Figure 12:
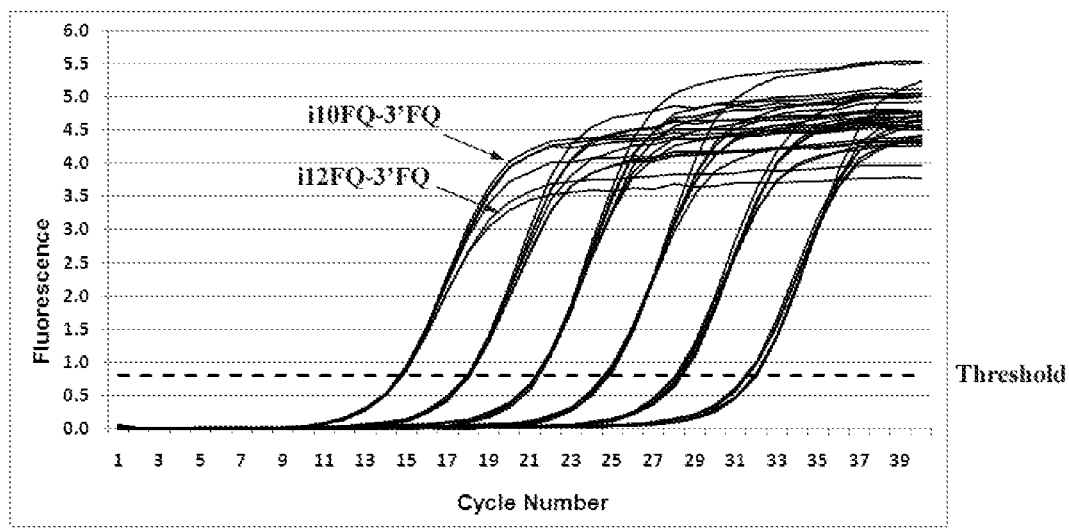
FIG. 12 is a side by side baseline adjusted amplification plot ($\Delta R_n$) where various plasmid copy target amounts ($2 \times 10^2$, $2 \times 10^3$, $2 \times 10^4$, $2 \times 10^5$, $2 \times 10^6$, $2 \times 10^7$) were tested for CY5 labeled dual quenched probes with the internal placement of the FQ quencher is between bases 9 and 10, versus 11-12, illustrating the ability to vary the positioning with the internal quencher.
Figure 13A:
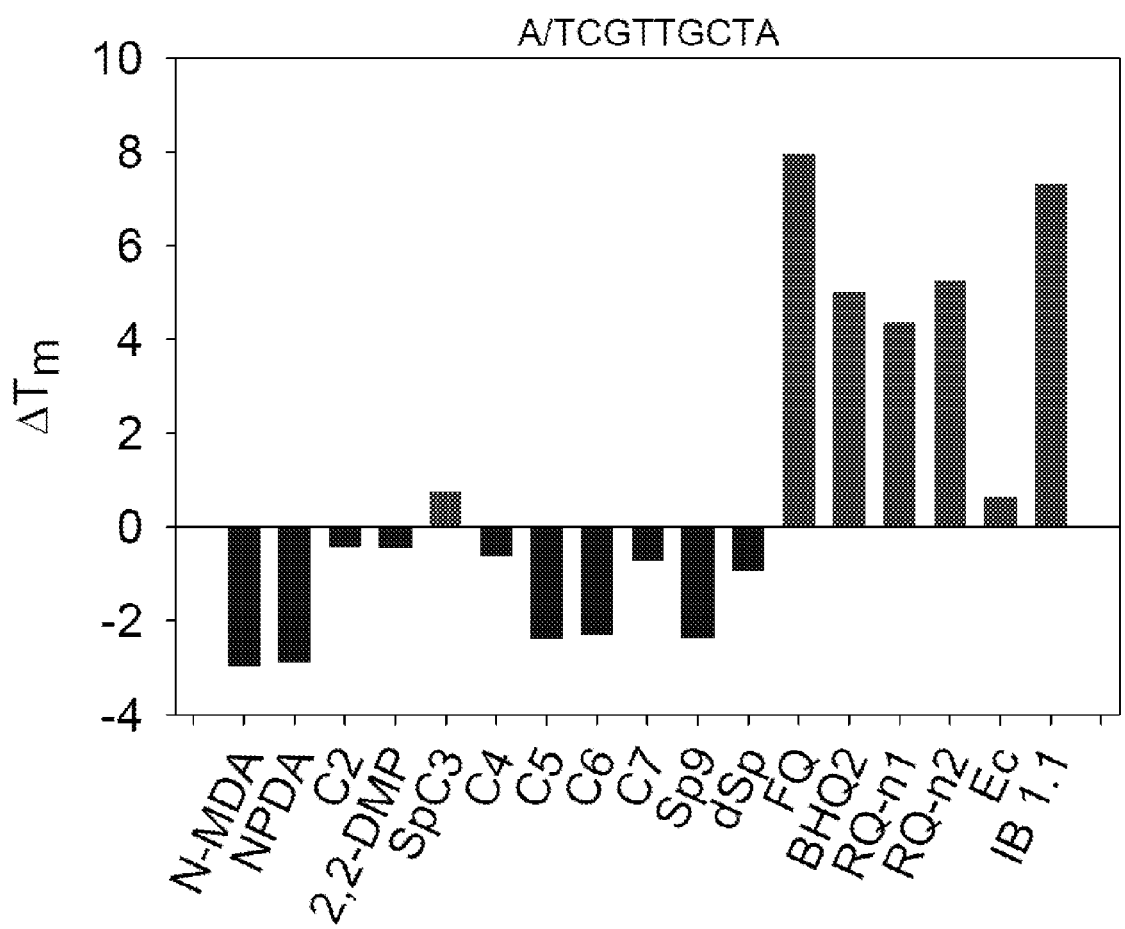
FIGS. 13A, 13B, 13C, 13D and 13E are bar charts showing the $\Delta T_m$ caused by modifying an oligonucleotide by inserting a modification compound between various nucleotides.
Figure 13B:
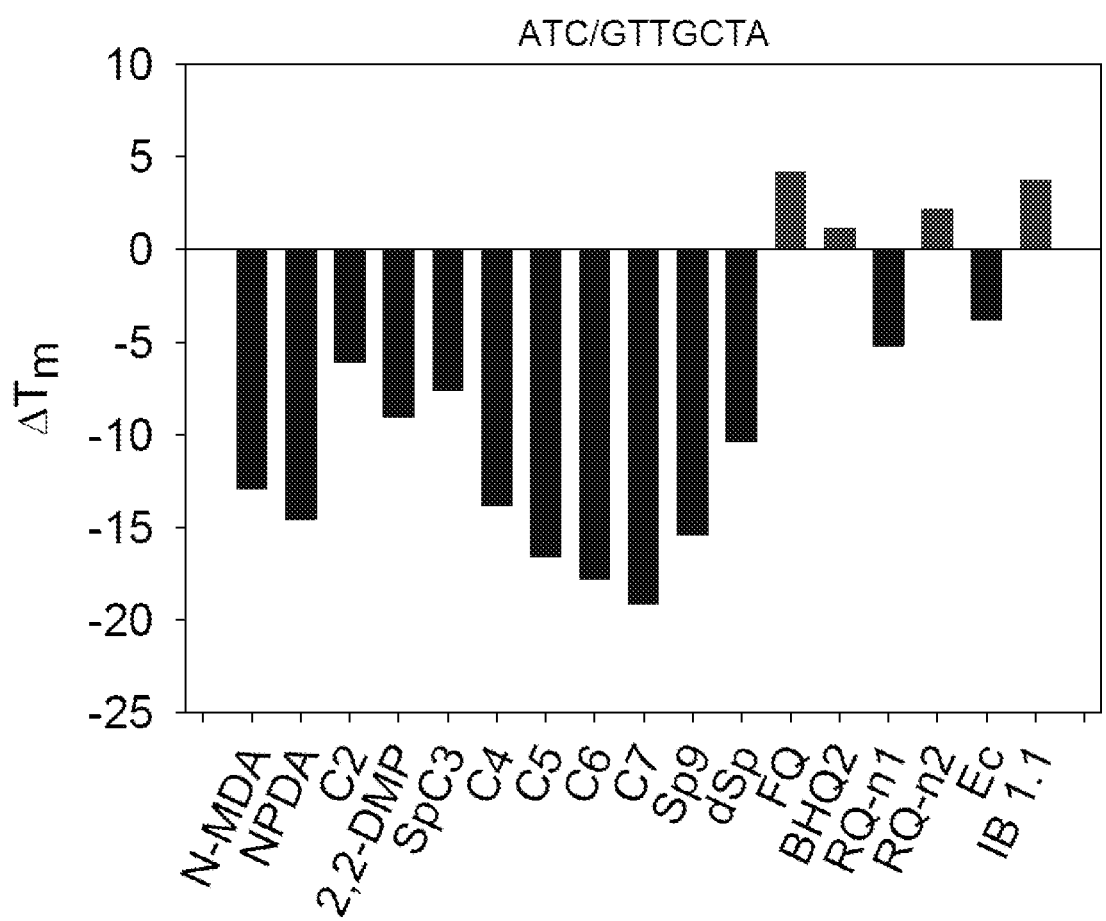
Figure 13C:
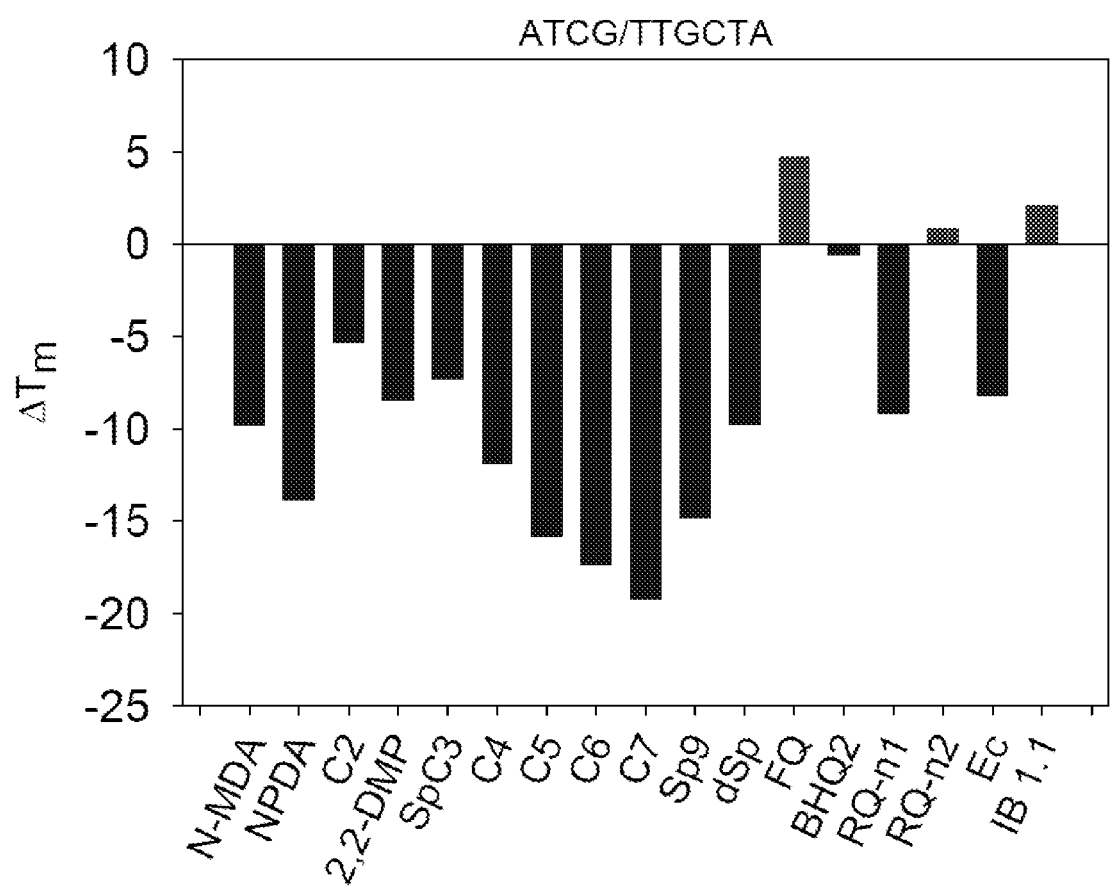
Figure 13D:
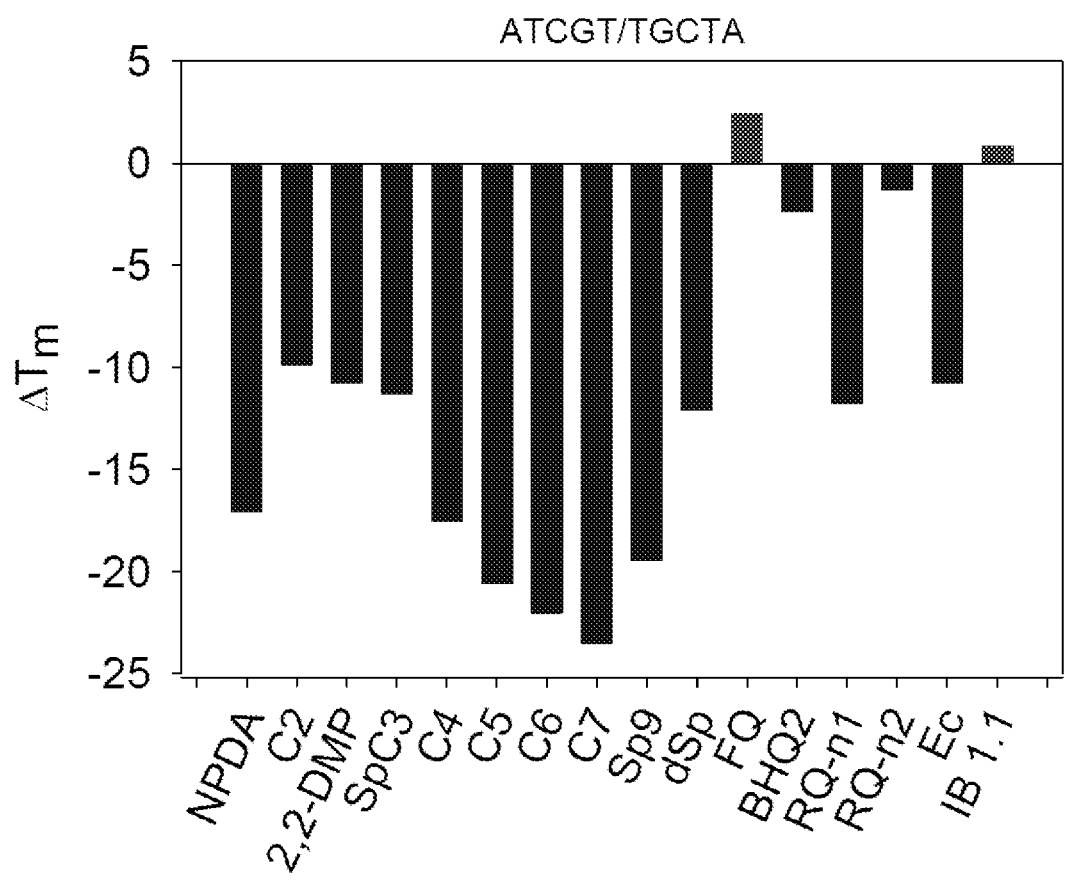
Figure 13E:
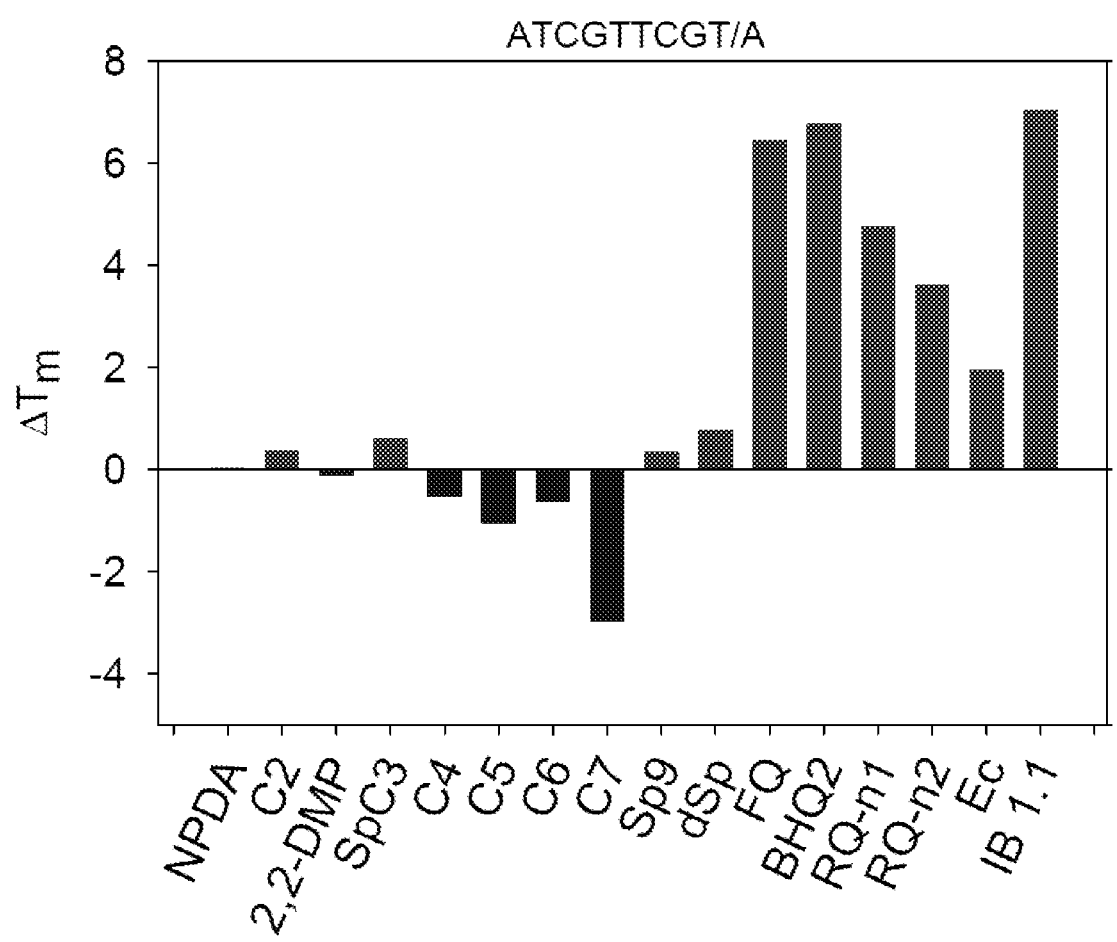

The baseline adjusted amplification plot showing superimposed traces of all 6 dilution curves for both probes is shown in FIG. 12. Peak signal intensity was slightly superior for the i10FQ-3'FQ probe than for the i12FQ-3'FQ probe, however both probes performed equally well in quantitative detection of the target standard curve dilution set. Precise Cq values measured for each probe/target dilution are shown in Table 14 below, where it can be seen that the Cq values are nearly identical between the two probes.

TABLE 14

Cq values comparing sensitivity of i10FQ-3'FQ vs. i12FQ-3-FQ for an HPRT assay using Cy5 reporter dye

| Copy Number | CY5 i10FQ-3'FQ | CY5 i12FQ-3'FQ |
|---|---|---|
| 2E7 | 14.2 | 14.4 |
| 2E6 | 17.5 | 17.4 |
| 2E5 | 20.9 | 21.0 |
| 2E4 | 24.8 | 24.6 |
| 2E3 | 28.0 | 27.9 |
| 2E2 | 31.6 | 32.4 |

Although there may be range in location for placement of the iFQ insertion for different probes, the preferred location may vary with different reporter dyes. More importantly, there exists some flexibility in placement such that iFQ group place anywhere in the i8-i12 range should work well.

Example 10

This example demonstrates the synthesis of a phosphoramidite useful for oligonucleotide synthesis that is derivatized with a quencher of the present disclosure. The synthetic method is shown below in Schemes 1 and 2.

Mono-DMT-phenyl diethanolamine (2)

A solution of 10 g of phenyl diethanolamine in 100 mL of pyridine was mixed for 3-4 h at room temperature with a solution of 6 g dimethoxytrityl-chloride (DMT-Cl) in 150 mL of a 98:2 dichloromethane/pyridine solution. The reaction mixture was concentrated to dryness under vacuum. The residue was dissolved in 200 mL of ethyl acetate, washed with two portions of 100 mL of deionized water, and the organic layer dried over $Na_2SO_4$. The organic solution was concentrated and purified by column chromatography using a 300 g of silica gel column developed with 30/65/5 ethyl acetate/hexanes/triethylamine to yield 5.25 g (20% yield) of mono-DMT-phenyl diethanolamine. TLC: $R_f$ 0.55 (EtAc/hexanes/$Et_3N$—40/55/5). $^1H$ NMR ($CDCl_3$) δ 7.38 (d, J=8 Hz, 2H), 7.27 (d, J=8 Hz, 4H), 7.38 (d, J=8 Hz, 2H), 7.24-7.12 (m, 6H), 6.76 (d, J=8 Hz, 4H), 6.66 (d, J=8 Hz, 2H), 3.74 (s, 6H), 3.74 (t, J=7.5 Hz, 2H), 3.54 (t, J=7.5 Hz, 2H), 3.51 (t, J=7.5 Hz, 2H), 3.33 (t, J=7.5 Hz, 2H), 2.23 (br. s, 1H).

Scheme 1

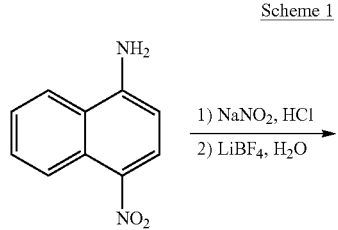

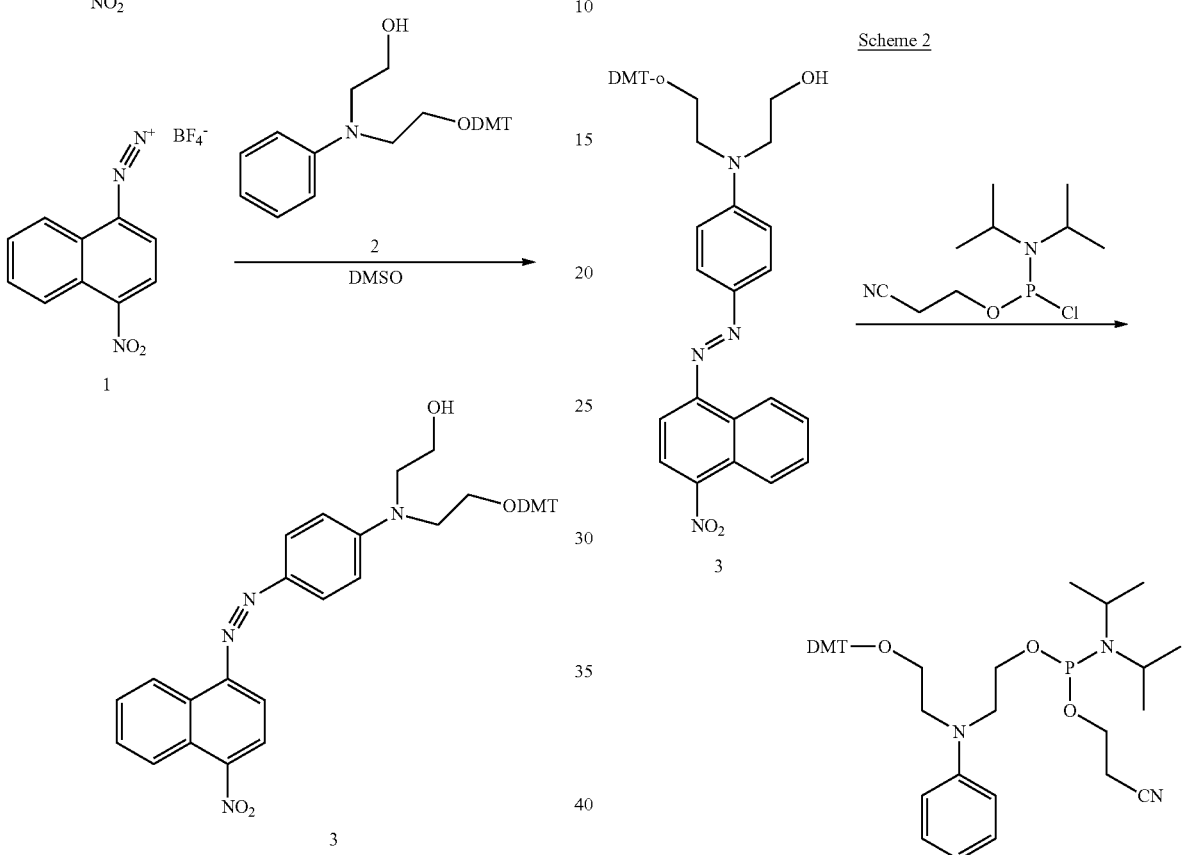

Mono-DMT-4-(1-nitro-4-naphthylazo)-N,N-diethanolaniline (3)

Cold concentrated HCl (17 mL) was added dropwise at 0° C. over 15 min to a suspension of 4-nitro-1-naphthylamine (2 g) in cold water (6 mL) at 0° C. Then NaNO₂ (1.6 g) in cold water (4 mL) was added dropwise at 0° C. over 15 min and the 4-nitro-1-naphthylamine dissolved upon stirring. LiBF₄ (1.38 g) in H₂O (3 mL) was added dropwise at 0° C. The reaction mixture was stirred at 0° C. for 30 min. A brownish yellow powder (3.08 g) of naphthyl-1-nitro-4-tetrafluoroborate azonium salt (1) was obtained after filtering and rinsing the solution with cold water, methanol, and ether. A solution of 4 g of mono-DMT-phenyl diethanolamine (2) in 50 mL of dimethylsulfoxide (DMSO) was added with stirring at 10-15° C. over 10-15 min to a chilled solution of 2.8 g of azonium salt (1) in 50 mL of DMSO at 10-15° C. in a water bath. After an additional 15 min of stirring, 3 mL of triethylamine was added to the reaction mixture followed by 100 mL of ethyl acetate. The reaction mixture was washed with 3×30 mL of deionized water and the organic layer was dried over Na₂SO₄. The solvent was removed and product was purified by column chromatography with 300 g of silica gel to provide 1.8 g of mono-DMT-4-(1-nitro-4-naphtylazo)-NN-diethanolaniline (3). TLC: R$_f$ 0.65 (DCM/Et₃N—80/20). ¹H NMR (CDCl₃) δ 9.04 (d, J=8.4 Hz, 1H), 8.68 (d, J=8.4 Hz, 1H), 8.34 (d, J=8.4 Hz, 1H), 7.96 (d, J=9.2 Hz, 2H), 7.81-7.71 (m, 3H), 7.39 (d, J=8 Hz, 2H), 7.27 (d, J=8 Hz, 4H), 7.24-7.19 (m, 3H), 6.78 (d, J=8 Hz, 4H), 6.77 (d, J=8 Hz, 2H), 3.88 (t, J=7.5 Hz, 2H), 3.75 (s, 6H), 3.78-368 (m, 4H), 3.47 (t, J=7.5 Hz, 2H), 1.57 (br. s, 1H).

Mono-DMT-4-(1-nitro-4-naphthylazo)-N,N-diethanolaniline phosphoramidite (4)

A solution of 0.2 ml of N,N-diisopropylamino-cyanoethyl-phosphoramidolchloride was stirred into a solution of 0.3 g of alcohol (3) in 20 mL of anhydrous THF and 1 mL of triethylamine for 5 min at 0-5° C. After 15 min of additional stirring the reaction mixture was warmed to room temperature. The solvent was evaporated under a vacuum and the residue purified by column chromatography through 50 g of silica gel (EtOAc/PE/TEA: 10/85/5-40/55/5). TLC: R$_f$ 0.65 (DCM/Et₃N—80/20). ¹H NMR (CDCl₃) δ 9.05 (d, J=8.4 Hz, 1H), 8.68 (d, J=8.4 Hz, 1H), 8.34 (d, J=8.4 Hz, 1H), 7.96 (d, J=9.2 Hz, 2H), 7.81-7.71 (m, 3H), 7.39 (d, J=8 Hz, 2H), 7.27 (d, J=8 Hz, 4H), 7.24-7.19 (m, 3H), 6.78 (d, J=8 Hz, 4H), 6.76 (d, J=8 Hz, 2H), 3.85-3.75 (m, J=7.5 Hz, 4H), 3.76 (s, 6H), 3.70 (t, J=7.5 Hz, 2H), 3.41 (t, J=7.5 Hz, 2H), 2.58 (t, J=8.0 Hz, 2H), 1.20 (s, 3H), 1.18 (s, 3H), 1.17 (s, 3H), 1.15 (s, 3H). $^{31}$P NMR δ 148.39.

analysis of the fluorescence curves yielded the melting temperature of the beacon alone (stem $T_m$) and the melting temperature of the probe plus complement (loop $T_m$). Each sample independently was measured a minimum of three times.

Table 15 lists the sequences that were synthesized and tested. The "RQ" is IBRQn-1.

TABLE 15

Molecular beacon sequences

| SEQ ID No. | Name | Sequence |
|---|---|---|
| 128 | beacon | CGCGATCAGACAAGGAGTGGGCTTCATGGATCGCG |
| 129 | complement | TTACATGAAGCCCACTCCTTGTCTATC |
| 130 | 3' Dabcyl | /56-FAM/CGCGATCAGACAAGGAGTGGGCTTCATGGATCGCG/3Dabcyl/ |
| 131 | 3' BHQ-1 | /56-FAM/CGCGATCAGACAAGGAGTGGGCTTCATGGATCGCG/3BHQ-1/ |
| 132 | 3' FQ | /56-FAM/CGCGATCAGACAAGGAGTGGGCTTCATGGATCGCG/3FQ/ |
| 133 | FQ0-FQ | /56-FAM/CGCGATCAGACAAGGAGTGGGCTTCATGGATCGCG/FQ/FQ/ |
| 134 | FQ1-FQ | /56-FAM/CGCGATCAGACAAGGAGTGGGCTTCATGGATCGC/FQ/G/3FQ/ |
| 135 | FQ2-FQ | /56-FAM/CGCGATCAGACAAGGAGTGGGCTTCATGGATCG/FQ/CG/3FQ/ |
| 136 | FQ3-FQ | /56-FAM/CGCGATCAGACAAGGAGTGGGCTTCATGGATC/FQ/GCG/3FQ/ |
| 137 | FQ4-FQ | /56-FAM/CGCGATCAGACAAGGAGTGGGCTTCATGGAT/FQ/CGCG/3FQ/ |
| 138 | FQ5-FQ | /56-FAM/CGCGATCAGACAAGGAGTGGGCTTCATGGA/FQ/TCGCG/3FQ/ |
| 139 | FQ6-FQ | /56-FAM/CGCGATCAGACAAGGAGTGGGCTTCATGG/FQ/ATCGCG/3FQ/ |
| 140 | 3' RQSp | /56-FAM/CGCGATCAGACAAGGAGTGGGCTTCATGGATCGCG/3RQSp/ |
| 141 | FQ0-RQ | /56-FAM/CGCGATCAGACAAGGAGTGGGCTTCATGGATCGCG/FQ//3RQSp/ |
| 142 | FQ1-RQ | /56-FAM/CGCGATCAGACAAGGAGTGGGCTTCATGGATCGC/FQ/G/3RQSp/ |
| 143 | FQ2-RQ | /56-FAM/CGCGATCAGACAAGGAGTGGGCTTCATGGATCG/FQ/CG/3RQSp/ |
| 144 | FQ3-RQ | /56-FAM/CGCGATCAGACAAGGAGTGGGCTTCATGGATC/FQ/GCG/3RQSp/ |
| 145 | FQ4-RQ | /56-FAM/CGCGATCAGACAAGGAGTGGGCTTCATGGAT/FQ/CGCG/3RQSp/ |
| 146 | FQ5-RQ | /56-FAM/CGCGATCAGACAAGGAGTGGGCTTCATGGA/FQ/TCGCG/3RQSp/ |
| 147 | FQ6-RQ | /56-FAM/CGCGATCAGACAAGGAGTGGGCTTCATGG/FQ/ATCGCG/3RQSp/ |

The phosphoramidite (4) can be added to an oligonucleotide during synthesis using standard phosphoramidite oligonucleotide synthetic techniques.

Example 11

The following example demonstrates the utility of the disclosed insertions in a molecular beacon probe.

All Molecular Beacon oligonucleotides were synthesized and purified by Integrated DNA Technologies, Inc. Molecular beacon oligonucleotides at 200 nM were incubated in a buffer consisting of 16.0 mM (NH$_4$)$_2$SO$_4$, 67.0 mM Tris-HCl pH 8.3, 0.01% Tween-20 in the presence and absence of a 1000 nM complementary oligonucleotide. The samples were incubated at 30° C. in a CFX884 Real Time System (BioRad, Hercules, Calif.), and subjected to an increase in temperature from 30-95° C. at a ramp rate of 1° C./min, with fluorescence measurements taken at each degree interval. First derivative Table 16 lists the results of the assay for each beacon.

TABLE 16

| Quencher | Stem $T_m$ | Stem Δ $T_m$ | Loop $T_m$ | Loop Δ $T_m$ |
|---|---|---|---|---|
| 3' Dabcyl | 66 | | 63 | |
| 3' BHQ-1 | 70 | | 62.7 | |
| 3' FQ | 70 | — | 63 | — |
| FQ0-FQ | 72 | 2 | 62 | −1 |
| FQ1-FQ | 68 | −2 | 63 | 0 |
| FQ2-FQ | 70 | 0 | 62 | −1 |
| FQ3-FQ | 71 | 1 | 62 | −1 |
| FQ4-FQ | 72 | 2 | 62 | −1 |
| FQ5-FQ | 74 | 4 | 63 | 0 |
| FQ6-FQ | 75.3 | 5.3 | 64 | 1 |
| 3' RQSp | 74 | — | 61 | — |
| FQ0-RQ | 74 | 0 | 63 | 2 |
| FQ1-RQ | 70 | −4 | 62 | 1 |
| FQ2-RQ | 71 | −3 | 61 | 0 |
| FQ3-RQ | 71 | −3 | 61 | 0 |

TABLE 16-continued

| Quencher | Stem $T_m$ | Stem Δ $T_m$ | Loop $T_m$ | Loop Δ $T_m$ |
|---|---|---|---|---|
| FQ4-RQ | 73 | −1 | 62 | 1 |
| FQ5-RQ | 76 | 2 | 62 | 1 |
| FQ6-RQ | 77 | 3 | 61.3 | 0.3 |

The stability is improved when the FQ quencher is placed internally close to the 3' quencher, particularly with a 3' RQ quencher.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of this disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the various inventions disclosed herein and does not pose a limitation on the scope of any inventions unless otherwise claimed. No language in the specification should be construed as indicating any non-claimed element as essential to the practice of the invention.

Preferred embodiments of various inventions are described herein, including the best mode known to the inventors for carrying out the various inventions. Variations of those preferred embodiments may become apparent to those of ordinary skill in the art upon reading the foregoing description. The inventors expect skilled artisans to employ such variations as appropriate, and the inventors intend for the various inventions to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A composition, comprising:

a first oligonucleotide having the structure 5'-$Y_1$-$L_1$-X-$L_2$-$Y_2$-3', wherein:

$Y_1$ comprises a sequence of DNA or RNA nucleotides, including a first nucleotide $N_1$ having a 3' phosphate covalently linked to $L_1$;

$Y_2$ comprises a sequence of DNA or RNA nucleotides, including a second nucleotide $N_2$ having a 5' phosphate covalently linked to $L_2$;

$L_1$ and $L_2$ each independently are a direct bond or a $C_1$-$C_7$ alkyl, alkynyl, alkenyl, heteroalkyl, substituted alkyl, aryl, heteroaryl, substituted aryl, cycloalkyl, alkylaryl, or alkoxyl group;

X is

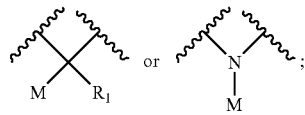

$R_1$ is a hydrogen or a $C_1$-$C_8$ alkyl; and
M is

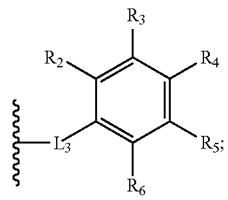

$L_3$ is a direct bond or a $C_1$-$C_8$ alkyl, alkenyl, heteroalkyl, substituted alkyl cycloalkyl, or alkoxyl;

$R_2$-$R_6$ each independently are a hydrogen, an alkyl, an alkenyl, a heteroalkyl, a substituted alkyl, an aryl, a heteroaryl, a substituted aryl, a cycloalkyl, an alkylaryl, an alkoxyl, an electron withdrawing group, or an electron donating group, and one of $R_2$-$R_6$ is

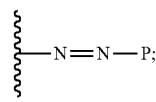

wherein P is

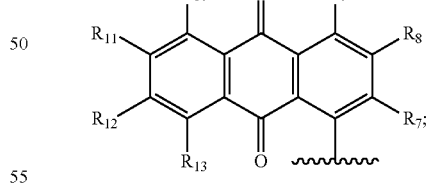

and $R_7$-$R_9$ each independently are a hydrogen, an alkoxyl, an alkyl, an alkylamino, an arylamino, a cycloalkyl, a heteroalkoxyl, a heteroalkyl, or an amino; and $R_{10}$-$R_{13}$ each independently are a hydrogen, a nitro, a cyano, a carboxylate, a sulfonyl, a sulfamoyl, an alkenyl, an alkynyl, an amino, an aryl, a heteroaryl, a biaryl, a bialkenyl, a bialkynyl, an alkoxycarbonyl or a carbamoyl, or wherein P is

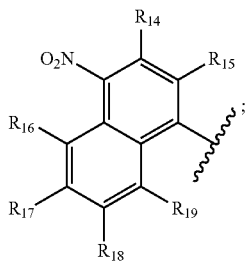

and

R$_{14}$-R$_{19}$ each independently are a hydrogen, an alkyl, a heteroalkyl, an aryl, a heteroaryl, an electron withdrawing group, or a five or six membered ring structure formed from the R$_1$, R$_2$ pair, the R$_3$, R$_4$ pair, the R$_4$, R$_5$, Pair or the R$_5$, R$_6$ pair;

wherein the first oligonucleotide is hybridized to a second oligonucleotide having the structure 3'-Y$_3$-Y$_4$-5', wherein:

Y$_3$ comprises a sequence of DNA or RNA nucleotides, including a third nucleotide N$_3$; and Y$_4$ comprises a sequence of DNA or RNA nucleotides, including a fourth nucleotide N$_4$ that is directly attached to nucleotide N$_3$;

wherein N$_1$ base pairs with N$_3$ and N$_2$ base pairs with N$_4$ such that the duplex has a T$_m$ that is greater than the T$_m$ of a duplex formed between the second oligonucleotide and a third oligonucleotide having the structure 5'-Y$_1$-Y$_2$-3'.

2. The composition of claim 1, wherein L$_1$ and L$_2$ each is a C$_1$-C$_7$ alkyl.

3. The composition of claim 2, wherein L$_1$ and L$_2$ are C$_2$ alkyls.

4. The composition of claim 1, wherein the 3' phosphate that is covalently linked to L$_1$, and the 5' phosphate that is covalently linked to L$_2$, each independently are a phosphodiester, a phosphothioate, a phosphodithioate, a methyl phosphonate, a phosphoramidate, a phosphoramidite or a phosphotriester.

5. The composition of claim 1, wherein:

R$_9$ is

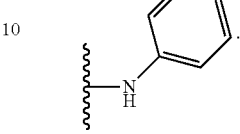

6. The composition of claim 1, wherein the first oligonucleotide is labeled with a fluorophore.

7. The composition of claim 6, wherein the fluorophore is 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX); 1-dimethylaminonaphthyl-5-sulfonate, 1-anilino-8-naphthalene sulfonate, 2-p-toluidinyl-6-naphthalene sulfonate, 5-(2'-aminoethyl)aminonaphthalene-1-sulfonic acid (EDANS), a coumarin dye, an acridine dye, indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyloxacarbocyanine (CyA); 1H,5H, 11H,15H-Xantheno[2,3,4-ij:5,6,7-i'j']diquinolizin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red), a BODIPY™ dye, benzoxaazole, stilbene or pyrene.

8. The composition of claim 6, wherein the fluorophore is attached to the 5' phosphate at the end of the oligonucleotide.

9. The composition of claim 6, wherein the first oligonucleotide is labeled with a second quencher.

\* \* \* \* \*